(12) United States Patent
Pazicky et al.

(10) Patent No.: US 9,115,070 B2
(45) Date of Patent: Aug. 25, 2015

(54) PROCESS FOR PREPARING ACRYLIC ACID FROM ETHYLENE OXIDE AND CARBON MONOXIDE

(71) Applicant: BASF SE, Ludwigshafen (DE)

(72) Inventors: Marek Pazicky, Heidelberg (DE); Christian Raith, Mannheim (DE); Rocco Paciello, Bad Duerkheim (DE); Raphael Heinrich Brand, Rossdorf (DE); Marco Hartmann, Woerth (DE); Klaus Joachim Mueller-Engel, Stutensee (DE); Peter Zurowski, Landau (DE); Wolfgang Fischer, Lingenfeld (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/943,068

(22) Filed: Jul. 16, 2013

(65) Prior Publication Data

US 2014/0018570 A1    Jan. 16, 2014

Related U.S. Application Data

(60) Provisional application No. 61/671,852, filed on Jul. 16, 2012.

(30) Foreign Application Priority Data

Jul. 16, 2012  (DE) .................. 10 2012 212 437

(51) Int. Cl.
| C07C 51/10 | (2006.01) |
| C07C 51/12 | (2006.01) |
| C07C 51/09 | (2006.01) |

(52) U.S. Cl.
CPC ............... *C07C 51/12* (2013.01); *C07C 51/09* (2013.01)

(58) Field of Classification Search
CPC ........ C07C 51/09; C07C 51/12; C07C 57/04; C08G 63/90
USPC ........................................ 562/517
See application file for complete search history.

(56) References Cited

U.S. PATENT DOCUMENTS

| 2,361,036 A | 10/1944 | Kung |
| 2,568,636 A | 9/1951 | Japs |
| 2,820,059 A | 1/1958 | Hasek |
| 2,961,036 A | 11/1960 | Schliephacke |
| 3,002,017 A | 9/1961 | Wearsch et al. |
| 3,260,738 A | 7/1966 | McClure et al. |
| 3,639,466 A * | 2/1972 | Leichtle .................. 562/599 |
| 4,357,462 A | 11/1982 | Kubo et al. |
| 4,777,230 A * | 10/1988 | Kamath ..................... 526/86 |
| 5,359,081 A * | 10/1994 | Drent et al. ............... 549/328 |
| 5,625,029 A * | 4/1997 | Hubbs et al. .............. 528/354 |
| 2004/0171760 A1 | 9/2004 | Slany et al. |
| 2012/0315681 A1 | 12/2012 | Van Walsem et al. |
| 2013/0158230 A1 | 6/2013 | Coates et al. |

FOREIGN PATENT DOCUMENTS

| DE | 2 159 346 A1 | 6/1972 |
| DE | 29 01 347 A1 | 7/1979 |
| DE | 101 31 297 A1 | 1/2003 |
| DE | 101 37 046 A1 | 2/2003 |
| DE | 101 49 269 A1 | 7/2003 |
| DE | 102 43 625 A1 | 4/2004 |
| DE | 103 32 758 A1 | 5/2004 |
| DE | 10 2007 004 960 A1 | 7/2008 |
| DE | 10 2007 043 759 A1 | 9/2008 |
| DE | 10 2008 042 008 A1 | 4/2009 |
| DE | 10 2008 042 010 A1 | 4/2009 |
| DE | 10 2012 204 436 A1 | 10/2012 |
| DE | 10 2011 076 931 A1 | 12/2012 |
| EP | 0 577 206 A2 | 1/1994 |
| EP | 0 688 806 B1 | 12/1995 |
| WO | WO 01/77056 A1 | 10/2001 |
| WO | WO 02/09839 A1 | 2/2002 |
| WO | WO 03/011941 A2 | 2/2003 |
| WO | WO 03/041832 A1 | 5/2003 |
| WO | WO 2004/007405 A1 | 1/2004 |
| WO | WO 2004/031107 A1 | 4/2004 |
| WO | WO 2006/111565 A2 | 10/2006 |
| WO | WO 2010/094637 A1 | 8/2010 |
| WO | WO 2011/004536 A1 | 4/2011 |
| WO | WO 2011/100608 A1 | 8/2011 |
| WO | WO 2011/163309 A2 | 12/2011 |

OTHER PUBLICATIONS

International Search Report issued Oct. 16, 2013 in PCT/EP2013/064767 (with English translation of Categories of Cited Documents).

* cited by examiner

*Primary Examiner* — Yevegeny Valenrod
*Assistant Examiner* — Blaine G Doletski
(74) *Attorney, Agent, or Firm* — Oblon, McClelland, Maier & Neustadt, L.L.P.

(57) ABSTRACT

A process for preparing acrylic acid from ethylene oxide and carbon monoxide, in which ethylene oxide is carbonylated in an aprotic solvent with carbon monoxide in the presence of a cobalt catalyst system to give poly-3-hydroxypropionate, the cobalt content in the poly-3-hydroxypropionate formed is reduced with the aid of water and/or an aqueous solution as a precipitation and/or wash liquid, and the poly-3-hydroxypropionate is subsequently split by thermolysis to give acrylic acid.

43 Claims, No Drawings

PROCESS FOR PREPARING ACRYLIC ACID FROM ETHYLENE OXIDE AND CARBON MONOXIDE

The present invention relates to a process for preparing acrylic acid from ethylene oxide and carbon monoxide, which comprises at least the following process steps:

a carbonylating conversion of ethylene oxide dissolved in an aprotic solvent with carbon monoxide at elevated pressure and elevated temperature in the presence of a catalyst system comprising at least one cobalt source in a reaction zone A to obtain a product mixture A comprising poly-3-hydroxypropionate, a removal of poly-3-hydroxypropionate from the product mixture A in a separation zone A, and a thermolysis of poly-3-hydroxypropionate removed in separation zone A in a thermolysis zone A to form acrylic acid.

Acrylic acid is an important monomer which finds use as such, in the form of its alkyl esters and/or in the form of its alkali metal salts for preparation of polymers. Depending on the specific acrylic monomers used to form the respective polymer, it can be used, for example, as an adhesive or as a superabsorbent for water or aqueous solutions.

It is common knowledge that the industrial scale preparation of acrylic acid currently proceeds essentially by two-stage heterogeneously catalyzed partial gas phase oxidation of propylene (an alternative name=propene) via the acrolein intermediate (cf., for example, DE 10131297 A1 and WO 2004/031107 A1).

The starting propylene used is typically not chemically pure propylene, but crude propylene which still has impurities but has a comparatively high purity (e.g. polymer grade or chemical grade propylene; cf. DE 10131297 A1).

The preparation of such comparatively pure crude propylene is relatively inconvenient and costly. The corresponding production processes normally proceed from crude paraffinic hydrocarbons and generally require several purification stages for the product mixtures thereof, in which the propylene has to be removed from olefins other than propylene and from other by-products other than propylene, which also comprise unconverted crude paraffinic hydrocarbon and secondary components already present therein.

The aforementioned removals are generally capital-intensive and, due to the physical similarity of olefinic/paraffinic hydrocarbons with comparable chain length, also particularly energy-intensive. They are therefore employed typically only in an integrated system with refinery crackers and steamcrackers and can be operated in an economically viable manner only because the predominant amount of the crude propylene thus obtained (as the main propylene demand stream) is firstly required in large amounts ("economy of scale") for downstream polymerizations (for example for preparation of polypropylene) and secondly experiences a high addition of value in the process.

The proportion of these crude propylenes flowing into the heterogeneously catalyzed partial oxidation for preparation of acrylic acid is of comparatively minor importance and basically constitutes merely a secondarily produced demand stream which, supported by the main demand stream, also still has an acceptable raw material cost for the relevant partial oxidation.

The main product formed in the course of cracking of saturated hydrocarbons is, however, ethylene (an alternative name=ethene). Ethylene constitutes the most commonly produced organic commodity chemical and is used, inter alia, for the preparation of primary conversion products such as polyethylene, ethylene oxide (cf., for example, DE 2159346 A1), styrene or α-olefins.

In Europe and Asia, ethylene is produced predominantly on a naphtha or gas oil basis, and in the United States, Canada and the Middle East also from ethane, propane and liquefied gas.

A lowering of the raw material costs associated with the industrial scale preparation of acrylic acid would therefore be possible if the preparation of acrylic acid could proceed from the "ethylene" raw material basis rather than the "propylene" raw material basis.

The thesis "Multi-Site Catalysis—Novel Strategies to Biodegradable Polyesters from Epoxides/CO and Macrocyclic Complexes as Enzyme Models" by Markus Allmendinger, University of Ulm (2003), discloses that carbonylating reaction of ethylene oxide dissolved in an aprotic solvent with carbon monoxide (carbon monoxide likewise constitutes an inexpensive raw material which can be prepared from numerous carbonaceous raw materials, for example natural gas, biogas, light gasoline, heavy oils and biomass) at elevated pressure, elevated temperature and in the presence of a catalyst system comprising at least one cobalt source directly (i.e. without forming the propiolactone (oxetan-2-one) as an intramolecular cyclic ester of β-hydroxypropionic acid (=3-hydroxypropionic acid) as an intermediate) affords a product mixture comprising poly-3-hydroxypropionate.

J. Am. Chem. Soc. 2002, 124, pages 5646-5647, DE 10137046 A1, WO 03/011941 A2 and J. Org. Chem. 2001, 66, pages 5424-5426, confirm this fact.

The term "poly-3-hydroxypropionate" is understood to mean polyesters of the structure

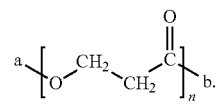

n is an integer ≥2 and may, for example, be up to 150, or up to 200, or up to 250 or more.

a, b are the polyester-terminating end groups, the nature of which depends on the preparation conditions (for example on the catalyst system used).

For example, a may be

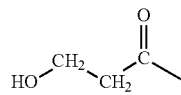

and b may be

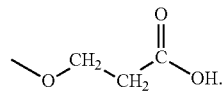

Alternatively, a may be

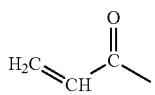

and
b may be

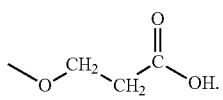

The already mentioned thesis by M. Allmendinger and EP 577 206 A2 disclose that, inter alia, if the product mixture formed in the carbonylation of ethylene oxide in the presence of the cobalt catalyst system is left to stand for a prolonged period, at least a portion of the poly-3-hydroxypropionate present therein precipitates out of the product mixture, and can be removed from the product mixture by using a mechanical separating operation (for example filtration). According to example 7 of EP 577 206 A2, the precipitate of poly-3-hydroxypropionate removed from the product mixture by filtration is subsequently washed with methanol.

The above-cited thesis by M. Allmendinger (for example in the experiment thereof, part X, page A179) and J. Am. Chem. Soc. 2002, 124, page 5646-5647 also disclose that the precipitation of poly-3-hydroxypropionate from the product mixture comprising it can alternatively be brought about by addition of methanol to the product mixture.

A characteristic feature of the processes mentioned for removal of poly-3-hydroxypropionate from the product mixture which is produced in the case of carbonylation of the ethylene oxide in the presence of a catalyst system comprising at least one cobalt source is that the isolated poly-3-hydroxypropionate still has a non-negligible cobalt content.

EP 577 206 A2 discloses that poly-3-hydroxypropionate is split under the action of elevated temperatures (i.e. by thermolysis) into acrylic acid (the dehydrate of 3-hydroxypropionic acid). EP 577 206 A2, however, does not comprise any example of such a thermolysis.

WO 2011/100608 A1 likewise discloses that thermolysis of poly-3-hydroxypropionate can produce acrylic acid. The poly(3-hydroxypropionic acid) is prepared by biotechnological means in genetically modified biological organisms (for example from sugars as renewable raw materials), and hence in the absence of cobalt catalysts. The thermal splitting of poly-3-hydroxypropionate to give acrylic acid is also known from U.S. Pat. No. 2,568,636 A, from U.S. Pat. No. 2,361,036 A and from U.S. Pat. No. 3,002,017 A. The polyesters of β-hydroxypropionic acid used therein for the redissociation are obtained proceeding from β-propiolactone (in the absence of cobalt catalysts) by ring-opening polymerization. Corresponding ring-opening polymerizations are also disclosed by EP 688 806 B1 and WO 2011/163309 A2. In addition, poly-3-hydroxypropionate which can be redissociated to acrylic acid can be obtained in the absence of cobalt catalysts by dehydrating polycondensation of 3-hydroxypropionic acid (cf., for example, Chinese journal of synthetic chemistry, Vol. 15 (2007) No. 4, pages 452-453).

A disadvantage of these known processes for preparation of poly-3-hydroxypropionate as the basis for thermolytic production of acrylic acid, the performance of which does not require the presence of a cobalt catalyst, is that the economic viability thereof is unsatisfactory.

A disadvantage of poly-3-hydroxypropionate which is obtained in the carbonylation of ethylene-based ethylene oxide in the presence of a catalyst system comprising at least one cobalt source and is removed according to the specifications of the prior art from the product mixture which forms has been found to be the already mentioned cobalt content thereof.

In-house studies by the applicant have namely shown in a surprising manner that cobalt remaining in the poly-3-hydroxypropionate removed significantly impairs the thermolysis thereof to acrylic acid.

It was therefore an object of the present invention to provide an improved process for preparing poly-3-hydroxypropionate from ethylene oxide and carbon monoxide in the presence of a catalyst system comprising at least one cobalt source, which especially comprises improved removal of the poly-3-hydroxypropionate from the cobalt present in the product mixture.

Accordingly, a process is provided for preparing acrylic acid from ethylene oxide and carbon monoxide, which comprises at least the following process steps:
  a carbonylating conversion of ethylene oxide dissolved in an aprotic solvent with carbon monoxide at elevated pressure and elevated temperature in the presence of a catalyst system comprising at least one cobalt source in a reaction zone A to obtain a product mixture A comprising poly-3-hydroxypropionate,
  a removal of poly-3-hydroxypropionate from the product mixture A in a separation zone A, and
  a thermolysis of poly-3-hydroxypropionate removed in separation zone A in a thermolysis zone A to form acrylic acid,
wherein the removal of poly-3-hydroxypropionate from product mixture A in separation zone A comprises at least one of the following process measures:
  an addition of water and/or an aqueous solution as an aqueous precipitation liquid to one or more portions of product mixture A and/or to the total amount of product mixture A in order to precipitate (and to decobaltize) poly-3-hydroxypropionate present dissolved in a portion of product mixture A or in the total amount of product mixture A,
  a wash of poly-3-hydroxypropionate removed from product mixture A with water and/or with an aqueous solution as an aqueous wash liquid (for the purpose of decobaltizing the poly-3-hydroxypropionate removed).

An aprotic solvent is understood by definition to mean (aprotic) organic substances=(chemical) compounds (and mixtures of two or more than two of these compounds (substances)) which are liquid at a pressure of $1.0133 \cdot 10^5$ Pa (=standard pressure) at at least one of the temperatures within the range from 0° C. to 50° C., preferably at at least one of the temperatures within the range from 5° C. to 40° C. and more preferably at at least one of the temperatures within the range from 10° C. to 30° C., do not comprise any atom other than carbon (any atom type other than carbon) to which a hydrogen atom is covalently bonded, and are neither ethylenically nor alkynically unsaturated (in each case singly or multiply).

The boiling point of ethylene oxide at standard pressure is at a temperature of 10.45° C. If the ethylene oxide is used in a (molar) excess in the process according to the invention, based on the available molar amount of CO and the stoichiometry of the carbonylating reaction (of the carbonylation), the ethylene oxide in the process according to the invention may also itself constitute the aprotic solvent required in accordance with the invention (or be part of such an aprotic solvent, be encompassed by such an aprotic solvent).

Further aprotic solvents suitable for the process according to the invention include, by way of example, saturated (cyclic and acyclic) and aromatic hydrocarbons such as n-hexane, n-heptane, petroleum ether, cyclohexane, benzene and toluene, halogenated saturated and aromatic hydrocarbons such as dichloromethane, esters of organic acids (especially organic carboxylic acids) such as n-butyl propionate, phenyl acetate, glyceryl triacetate and ethyl acetate, anhydrides of organic carboxylic acids such as acetic anhydride, ketones such as acetone, ethyl methyl ketone, methyl isobutyl ketone and benzophenone, nitriles such as acetonitrile, propionitrile, n-butyronitrile and benzonitrile, dialkylamides such as dimethylformamide and dimethylacetamide, carbonic esters such as dimethyl carbonate, diethyl carbonate, ethyl methyl carbonate, ethylene carbonate and propylene carbonate, sulfoxides such as dimethyl sulfoxide, sulfones such as sulfolane, N-alkylpyrrolidones such as N-methylpyrrolidone, and cyclic and acyclic ethers such as diethyl ether, anisole, tetrahydrofuran, 1,4-dioxane, diphenyl ether, alkylene glycol dialkyl ethers (e.g. ethylene glycol dialkyl ethers such as ethylene glycol dimethyl ether) and polyalkylene glycol dialkyl ethers such as diethylene glycol diethyl ether, diethylene glycol dimethyl ether (=diglyme), triethylene glycol dimethyl ether (=triglyme) and tetraethylene glycol dimethyl ether (=tetraglyme).

Protic solvents (=(protic) compounds=(protic) substances and mixtures thereof which comprise at least one atom other than carbon to which a hydrogen atom is bonded covalently) may take part in the reaction underlying the process according to the invention and lead to unwanted by-product formation, which is why they are not very suitable for use for the process according to the invention. (Methanol, ethanol, n-butanol, tert-butanol, cyclohexanol and other alcohols are, for example, not aprotic substances but are protic solvents.) Equally, solvents which are substances which are ethylenically and/or alkynically unsaturated are not aprotic solvents in the inventive sense.

Aprotic solvents preferred in accordance with the invention are those which comprise substances having at least one covalently bonded oxygen atom. This is especially true when the oxygen atom is at least one ether oxygen atom (an oxygen atom which forms an ether bridge).

In addition, it is advantageous in accordance with the invention when the aprotic solvent is a substance (or more than one substance) (or comprises one or more such substances) which comprises at most oxygen and/or sulfur as an atom type other than carbon and hydrogen.

If the substance used as the aprotic solvent in the process according to the invention has, for example, one or more tertiary nitrogen atoms, these can to a limited degree counteract the polyester formation desired in the process according to the invention.

The poly-3-hydroxypropionates produced in the process according to the invention are polyesters having a moderate polarity.

Aprotic solvents suitable in accordance with the invention therefore preferably comprise (or are) those substances (compounds) whose relative static (=whose dielectric constant=whose dielectric number=whose permittivity number) $\epsilon$ at a temperature of 293.15 K and a pressure of $1.0133 \cdot 10^5$ Pa (=standard pressure) as a pure liquid substance is in the range from 2 to 35, preferably 3 to 20, more preferably 4 to 15 and most preferably 5 to 10 (the relative static permittivity of vacuum=1).

If the relevant aprotic substance is not liquid but solid at 293.15 K and standard pressure, the above statement relates to the melting point temperature thereof at standard pressure.

If the relevant aprotic substance (aprotic (chemical) compound) is not liquid but gaseous at 293.15 K and standard pressure, the above statement relates to a temperature of 293.15 K and the corresponding saturation vapor pressure (the (autogenous) vapor pressure at which the substance condenses at 293.15 K).

A suitable source with figures for relative static permitivities of aprotic substances relevant in accordance with the invention is, for example, the HANDBOOK of CHEMISTRY and PHYSICS, 92nd Edition (2010-2011), CRC PRESS. According to the figures therein, the relevant $\Delta$ is, for example, 7.56 for tetrahydrofuran, 12.43 for ethylene oxide, 2.22 for 1,4-dioxane, 7.41 for ethylene glycol dimethyl ether (1,2-dimethoxyethane), 7.38 for diethylene glycol dimethyl ether (diglyme) and 7.62 for triethylene glycol dimethyl ether (triglyme).

Aprotic solvents which are very particularly preferred in accordance with the invention are therefore those which comprise aprotic organic compounds which are relevant in accordance with the invention and whose relevant $\epsilon$ is 2 to 35, advantageously 3 to 20, particularly advantageously 4 to 15 and very particularly advantageously 5 to 10, and which simultaneously comprise at least one covalently bonded oxygen which is particularly advantageously an ether oxygen atom.

Aprotic solvents comprising or consisting of ethylene glycol dimethyl ether, diethylene glycol dimethyl ether and triethylene glycol dimethyl ether and any desired mixtures thereof are therefore aprotic solvents very particularly suitable for the process according to the invention, among which preference is once again given to diethylene glycol dimethyl ether.

It will be appreciated that the term "aprotic solvents" in the context of the present invention also comprises those solvents which do not consist to an extent of 100% of their weight (but only to an extent of 90% of their weight, or only to an extent of 95% of their weight, or only to an extent of 98% of their weight, or only to an extent of 99% of their weight) of aprotic organic compounds according to the definition (aprotic organic substances, aprotic organic solvents).

In other words, it is already sufficient for the purposes of the present invention and encompassed by the term "aprotic solvent" when the "aprotic solvent" used consists to an extent of at least 90% by weight, preferably to an extent of at least 95% by weight, more preferably to an extent of at least 98% by weight and most preferably to an extent of at least 99% by weight (based in each case on the weight of the solvent) of aprotic organic compounds according to the definition.

Such a constituent of the aprotic solvent not according to the definition may be, for example, protic substances such as water or alcohols. Since they can cause, for example by way of "ester formation", termination of a poly-3-hydroxypropionate chain growing in the process according to the invention, controlled presence of such protic substances can result in a controlled influence on the mean molecular weight of the poly-3-hydroxypropionate which results in the course of performance of the process according to the invention (cf., for example, DE 10137046 A1). With increasing absence (generated (brought about), for example, by addition of "water scavengers", as recommended by DE 10137046 A1) of such protic substances, the result is increasingly higher mean molecular weights of the poly-3-hydroxypropionate under otherwise identical reaction conditions.

The termination of a poly-3-hydroxypropionate chain growing in the course of the process according to the invention by a protic substance, for example water, is generally advantageous in accordance with the invention, on the one hand, in that a bond of the growing polyester chain to the cobalt of the catalyst system is probably broken on termination (on chain termination).

On the other hand, such a termination is associated with the disadvantage that, in the course of inventive thermolysis of the poly-3-hydroxypropionate, for example, the water which causes such a termination may be eliminated again and hence released. If the inventive carbonylating reaction is effected with complete exclusion of such protic substances (i.e., for example, with exclusion of the air humidity and other traces of water), the chain termination described also cannot be effected until an inventive precipitation and/or washing of the poly-3-hydroxypropionate formed.

Typical relative (i.e. based on the weight of atomic hydrogen) weight-average molecular weights $M_W$ of poly-3-hydroxypropionate obtainable in a process according to the invention (i.e. of poly-3-hydroxypropionate removed from a product mixture A) may, for example, be 1000 to 20 000 or 2000 to 15 000, in many cases 3000 to 12 000 and frequently 4000 to 10 000. In principle, however, higher and lower relative weight-average molecular weights $M_W$ are also possible. The corresponding polydispersity Q (the ratio of weight-average relative molecular weight $M_W$ to number-average relative molecular weight $M_n$ ($Q=M_W/M_n$)) is generally at values of ≤2.5, frequently at values of ≤2. In many cases, Q is 1.5 to 1.8. However, it is also possible to establish polydispersities Q below 1.5 or below 1.4 (cf. DE 10137046 A1).

Useful further constituents of an inventive aprotic solvent not according to the definition include, for example, preparation-related impurities thereof.

Since ethylene oxide itself has a moderate polarity (the relevant value for $\epsilon=12.43$), sufficient solubility thereof in the aprotic solvents to be used in accordance with the invention is normally uncritical.

In other words, the type and amount of aprotic solvent to be used in accordance with the invention are generally guided primarily by their being sufficient under the reaction conditions to be employed in accordance with the invention to keep the amount of the cobalt-comprising catalyst system required in accordance with the invention in solution in the reaction mixture, since the process according to the invention is preferably performed under homogeneous catalysis.

Based on the molar amount of ethylene oxide to be converted by carbonylation in the course of performance of the process according to the invention, the molar use amount of Co present in the at least one cobalt source of the catalyst system in the process according to the invention is normally in the range from 0.005 to 20 mol %, preferably in the range from 0.05 to 10 mol %, more preferably in the range from 0.1 to 8 mol % and most preferably in the range from 0.5 to 5 mol %. In the case of use amounts of Co present in the at least one cobalt source of the catalyst system on a corresponding basis of ≤0.0001 mol %, there is generally essentially no inventive carbonylating conversion ("multisite catalysis").

The cobalt source suitable in accordance with the invention used for the process according to the invention may essentially be any cobalt-comprising chemical compound since this is generally converted under the carbon monoxide pressure to be employed in the process according to the invention to the actual catalytically active compound of cobalt in each case.

Examples of cobalt sources suitable in accordance with the invention include cobalt salts such as cobalt formate, cobalt acetate, cobalt acetylacetonate and cobalt sulfate, which are readily carbonylated under the carbon monoxide pressures to be employed in accordance with the invention ("in situ"; presence of small amounts of molecular hydrogen may have an advantageous effect in this regard). However, finely divided cobalt metal (for example in dust form) can also be used as the cobalt source in the process according to the invention.

Preferably in accordance with the invention, the cobalt sources used are already preformed cobalt carbonyl compounds (this is understood to mean compounds comprising at least one cobalt atom and at least one carbon monoxide ligand), among which very particular preference is given to dicobalt octacarbonyl ($Co_2(CO)_8$) (as $[Co(CO)_4^+Co(CO)_4^-]$, this effectively comprises preformed $Co(CO)_4^-$). Appropriately in application terms, it is used as the sole cobalt source in the catalyst system.

Without being bound to the assumption which follows, it is assumed that an important catalytically active species in the chain initiation of a process according to the invention is hydrotetracobalt carbonyl ($HCo(CO)_4$) (cf., for example, DE 10137046 A1).

The formation of hydrotetracobalt carbonyl from cobalt carbonyl compounds such as $Co(CO)_8$ generally sets in whenever compounds having bound hydrogen are present in the reaction mixture. Cobalt carbonyl compounds such as $Co_2(CO)_8$ can even pull hydrogen out of amines and paraffins (cf. Organische Chemie in Einzeldarstellungen 10, Jürgen Falbe, Synthesen mit Kohlenmonoxyd [Syntheses with carbon monoxide], Springer Verlag (1967), p. 14). Presence of small amounts of molecular hydrogen may possibly have an advantageous effect here.

Additional use of small amounts of a Brønsted acid (or a plurality thereof) (the reference basis for the "Brønsted acid" property in this document is 25° C. and standard pressure with water as the reaction partner for the Brønsted acid; this means that the addition of a Brønsted acid to water (at 25° C. and standard pressure) gives an aqueous solution having a lower pH under the given conditions than pure water) as cocatalysts (also called "promoters") can promote the formation of hydrotetracobalt carbonyl as a possibly rate-determining step and thus accelerate the desired inventive polyester formation (cf. DE 10149269 A1 and DE 10137046 A1).

Such Brønsted acids suitable in accordance with the invention ("cocatalysts A" or "promoters A") include the customary mineral acids (inorganic acids) such as hydrochloric acid, sulfuric acid or phosphoric acid, in dilute and especially in concentrated form, organic carboxylic acids, for example alkanemono- and -polycarboxylic acids (e.g. formic acid, acetic acid, adipic acid and glutaric acid), the halogenated derivatives thereof, for example trichloro- and trifluoroacetic acid, and aromatic carboxylic acids, for example benzoic acid and 2,4,6-trimethylbenzoic acid, organic sulfonic acids such as p-toluenesulfonic acid, hydroxyaromatic compounds such as phenol, 1-naphthol and 2-naphthol, but also water (in this document, water is arbitrarily assigned to the Brønsted acids).

Phenol and acetic acid are Brønsted acids preferred in accordance with the invention for the aforementioned purpose. Acetic acid is preferably used in the form of what is called glacial acetic acid. This shall be understood to mean predominantly anhydrous or virtually anhydrous acetic acid (the water content thereof is preferably ≤1% by weight, more preferably ≤0.5% by weight, advantageously ≤0.1% by weight and most preferably ≤0.01% by weight). Hydrochloric acid is preferably used in dissolved form in the aprotic solvent to be used in accordance with the invention. As already stated, it is also possible to use any desired mixtures of the Brønsted acids listed for the inventive purpose explained above.

In general, Brønsted acids ("promoters A", "cocatalysts A") will be used in the process according to the invention in such total molar amounts $M_A$ as cocatalysts A that the $M_A:M_{Co}$ ratio formed with the total molar amount $M_{Co}$ of Co present in the catalyst system used (in this document, this manner of expression always means the total molar amount of Co (atoms+ ions) present in the total amount of all cobalt sources in a catalyst system) is 5:1 to 1:5, preferably 4:1 to 1:4, more preferably 3:1 to 1:3 and most preferably 2:1 to 1:2.

Remarkably, Brønsted bases used additionally in small amounts (the reference basis for the "Brønsted base" property in this document is 25° C. and standard pressure with water as the reaction partner for the Brønsted base; this means that the addition of a Brønsted base to water (at 25° C. and standard pressure) gives an aqueous solution having a higher pH under the given conditions than pure water) likewise constitute cocatalysts suitable in accordance with the invention ("promoters B" or "cocatalysts B"); cf., for example, U.S. Pat. No. 2,820,059 A; Organische Chemie in Einzeldarstellungen 10, Jürgen Falbe, Synthesen mit Kohlenmonoxyd, Springer Verlag (1967), page 16; DE 10137046; U.S. Pat. No. 3,260,738 A; and DE 2901347 A1).

It is suspected that they promote chain growth as nucleophilic substances in the inventive polyester formation (cf. J. Am. Chem. Soc. 2002, 124, pages 5646-5647).

This is especially true when the $pK_B$ thereof (based on 25° C., standard pressure and water), as a measure of the corresponding Brønsted base strength, is ≥7, advantageously ≥8, preferably ≥9 and more preferably ≥10, i.e. the bases are weak Brønsted bases. In general, the $pK_B$ thereof is ≤30, often ≤25.

The corresponding nucleophilic site of the Brønsted base is preferably at least one oxygen atom (as, for example, in the case of the acetate ion), a phosphorus atom (as, for example, in the case of triphenylphosphine) and/or at least one nitrogen atom (as, for example, in the case of aniline or pyridine). However, halide ions such as $I^-$, $Cl^-$ and $F^-$ may also constitute such nucleophiles.

According to the invention, Brønsted bases particularly suitable as nucleophilic cocatalysts B are aromatic and nonaromatic cyclic compounds having at least one (frequently also 2, or 3) nitrogen atom(s) in the ring as well as carbon atoms (aromatic nitrogen heterocycles and nitrogen heteroalicycles). For example, the rings may be 5-, 6- or 7-membered.

Examples of promoters B suitable in accordance with the invention include pyrrole, N-methyl-2-pyrrolidone, 2-pyrrolidone, 3-pyrrolidone, piperidine, N-methylpiperidine, indole, indoline, imidazole, pyrazole, N,N-dimethylformamide, acetanilide and N-methylimidazole.

Promoters B preferred in accordance with the invention are weakly basic nitrogen heterocycles such as pyrrole, N-methyl-2-pyrrolidone, 2-pyrrolidone, 3-pyrrolidone, piperidine, N-methylpiperidine, imidazole, pyrazole and N-methylimidazole.

It will be appreciated that the aromatic or nonaromatic nitrogen heterocycle may also be fused to aliphatic or aromatic ring systems (for example 5-, 6-, or 7-membered), and these may in turn likewise have one or more nitrogen (hetero) atoms. Examples include indole, indoline, quinoline, isoquinoline, quinoxaline, 1,10-phenanthroline and 2,2'-, 2,3'-, 3,3'-, 2,4'-, 3,4'- and 4,4'-bipyridine.

In general, promoters B (Brønsted bases) will be used as cocatalysts B in the process according to the invention in such total molar amounts $M_B$ that the $M_B:M_{Co}$ ratio, formed with the total molar amount $M_{Co}$ of Co present in the catalyst system used, is 5:1 to 1:5, preferably 4:1 to 1:4, more preferably 3:1 to 1:3 and most preferably 2:1 to 1:2. Excessively large excesses of promoters B with respect to the molar amount of Co present should be avoided, since the cocatalytic effect can become an inhibition with increasing excess.

Advantageously in accordance with the invention, a catalyst system to be used in accordance with the invention comprises, as well as at least one cobalt source, additionally also at least one cocatalyst A and at least one cocatalyst B (for example the combination of phenol as cocatalyst A and pyridine as cocatalyst B).

The $M_A:M_B$ ratio, formed from the total molar amount $M_A$ of cocatalysts A present in the reaction mixture and the total molar amount $M_B$ of cocatalysts B present in the reaction mixture, in accordance with the invention, is advantageously 1:4 to 4:1, particularly advantageously 1:2 to 2:1 and frequently 1:1.

It is very particularly advantageous in accordance with the invention to additionally use, as cocatalysts C (at least one) in the catalyst system which comprises at least one cobalt source and is to be used in accordance with the invention, those compounds which have both at least one nucleophilic Brønsted-basic functionality such as a cocatalyst B and at least one Brønsted-acidic functionality such as a cocatalyst A (i.e. if these compounds comprised only the at least one Brønsted-acidic (or only the at least one Brønsted-basic) functionality and no Brønsted-basic (or Brønsted-acidic) functionality, they would constitute a Brønsted acid, i.e. a cocatalyst A (a Brønsted base, i.e. a cocatalyst B)).

These cocatalysts C ("promoters C") include especially aromatic nitrogen heterocycles (these may, for example, be 5-, 6- or 7-membered rings; they have at least one nitrogen atom in the aromatic ring (cycle)) which have, in the molecule, in addition to the Brønsted-basic nitrogen, at least one Brønsted-acidic (free) hydroxyl group (—OH) and/or at least one Brønsted-acidic (free) carboxyl group (—COOH) in covalently bonded form. It will be appreciated that the aromatic nitrogen heterocycle may again be fused to other aromatic and/or aliphatic (for example 5-, 6- or 7-membered) ring systems. The at least one hydroxyl group and/or carboxyl group may be present either on the aromatic base nitrogen heterocycle (preferably) or on the fused aliphatic and/or aromatic ring system, or on both. It will be appreciated that the fused moiety may also have one or more than one nitrogen atom as a heteroatom. As well as the at least one hydroxyl group and/or carboxyl group, it is additionally also possible, for example, for aliphatic, aromatic and/or halogen substituents to be present.

Examples of cocatalysts C particularly preferred in accordance with the invention include 2-hydroxypyridine, 3-hydroxypyridine, 4-hydroxypyridine, 3,4-dihydroxypyridine, 3-hydroxyquinoline, 4-hydroxy-2-methylpyridine, 3-hydroxy-4-methylpyridine, 2,6-dihydroxypyridine, 2-hydroxyquinoline, 1-hydroxyisoquinoline, 3-hydroxyquinoline, 2,3-dihydroxyquinoxaline, 8-hydroxyquinoline, 2-pyridylmethanol, 3-pyridylmethanol and 2-(2-pyridyl)ethanol. Of course, as already stated, instead of and/or in addition to the hydroxyl group, a carboxyl group may be present, as is the case for nicotinic acid. Most preferably, the cocatalyst C used in the process according to the invention is 3-hydroxypyridine (especially in combination with diglyme as an aprotic solvent and dicobalt octacarbonyl as a cobalt source in the catalyst system).

In general, promoters C will be used as cocatalysts C in the process according to the invention in such molar total amounts $M_C$ that the $M_C:M_{Co}$ ratio, formed with the total molar amount $M_{Co}$ of Co present in the catalyst system used, is 5:1 to 1:5, preferably 4:1 to 1:4, more preferably 3:1 to 1:3 and most preferably 2:1 to 1:2 or 2:1 to 1:1. Advantageously, a catalyst system comprising at least one promoter C comprises neither a promoter A nor a promoter B (however, these may of course be additional constituents of the catalyst system).

Table 1 below quantifies, by way of example, catalyst systems suitable for the process according to the invention, including a suitable amount of ethylene oxide (EO) for carbonylating conversion and an amount of the aprotic solvent diglyme (Solv.) appropriate for the resulting reaction mixture, in terms of the use amounts and use amount ratios thereof. The cobalt source Q used is always $Co_2(CO)_8$.

Carbon monoxide is preferably used in excess (relative to the reaction stoichiometry) in all aforementioned cases.

It will be appreciated that, for a process according to the invention, it is also possible to use salts of the anion $Co(CO)_4^-$ and/or the Brønsted acid thereof $HCo(CO)$ as cobalt sources. Examples of such salts are tetramethylammonium tetracarbonylcobaltate(−1)=$Et_4NCo(CO)_4$ and bis(triphenylphosphoranylidene)ammonium tetracarbonylcobaltate(−1). Further examples are disclosed, for example, by DE 10149269 A1.

TABLE 1

| Solv. | EO | Q | Cocatalysts |
|---|---|---|---|
| 37.6 g | 0.2 mol | 1 mmol | 4 mmol 3-hydroxypyridine |
| 94 g | 0.6 mol | 2 mmol | 4 mmol 3-hydroxypyridine |
| 75.2 g | 0.4 mol | 2 mmol | 7.9 mmol 3-hydroxypyridine |
| 9.4 g | 0.1 mol | 0.32 mmol | 1.6 mmol 3-hydroxypyridine |
| 9.4 g | 0.11 mol | 0.32 mmol | 0.64 mmol 3-hydroxypyridine |
| 75.2 g | 0.4 mol | 2 mmol | 4 mmol 3-hydroxypyridine |
| 75.2 g | 0.4 mol | 2 mmol | 8 mmol 3-hydroxypyridine |
| 75.2 g | 0.4 mol | 2 mmol | 0.5 mmol 3-hydroxypyridine |
| 75.2 g | 0.4 mol | 2 mmol | 8 mmol 3-hydroxypyridine<br>8 mmol acetic acid |
| 75.2 g | 0.4 mol | 2 mmol | 4 mmol pyridine<br>8 mmol acetic acid |
| 75.2 g | 0.4 mol | 2 mmol | 4 mmol pyridine<br>8 mmol phenol |
| 75.2 g | 0.4 mol | 2 mmol | 8 mmol 2,6-difluoropyridine<br>8 mmol phenol |
| 75.2 g | 0.4 mol | 2 mmol | 4 mmol aniline<br>8 mmol acetic acid |
| 75.2 g | 0.4 mol | 2 mmol | 4 mmol 2-methylpyridine<br>8 mmol acetic acid |
| 75.2 g | 0.4 mol | 2 mmol | 2 mmol 2,2'-bipyridine<br>8 mmol acetic acid |
| 75.2 g | 0.4 mol | 2 mmol | 4 mmol 2,2'-bipyridine<br>8 mmol acetic acid |
| 75.2 g | 0.4 mol | 2 mmol | 4 mmol 2,2'-bipyridine<br>12 mmol acetic acid |
| 75.2 g | 0.4 mol | 2 mmol | 4 mmol 2,2'-bipyridine<br>8 mmol phenol |
| 75.2 g | 0.4 mol | 2 mmol | 2 mmol 1,10-phenanthroline<br>8 mmol acetic acid |
| 75.2 g | 0.4 mol | 2 mmol | 2 mmol 1,10-phenanthroline<br>8 mmol phenol |
| 75.2 g | 0.4 mol | 2 mmol | 4 mmol imidazole<br>8 mmol methanol |
| 75.2 g | 0.4 mol | 2 mmol | 8 mmol pyrazole |
| 75.2 g | 0.4 mol | 2 mmol | 4 mmol CsF<br>4 mmol acetic acid |
| 75.2 g | 0.4 mol | 2 mmol | 4 mmol CsF<br>8 mmol acetic acid |
| 75.2 g | 0.4 mol | 2 mmol | 4 mmol Cs acetate<br>8 mmol acetic acid |
| 75.2 g | 0.4 mol | 2 mmol | 8 mmol Cs acetate<br>16 mmol acetic acid |
| 75.2 g | 0.4 mol | 2 mmol | 4 mmol K acetate<br>8 mmol acetic acid |
| 75.2 g | 0.4 mol | 2 mmol | 4 mmol K acetate<br>4 mmol acetic acid |
| 75.2 g | 0.4 mol | 2 mmol | 4 mmol Na acetate<br>4 mmol acetic acid |
| 9.4 g | 0.125 mol | 0.41 mmol +<br>0.825 mmol $Et_4N\,Co(CO)_4$ | 0.825 mmol acetic acid |
| 75.2 g | 0.4 mol | 2 mmol | 4 mmol Li acetate<br>4 mmol acetic acid |
| 75.2 g | 0.4 mol | 2 mmol | 4 mmol Cs acetate<br>8 mmol trifluoroacetic acid |
| 75.2 g | 0.4 mol | 2 mmol | 4 mmol Cs acetate<br>8 mmol p-toluenesulfonic acid |
| 75.2 g | 0.4 mol | 2 mmol | 4 mmol Cs acetate<br>8 mmol 2,4,6-trimethylbenzoic acid |

The reaction temperature to be employed in the inventive carbonylating conversion and the working pressure to be employed in the inventive carbonylating conversion are uncritical and may vary within wide limits. It is an advantageous feature of the process according to the invention that the carbonylating conversion can be executed under comparatively mild reaction conditions. Suitable reaction temperatures are in the range from 25 to 150° C., preferably in the range from 35 or 50 to 120° C., more preferably in the range from 60 to 100° C. and most preferably in the range from 70 to 90° C. At comparatively low temperatures, the carbonylating conversion proceeds with a somewhat reduced reaction rate, but with a comparatively increased target product selectivity close to 100 mol %.

Superatmospheric working pressures promote the inventive carbonylating conversion. Appropriately in application terms, the working pressure (the absolute pressure in the gas atmosphere of the reaction space (which is normally within a pressure reactor)) in the inventive carbonylating conversion does not normally exceed $2.5 \cdot 10^7$ Pa (abs.), since higher working pressures normally result in excessive plant costs. Working pressures of $2 \cdot 10^5$ Pa to $2 \cdot 10^7$ Pa are advantageous in accordance with the invention. Preferably in accordance with the invention, for the inventive carbonylating conversion, a working pressure in the range from $5 \cdot 10^5$ Pa to $1.5 \cdot 10^7$ Pa, more preferably in the range from $1 \cdot 10^6$ Pa to $1 \cdot 10^7$ Pa and most preferably in the range from $2 \cdot 10^6$ Pa to $9 \cdot 10^6$ Pa or in the range from $4 \cdot 10^6$ Pa to $8 \cdot 10^6$ Pa is employed. In a manner corresponding to the above, the inventive carbonylating conversion is typically performed in a pressure vessel (in an autoclave, in a pressure reactor) as reaction zone A.

Oxidizing gases such as $O_2$, $CO_2$ and steam normally act as catalyst poisons with respect to the inventive carbonylating conversion and are therefore excluded substantially or preferably completely from the carbon monoxide to be used (and generally from the reaction mixture constituents to be used). The individual proportions by volume thereof in the total volume of the carbon monoxide used should be ≤1% by volume, better ≤0.1% by volume, preferably ≤0.01% by volume, more preferably ≤0.001% by volume and most preferably vanishingly small. In other words, preference is given to performing the inventive polyester formation under inert conditions, i.e. in the absence of moisture and air. Since ethylene oxide is a highly flammable gas, presence of molecular oxygen is also prohibitive from this point of view in the inventive carbonylation. Steam is additionally able to open the ethylene oxide ring in an undesirable manner, which is why presence of steam (apart from the small amounts already mentioned) in the pressure vessel is undesirable from this angle too.

The carbon monoxide to be used for the inventive carbonylating conversion can thus be supplied to the pressure reactor either in a mixture with inert gases (for example $N_2$, noble gases such as Ar) or essentially as a pure substance. The latter is preferred in accordance with the invention, and therefore the working pressures detailed above for the inventive carbonylating conversion also constitute favorable Co partial pressures (present in the gas atmosphere of the reaction space) for the inventive carbonylation.

As already mentioned, the inventive carbonylating conversion is normally performed in a pressure vessel closeable in a gastight manner for reactions in the elevated pressure range (in an autoclave=reaction zone A). In principle, the inventive polyester formation in a pressure reactor can be performed either batchwise or continuously. If it is performed batchwise, the working pressure (and with it the CO partial pressure) can be kept constant, or can decline following the conversion of the carbonylation. The former is possible in a simple manner by constantly replenishing spent CO in the reaction space of the pressure reactor.

For an inventive carbonylation, for example, carbon monoxide 2.3 from GCH Gerling Holz & Handels GmbH is suitable, this having the following specifications (the figures relate to the gas phase):
≥99.3% by vol. of CO,
≤4000 ppm by vol. of $N_2$,
≤3500 ppm by vol. of $O_2$,
≤3500 ppm by vol. of Ar,
≤1000 ppm by vol. of $H_2$,
≤500 ppm by vol. of $CO_2$,
≤500 ppm by vol. of hydrocarbons (total), and
≤20 ppm by vol. of $H_2O$.

Alternatively, it is also possible to use carbon monoxide 3.0 from GCH Gerling Holz & Handels GmbH having the specifications (the figures relate to the gas phase)
≥99.9% by vol. of CO,
≤700 ppm by vol. of $N_2$,
≤50 ppm by vol. of $O_2$,
≤50 ppm by vol. of Ar,
≤200 ppm by vol. of $H_2$,
≤50 ppm by vol. of $CO_2$,
≤25 ppm by vol. of hydrocarbons (total), and
≤20 ppm by vol. of $H_2O$.

In addition, the raw material used for the process according to the invention may be ethylene oxide 3.0 (reduced nitrogen) from GCH Gerling Holz & Handels GmbH, which has the specifications
≥99.9% by wt. of ethylene oxide,
≤60 ppm by wt. of $H_2O$,
≤20 ppm by wt. of acid (as acetic acid),
≤50 ppm by wt. of aldehyde (as acetaldehyde), and
≤0.1% by wt. of inert gas dissolved in the liquid phase
(the figures are based on the liquid phase). Any residual aldehyde content in the ethylene oxide can be made to disappear entirely prior to the inventive use thereof by treatment thereof with aldehyde scavengers (for example aminoguanidine hydrogencarbonate) to be undertaken in a manner known per se.

The raw material used for the process according to the invention may also be ethylene oxide 3.0 with approx. 4-6 bar of nitrogen and ethylene oxide 3.0 with approx. 10 bar of nitrogen (from the same supplier) (this is ethylene oxide 3.0 which, for technical reasons, has been blanketed with nitrogen fractions).

Normally, in the case of a batchwise inventive carbonylation of the ethylene oxide, the procedure, appropriately in application terms, will be to first purge the reaction space of the autoclave with inert gas (for example Ar). Subsequently, under the inert gas atmosphere and at comparatively low temperature, the catalyst system, the aprotic solvent and the ethylene oxide will be added to the reaction space of the autoclave and the latter will be closed.

Preference is given to stirred operation of the reaction space. Thereafter, an appropriate pressure valve is used to inject an amount of carbon monoxide suitable for the purposes of the carbonylation into the reaction space of the autoclave.

Then the temperature in the reaction space is increased to the reaction temperature by external heating, and the reaction mixture in the autoclave is stirred, for example while maintaining the reaction temperature. If, in the course of the conversion, no further carbon monoxide is injected into the reaction space, the carbonylating conversion is generally stopped when the internal pressure in the reaction space has fallen to a value which no longer changes with time. By appropriate cooling, the temperature within the reaction space is lowered, the elevated internal pressure is subsequently released to atmospheric pressure, and the autoclave is opened, such that there is access to the product mixture A present in the reaction space thereof.

As already mentioned, the carbon monoxide, especially in the case of batchwise execution of the process according to the invention, is normally used in a superstoichiometric amount. In principle, however, the amount corresponding to the stoichiometry or else a substoichiometric amount of CO can also be used in the process according to the invention.

Based on the molar total amount of ethylene oxide conducted into the autoclave, with comparatively short reaction times (generally $\leq 0.1$ to 10 h, frequently $\geq 0.25$ to $\leq 5$ h), typically conversions of $\geq 90$ mol %, advantageously $\geq 95$ mol % or $\geq 98$ mol %, preferably $\geq 99$ mol % and more preferably $\geq 99.9$ mol % are achievable.

Normally, the product mixture A which results in the inventive carbonylation of ethylene oxide comprises the desired poly-3-hydroxypropionate in the dissolved state (portions of the poly-3-hydroxypropionate formed may possibly also already have precipitated).

By leaving product mixture A to stand and/or cooling it, at least portions of poly-3-hydroxypropionate can be made to precipitate therein and can be removed from product mixture A by using one or more mechanical separating operations (for example filtration and/or centrifugation in a filter or in a centrifuge as an element of separation zone A) (liquid phase remaining in each case (for example the filtrate or the serum) constitutes, for example, a portion of product mixture A in the context of the present application).

As an alternative or in addition, poly-3-hydroxypropionate can be removed from product mixture A or from a portion thereof by adding a precipitation liquid thereto in separation zone A, and this, optionally accompanied by an additional lowering of the temperature, forces further precipitation of poly-3-hydroxypropionate than the sole measure of lowering the temperature. Subsequently, the poly-3-hydroxypropionate thus precipitated can be removed again from the respective mixture by the use of one or more mechanical separating operations in an element of separation zone A. It is possible to proceed further in an appropriate manner with the remaining liquid phase (which comprises a further portion of product mixture A) (for example for the purpose of enhancing the yield of poly-3-hydroxypropionate removed) (the amount of precipitation liquid first added may in principle, however, already have been selected at a sufficient level that the desired target amount of poly-3-hydroxypropionate precipitates as early as the first precipitation step).

If further precipitation liquid is added thereto, this forms mixtures which in turn constitute a portion of the product mixture A with precipitation liquid added thereto.

Useful precipitation liquids of this kind normally include especially liquids whose polarity is lower or higher (preferably "much lower" or "much higher") than the generally moderate polarity of the aprotic solvent used for the inventive carbonylating conversion.

If the latter is, for example, diglyme (=bis(2-methoxyethyl)ether), the precipitation liquids of this kind used may, for example, be methanol, cyclohexane, n-heptane and/or tert-butyl methyl ether.

A disadvantage of poly-3-hydroxypropionate removed as described (from product mixture A) using aforementioned precipitation liquids is that it still comprises perceptible amounts of cobalt attributable to the catalyst system used for carbonylation.

These are disadvantageous in that they impair subsequent thermolysis of the poly-3-hydroxypropionate. If methanol is used as the precipitation liquid, ester formation additionally proceeds with terminal carboxyl groups of the poly-3-hydroxypropionate. In the course of later thermolysis thereof, this results in the formation of methyl acrylate as an unwanted by-product.

This can be remedied in accordance with the invention in a simple manner, for example, by using water and/or an aqueous solution as at least part of the precipitation liquid.

In other words, advantageously in accordance with the invention, it is possible to add water and/or an aqueous solution to the total amount of product mixture A or to one or more portions of product mixture A in order to precipitate poly-3-hydroxypropionate present dissolved in the portion of product mixture A or in the entirety of product mixture A. It will be appreciated that the temperature of the resulting aqueous mixture may additionally be lowered. It is also possible for the water or the aqueous solution already to have a comparatively low temperature on the respective addition. This temperature may, for example, be $\geq 0°$ C. and $\leq 25°$ C.

In principle, it is advantageous in accordance with the invention to undertake an addition of water and/or of an aqueous solution as an aqueous precipitation liquid to one or more portions of product mixture A and/or to the entirety of product mixture A in the presence of at least one oxidizing agent (for Co in oxidation states <+2), in order to precipitate poly-3-hydroxypropionate present in a portion of product mixture A or in the entirety of product mixture A.

For example, it is preferable in accordance with the invention to undertake the aforementioned addition in the presence of air and/or in the presence of a molecular oxygen-comprising gas other than air. As an alternative or in addition, it is possible to add one or more than one oxidizing agent, for example ozone, hydrogen peroxide, molecular oxygen, a perchlorate and/or an oxidizing acid, for example nitric acid and/or perchloric acid, to a portion of product mixture A, to the aqueous precipitation liquid itself, to the entirety of product mixture A and/or to the resulting mixture of a portion or the entirety of product mixture A and the aqueous precipitation liquid before, during and/or after the addition of the aqueous precipitation liquid.

Before the precipitating poly-3-hydroxypropionate is removed from the respective aqueous mixture by at least one mechanical separating operation (for example by filtration and/or centrifugation), the respective aqueous mixture will, appropriately in application terms, be mixed vigorously. As already stated, it is advantageous in accordance with the invention to treat the aqueous mixture, prior to the mechanical removal of the poly-3-hydroxypropionate, with molecular oxygen or with a molecular oxygen-comprising gas (for example air or mixtures of molecular oxygen and molecular nitrogen, CO, $CO_2$, noble gas and/or steam). This can be accomplished in a simple manner by flow of molecular oxygen or of the molecular oxygen-comprising gas through the vigorously mixed aqueous mixture. It is also possible to saturate the water or an aqueous solution with molecular oxygen prior to the use thereof as a precipitation liquid for use in accordance with the invention. In a corresponding manner, it is also possible to enrich or saturate the entirety of product mixture A or the corresponding portion of product mixture A with molecular oxygen prior to the addition of an inventive aqueous precipitation liquid to this entirety or portion.

It will be appreciated that the treatment of the aqueous mixture with molecular oxygen or with a molecular oxygen-comprising gas (for example air or mixtures of molecular oxygen and molecular nitrogen) can also be performed at elevated temperature. This may, for example, be 10 to 95° C., or 20 to 95° C., or 30 to 95° C., advantageously 40 to 90° C. and particularly advantageously 50 to 80° C. or 50 to 60° C. In general, treatment times of a few minutes are adequate. Subsequently, the aqueous mixture can be cooled to temperatures of ≤25° C., preferably ≤20° C. and more preferably ≤15° C. or ≤10° C., in order to promote the precipitation of the poly-3-hydroxypropionate. Finally, the precipitated poly-3-hydroxypropionate can be removed from the aqueous mixture by at least one mechanical separating operation. It will be appreciated that the removal of precipitated poly-3-hydroxypropionate can also be undertaken in the hot aqueous mixture.

Poly-3-hydroxypropionate removed from product mixture A in such a way has a significantly reduced to vanishingly small cobalt content (this is of course correspondingly true of the respective overall content of the different possible individual oxidation states of Co, i.e. of the total content of $Co^{+2}$, and of $Co^{+1}$, and of $Co^{0}$, and of $Co^{-1}$). It can, for example, be subjected to further washing with methanol, then dried under the action of heat and finally subjected to the intended thermolysis to acrylic acid.

The above is especially true when the aqueous solution used as the precipitation liquid is one whose pH at a temperature of 25° C. and at standard pressure is ≤7.5, advantageously ≤7. The aforementioned pH of the aqueous precipitation liquid is preferably ≤6, and more preferably ≤5, and most preferably ≤4. In general, the aforementioned pH of the aqueous precipitation liquid will not go below the value of 0 and will in many cases be ≥1 or ≥2. Advantageously in accordance with the invention, the above pH values (likewise based on 25° C. and standard pressure) also apply to the aqueous mixtures which result in the case of addition of the aqueous precipitation liquid to product mixture A or to a portion of product mixture A, which optionally, advantageously in accordance with the invention, are treated with a molecular oxygen-comprising gas, and from which the precipitated poly-3-hydroxypropionate is removed by the use of at least one mechanical separating operation. The pH (25° C., standard pressure) of these aqueous mixtures is preferably 2 to 4, for example 3.

The pH values stated in this document relate, unless explicitly stated otherwise, to a determination with a Checker® pH electrode HI 98103 from HANNA Instruments Deutschland GmbH, D-77694 Kehl. Appropriately in application terms, the latter is calibrated before any measurement with the aid of two aqueous buffer solutions, the pH values of which under the corresponding conditions are, for example, 7.01 and 4.01 (technical buffers, model TEP 7 (catalog number 108702) and TEP 4 (catalog number 108700) from WTW (Wissenschaftlich Technische Werkstätten GmbH) in D-82362 Weinheim). For pH values above 7, the calibration can also be performed with the aid of other aqueous buffer solutions.

Useful modifiers for establishing the relevant pH include inorganic and/or organic acids (in the Brønsted sense). Examples include sulfuric acid, carbonic acid, hydrochloric acid and/or phosphoric acid as possible inorganic acids. Preference is given in accordance with the invention to using organic carboxylic acids, especially alkanecarboxylic acids, as pH modifiers. Examples of these include acrylic acid, oxalic acid, formic acid, acetic acid, propionic acid, fumaric acid and/or maleic acid. It will be appreciated that it is also possible to establish the relevant pH using, or partly using, organic sulfonic acids, for example methanesulfonic acid.

Aqueous precipitation liquids suitable in accordance with the invention thus include, for example, aqueous solutions comprising one or more than one of the aforementioned inorganic and/or organic acids. Such aqueous precipitation liquids are, for example, aqueous sulfuric acid, aqueous carbonic acid, aqueous hydrochloric acid, aqueous phosphoric acid, aqueous acrylic acid, aqueous oxalic acid, aqueous formic acid, aqueous acetic acid, aqueous propionic acid, aqueous fumaric acid, aqueous maleic acid and/or aqueous methanesulfonic acid. It will be appreciated that the addition of water and of one or more acids for the purpose of precipitation of poly-3-hydroxypropionate can also be effected with separation in terms of time and/or place, such that the effectively added acidic aqueous precipitation liquid, for example, is not formed until within the aqueous mixture comprising poly-3-hydroxypropionate.

Appropriately in application terms, one of the aforementioned aqueous precipitation liquids useable in accordance with the invention, based on the weight of the aqueous liquid, comprises at least 10% by weight, better at least 20% by weight or at least 30% by weight, advantageously at least 40% by weight or at least 50% by weight, particularly advantageously at least 60% by weight or at least 70% by weight, optionally at least 80% by weight or at least 90% by weight, in many cases at least 95% by weight or at least 97% by weight, or at least 99% by weight, of water.

In principle, the addition of a precipitation liquid to the entirety of a product mixture A and/or to a portion of a product mixture A can be effected in portions and at elevated temperature, such that only by subsequent gradual cooling in each case is the (further) crystallization or precipitation brought about. In this way, the total number of "precipitation seeds (crystallization seeds)" can be kept low, the ultimate result of which is a coarser quality of the precipitated poly-3-hydroxypropionate, the removal of which is subsequently possible in a comparatively simpler manner.

It will be appreciated that the precipitation of poly-3-hydroxypropionate from product mixture A or from a portion of product mixture A, in the context of the inventive procedure, can also be brought about by lowering the temperature thereof and/or by the addition of a nonaqueous precipitation liquid thereto (for example by addition of methanol, cyclohexane, n-heptane and/or tert-butyl methyl ether as the precipitation liquid).

In this case, the precipitated poly-3-hydroxypropionate is subsequently removed by at least one mechanical separating operation (for example filtration and/or centrifugation), and the cobalt content of the poly-3-hydroxypropionate thus removed, in accordance with the invention, is lowered or made vanishingly small by later washing thereof with water and/or an aqueous solution.

Useful aqueous solutions for the purpose of such a wash are especially all of those which have also already been listed and recommended as possible aqueous precipitation liquids. The preferences expressed for use as an aqueous precipitation liquid apply correspondingly with regard to use as aqueous wash solutions (as aqueous wash liquids).

In other words, aqueous solutions preferred in accordance with the invention as wash liquids are those whose pH at a temperature of 25° C. and at standard pressure is ≤7.5, advantageously ≤7. The aforementioned pH of the aqueous wash liquid (of the aqueous wash solution) is preferably ≤6, more preferably ≤5 and most preferably ≤4. In general, the aforementioned pH of an aqueous wash liquid (of an aqueous wash solution) will not go below the value of 0 and will in many cases be ≤1 or ≥2.

Useful modifiers for adjusting the pH of an aqueous wash solution include the inorganic and/or organic acids (in the Brønsted sense) already listed in connection with the corresponding aqueous precipitation liquids.

Examples include sulfuric acid, carbonic acid, hydrochloric acid and/or phosphoric acid as possible inorganic acids. Preference is given in accordance with the invention to using organic carboxylic acids, especially alkanecarboxylic acids, as such pH modifiers. Among these, acrylic acid, oxalic acid, formic acid, acetic acid, propionic acid, fumaric acid and/or maleic acid are mentioned by way of example. It will be appreciated that the relevant pH can also be established using, or partly using, an organic sulfonic acid, for example methanesulfonic acid.

Aqueous wash liquids suitable in accordance with the invention thus include, for example, aqueous solutions comprising one or more than one of the aforementioned inorganic and/or organic acids in dissolved form. Such aqueous wash liquids are, for example, aqueous sulfuric acid, aqueous carbonic acid, aqueous hydrochloric acid, aqueous phosphoric acid, aqueous acrylic acid, aqueous oxalic acid, aqueous formic acid, aqueous acetic acid, aqueous propionic acid, aqueous fumaric acid, aqueous maleic acid and/or aqueous methanesulfonic acid.

Appropriately in application terms, one of the aforementioned aqueous wash liquids for use in accordance with the invention, based on the weight of the aqueous wash liquid, comprises at least 10% by weight, better at least 20% by weight or at least 30% by weight, advantageously at least 40% by weight or at least 50% by weight, particularly advantageously at least 60% by weight or at least 70% by weight, optionally at least 80% by weight or at least 90% by weight, in many cases at least 95% by weight, or at least 97% by weight, or at least 99% by weight, of water. Water itself is not just a precipitation liquid suitable in accordance with the invention, but also a wash liquid suitable in accordance with the invention.

In the case of washing of poly-3-hydroxypropionate removed from product mixture A in separation zone A with water and/or with an aqueous solution as the aqueous wash liquid, it is also advantageous in accordance with the invention to undertake the washing in the presence of at least one oxidizing agent (for Co in oxidation states <+2). For example, it is advantageous to undertake the washing in the presence of air and/or in the presence of a molecular oxygen-comprising gas. As an alternative or in addition, one or more than one oxidizing agent, for example ozone, hydrogen peroxide, molecular oxygen, a perchlorate and/or an oxidizing acid, for example nitric acid and/or perchloric acid, can be added to the aqueous wash liquid and/or to the poly-3-hydroxypropionate to be washed prior to and/or during the wash.

Advantageously in accordance with the invention, the aqueous wash liquids listed above, prior to the use thereof for washing of cobalt-comprising poly-3-hydroxypropionate removed from a product mixture A, are therefore saturated, for example, with molecular oxygen.

In such an embodiment, the wash of the cobalt-comprising poly-3-hydroxypropionate removed from a product mixture A can be effected by forcing or sucking the aqueous wash liquid through the poly-3-hydroxypropionate (present, for example, on a filter as a filtercake, or on a solid centrifuge as a solid cake).

The temperature of the aqueous wash liquid may, for example, be 10 to 95° C., or 20 to 90° C., or 30 to 80° C., or 40 to 70° C., or 50 to 60° C. The temperature of the wash liquid is preferably selected such that the melting point of the poly-3-hydroxypropionate is not exceeded.

Alternatively, the cobalt-comprising poly-3-hydroxypropionate removed from a product mixture A, for the purpose of washing thereof with an aqueous wash liquid, can also be resuspended therein. In this case, it is found to be advantageous in accordance with the invention to additionally treat the resulting aqueous suspension of poly-3-hydroxypropionate with a molecular oxygen-comprising gas (for example air or mixtures of molecular oxygen and molecular nitrogen, CO, $CO_2$, noble gas and/or steam).

This can be accomplished in a simple manner by vigorously mixing the aqueous suspension and by additional flow of molecular oxygen or of a molecular oxygen-comprising gas (for example air) through it. Here too, the water or the aqueous solution, prior to the use thereof as a wash liquid for use in accordance with the invention, can be saturated with molecular oxygen. The temperature of the aqueous suspension of the poly-3-hydroxypropionate in the case of the procedure described may, for example, be 10 to 95° C., or 20 to 90° C., or 30 to 80° C., or 40 to 70° C., or 50 to 60° C. Optionally, the aqueous suspension may be converted to a solution or emulsion in the case of washing at an elevated temperature. Subsequent cooling thereof in these cases can result in reformation of the suspension. As the conclusion of the wash, the poly-3-hydroxypropionate (optionally on completion of cooling of the aqueous mixture) can be removed again from the aqueous suspension by at least one mechanical separating operation (for example filtration and/or centrifugation).

It will be appreciated that the described inventive aqueous wash of poly-3-hydroxypropionate removed from a product mixture A can be repeated more than once in order to remove the cobalt present therein (for example quantitatively). This statement does not just apply with regard to the total amount of Co present therein. Instead, it also applies in each case to the respective total amount of Co present therein in its possible individual oxidation states. In other words, it applies to the total amount of $Co^{2+}$ present therein, to the total amount of $Co^{+1}$ present therein, to the total amount of $Co^0$ present therein, and to the total amount of $Co^{-1}$ present therein.

It is also possible in accordance with the invention to employ the described inventive aqueous wash of poly-3-hydroxypropionate removed from a product mixture A with water and/or with one of the aqueous solutions when the removal of the poly-3-hydroxypropionate from product mixture A has already been undertaken with addition of water and/or of an aqueous solution as the aqueous precipitation liquid to one or more portions of product mixture A or to the entirety of product mixture A.

The amounts of aqueous precipitation liquid and/or aqueous wash liquid to be used in accordance with the invention, and the contents of inorganic and/or organic acids optionally to be established therein, are, appropriately in application terms, selected such that no cobalt salt is precipitated under the conditions employed for the respective precipitation.

More preferably in accordance with the invention, the aqueous precipitation liquid and/or the aqueous wash liquid used is an aqueous acetic acid solution and/or an aqueous formic acid solution, very particular preference being given to the use of an aqueous acetic acid solution due to the elevated solubility of cobalt acetate in aqueous (acetic acid) solutions.

In principle, in the process according to the invention, the aqueous solutions used as aqueous precipitation liquids and/or aqueous wash liquids may also be those whose pH (based on 25° C. and standard pressure) is >7.5 (for example the aqueous solution of at least one Brønsted base). In particular, mention is made in this regard of a precipitation and/or wash with an aqueous ammonia solution. However, this procedure is less preferred in accordance with the invention. It is also possible for aqueous precipitation and wash liquids to be used in accordance with the invention to comprise added complexing agents (especially chelating agents), for example ethylenediaminetetraacetic acid and/or one of the alkali metal salts thereof (for example one of the sodium salts thereof), these being able to complex cations of cobalt.

It will be appreciated that aqueous precipitation liquids and/or aqueous wash liquids suitable in accordance with the invention also include those aqueous solutions which, instead of or in addition to inorganic and/or organic (Brønsted) acids (especially those mentioned individually in this document), comprise at least one water-soluble organic solvent, for example alcohols (e.g. methanol, ethanol etc.), ketones (e.g. acetone, methyl ethyl ketone), amides (e.g. N,N-dimethylformamide and formamide), sulfoxides (e.g. dimethyl sulfoxide), N-methyl-2-pyrrolidone or cyclic ethers (e.g. tetrahydrofuran and 1,4-dioxane) in dissolved form. In general, the water content of such aqueous solutions, based on the total content thereof, will correspondingly be at least 10% by weight, or at least 20% by weight, or at least 30% by weight, or at least 40% by weight, or at least 50% by weight, or at least 60% by weight, or at least 70% by weight, or at least 80% by weight, or at least 90% by weight, or at least 95% by weight or at least 97% by weight, or least 99% by weight.

Generally, in accordance with the invention, further washing of the poly-3-hydroxypropionate with, for example, water and/or (more preferably) methanol is advisable.

Such further washing can eliminate the last unwanted constituents from the poly-3-hydroxypropionate. Further washing with methanol additionally facilitates subsequent drying of the comparatively pure poly-3-hydroxypropionate. The latter can be effected, for example, over several hours (for example overnight) at temperatures of 50 to 90° C., preferably 50 to 60° C., for example in a drying cabinet. It can also be performed under reduced pressure and/or at comparatively lower temperature. Such a drying operation is preferably effected at temperatures at which the melting point of the poly-3-hydroxypropionate is not yet exceeded.

It will be appreciated that, in the process according to the invention, such a drying operation may also be omitted. In this case, any residual moisture present in the P3HP volatilizes in the course of the heating required for the thermolysis thereof (normally before the thermolysis sets in).

One reason for the efficacy of the inventive precipitation and/or wash with water and/or aqueous solutions is probably that, in the course of the inventive carbonylating conversion, polyester chains of the following structure are formed (cf. J. Am. Chem. Soc., 2002, 124, page 5646-5647):

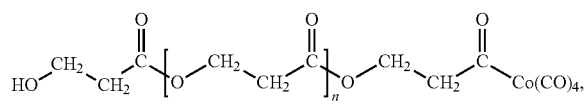

where n is an integer ≥1, and may be up to 150, or up to 200, or up to 250 or more. The left-hand end reflects the start of the chain and the right-hand end reflects the chain growth. Water is able to split the right-hand chain end to form

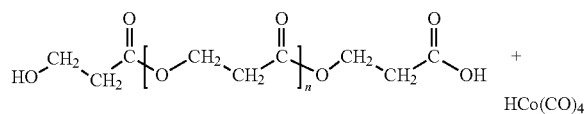

$HCo(CO)_4$ by hydrolysis, and to terminate the polyester chain in this way. Presence of molecular oxygen (or generally of an oxidizing agent) promotes the formation of Co2+, the solubility of which in aqueous solutions is comparatively elevated.

Furthermore, a combination of water/oxidizing agent or aqueous solution/oxidizing agent (e.g. O2) probably also acts correspondingly, in the inventive manner, on compounds of cobalt present merely in an absorbed form in the poly-3-hydroxypropionate removed.

The inventive removal of poly-3-hydroxypropionate for product mixture A prepared in accordance with the invention is thus able, in a comparatively efficient manner, to provide poly-3-hydroxypropionate with as low a cobalt content as desired (including cobalt contents beyond the cobalt detection limit) for an inventive thermolysis of the poly-3-hydroxypropionate. This statement applies not just with regard to the total amount of Co present in the poly-3-hydroxypropionate to be split in accordance with the invention. Instead, it also applies to the respective total amount of Co present therein (in the poly-3-hydroxypropionate to be split by inventive thermolysis) in the possible individual oxidation states thereof. In other words, it applies to the total amount of $Co^{2+}$ present therein, to the total amount of $Co^{+1}$ present therein, to the total amount of $Co^{0}$ present therein, and to the total amount of $Co^{-1}$ present therein.

For example, the cobalt content of the poly-3-hydroxypropionate (based on the total weight thereof) in the inventive thermolysis thereof may be ≤2% by weight, or ≤1% by weight, or ≤0.5% by weight or ≤0.1% by weight or ≤0.05% by weight, or ≤0.01% by weight, or ≤0.001% by weight, or ≤$10^{-4}$% by weight, or ≤$10^{-5}$% by weight, or ≤$10^{-6}$% by weight (or may lie beyond the detection limit).

The above statement and numerical contents cited individually apply not just with regard to the total amount of Co possibly present in the poly-3-hydroxypropionate to be split in accordance with the invention. Instead, they also apply in each case to the respective total amount of Co present therein (in the poly-3-hydroxypropionate to be split by inventive thermolysis) in one of the individual possible oxidation states thereof. In other words, they also apply individually to the total amount of $Co^{2+}$ possibly present therein (in the poly-3-hydroxypropionate to be split by inventive thermolysis), to the total amount of $Co^{+1}$ possibly present therein, to the total amount of $Co^{0}$ possibly present therein, and to the total amount of $Co^{-1}$ possibly present therein.

The lower the (total) cobalt content of the poly-3-hydroxypropionate, the lower the disruptive effect of the Co in the thermolysis of poly-3-hydroxypropionate (this is especially true of Co present in an oxidation state <+2). In industrial practice, however, the total expenditure to be applied in the course of an inventive decobaltation of the poly-3-hydroxypropionate will normally be restricted to economic reasons such that the (total) cobalt content of the poly-3-hydroxypropionate remaining for the thermolysis still appears tolerable from an overall economic point of view.

In this context, the (total) cobalt content of poly-3-hydroxypropionate obtained in accordance with the invention, in the inventive thermolysis thereof, and based on the total weight thereof, may, for example, be 0% by weight to 1% by weight, or $10^{-6}$% by weight to 1% by weight, or $10^{-5}$% by weight to 1% by weight, or $10^{-4}$% by weight to 1% by weight, or 0.001% by weight to 0.75% by weight, or 0.01% by weight to 0.75% by weight, or 0.05% by weight to 0.75% by weight, or 0.1% by weight to 0.5% by weight.

The above statement and numerical content ranges stated individually apply not just with regard to the total amount of Co possibly present in the poly-3-hydroxypropionate to be split in accordance with the invention. Instead, they also apply in each case to the respective total amount of Co present therein (in the poly-3-hydroxypropionate to be split by inventive thermolysis) in the possible individual oxidation state thereof. In other words, they also apply individually to the total amount of $Co^{2+}$ possibly present therein (in the poly-3-hydroxypropionate to be split by inventive thermolysis), to the total amount of $Co^{+1}$ possibly present therein, to the total amount of $Co^0$ possibly present therein, and to the total amount of $Co^{-1}$ possibly present therein.

It is known from the prior art that poly-3-hydroxypropionate can be split to acrylic acid by the sole action of elevated temperature (cf. U.S. Pat. No. 2,568,636 A, U.S. Pat. No. 2,361,036 A and EP 577206 A2), and this thermolytic splitting is normally executed in the substantial absence of molecular oxygen.

Due to this property, poly-3-hydroxypropionate constitutes a particularly advantageous depot form (storage form)/transport form of acrylic acid which, in contrast to acrylic acid itself, is essentially not subject to any aging process (under standard conditions (=25° C. and standard pressure), liquid acrylic acid, when left to stand, for example, ages in an unavoidable manner as a result of unwanted Michael addition of acrylic acid to itself and to the addition products which form; unwanted free-radical polymerization of acrylic acid with itself forms a further aging pathway which typically has to be counteracted (for example for safety reasons) by addition of polymerization inhibitors to the acrylic acid; in the case of a free-radically initiated polymerization with partial use of such an acrylic acid comprising polymerization inhibitor, the polymerization inhibitor present therein can impair the free-radically initiated polymerization; moreover, polymerization inhibitors are comparatively expensive active compounds which additionally generally have to be renewed from time to time since the action thereof can be exhausted).

More particularly, poly-3-hydroxypropionate, which is generally in the solid state of matter under standard conditions, can be both stored and transported without any problems.

It is also known that the temperatures required for appropriate splitting rates can be considerably reduced by the addition of suitable splitting catalysts to the poly-3-hydroxypropionate to be split (or to a splitting mixture comprising the latter) (cf., for example, WO 2011/100608 and U.S. Pat. No. 2,961,036 A).

Splitting temperatures to be employed in a typical manner may therefore vary within the range from 50 to 350° C. or within the range from 100 to 300° C. Preferably in application terms, typical splitting temperatures are 150 to 220° C. and more preferably 160 to 200° C.

According to the melting point and solubility of the poly-3-hydroxypropionate, the thermal splitting thereof to acrylic acid can be effected from the solid substance thereof, or from the melt thereof, or from the solution thereof in a solvent, or from the suspension thereof in an organic liquid (a dispersant), or from the emulsion thereof in an organic liquid (a dispersant). The boiling point (based on standard pressure) of such a solvent/dispersant is, advantageously in application terms, distinctly (for example at least 20° C., better at least 40° C., even better at least 50° C. or at least 60° C., preferably at least 80° C. and more preferably at least 100° C.) above the corresponding boiling temperature of acrylic acid (=141° C.). For example, useful solvents/dispersants of this kind also include ionic liquids.

The working pressure during the thermal splitting of poly-3-hydroxypropionate may either be standard pressure ($=1.0133 \cdot 10^5$ Pa) or above or below standard pressure.

If the working pressure is below standard pressure (for example at pressures down to $10^2$ Pa or less), the acrylic acid formed in the splitting follows the pressure gradient present and is withdrawn continuously from the liquid splitting mixture in this manner.

If the working pressure is at or above standard pressure (for example at pressures up to $10^7$ Pa or more), the acrylic acid formed in the splitting, appropriately in application terms, can be continuously stripped out of the splitting mixture, for example in liquid form (which may, for example, also be the exclusive melt of the P3HP), with the aid of a stripping gas (for example molecular nitrogen, noble gas, carbon dioxide, air, lean air (preferred; molecular oxygen-depleted air (generally <6% by vol. of $O_2$))).

The measure of stripping can also be partly employed in the context of splitting under reduced pressure.

It will be appreciated that the acrylic acid formed in the course of splitting can also be distilled out of the splitting mixture, for example in liquid form, in a conventional manner following the corresponding temperature gradient.

If the gas stream which comprises the acrylic acid formed in the splitting and is flowing away from the splitting mixture, for example in liquid form, is conducted in countercurrent to descending reflux liquid through a rectification column on top of the (or a) splitting reactor, the acrylic acid can be removed in elevated purity from the liquid splitting mixture.

All such splitting operations on poly-3-hydroxypropionate by the action of elevated temperatures are summarized in this document by the term "thermolysis" or "pyrolysis" of poly-3-hydroxypropionate.

All splitting processes known from the prior art for poly (3-hydroxypropionic acid) can be applied correspondingly to poly-3-hydroxypropionate obtainable in accordance with the invention. Typical working pressure ranges are $10^2$ to $10^7$ Pa, often $10^3$ to $10^6$ Pa, in many cases $2 \cdot 10^3$ to $5 \cdot 10^5$ Pa or $5 \cdot 10^3$ to $3 \cdot 10^5$ Pa.

The melting point of poly-3-hydroxypropionate obtainable in accordance with the invention at standard pressure is normally $\geq 50°$ C. and $\leq 150°$ C., usually $\leq 100°$ C.

Against this background, it is appropriate in accordance with the invention to perform the thermolysis of a poly-3-hydroxypropionate obtainable in accordance with the invention to acrylic acid from the melt thereof.

In this case, it would be desirable to be able to perform the thermolysis in the presence of at least one splitting catalyst which dissolves completely under the conditions of the splitting process (working pressure, splitting temperature) with the catalytically active amount thereof to be added which is required in each case in the melt of the poly-3-hydroxypropionate to be thermally split ("first requirement").

Additional use of splitting catalysts does not just enable performance of the thermolysis at lower temperatures but also normally ensures, under given thermolysis conditions, especially also an elevated space-time yield of acrylic acid (under given conditions, the splitting catalyst generally improves both the splitting rate and the selectivity of target product formation (of acrylic acid formation)).

In the given context, it would be further advantageous if the at least one splitting catalyst is an active substance (active compound) whose boiling point at standard pressure is additionally at least 180° C., preferably at least 185° C. and more preferably at least 190° C. ("second requirement").

The reason for the additional advantage is that such splitting catalysts, in the course of the thermolysis of the poly-3-hydroxypropionate that they catalyze, normally need not necessarily be discharged from the splitting mixture with the acrylic acid formed in the splitting, but may generally remain in the splitting mixture (the latter can be promoted, for example, by a rectification column on top of the splitting reactor, operated under reflux). Successive addition of fresh P3HP to be split to the splitting mixture in this case makes it possible to make multiple (repeated) use of the effect of one and the same splitting catalyst addition.

An additional advantageous ("second requirement*") upper boiling point limit for an active compound suitable in accordance with the invention as a splitting catalyst for the thermolysis (i.e. a boiling point at standard pressure of ≤350° C., preferably ≤345° C., better ≤340° C., advantageously ≤335° C., particularly advantageously ≤330° C. or ≤325° C., very particularly advantageously ≤320° C. or ≤315° C., even better ≤310° C., and at best ≤300° C., or ≤290° C., or ≤280° C., or ≤270° C., or ≤260° C., or ≤250° C. or ≤240° C., or ≤230° C., or ≤200° C.) additionally opens up the possibility, after splitting has ended (after thermolysis has ended), of removing an active compound used in accordance with the invention as part of the splitting catalyst subsequently from residues which generally remain in the inventive thermolysis, for example by distillation and/or rectification, optionally at elevated temperature and/or under reduced pressure, and thus of obtaining it as a product of value in reutilizable form, for example for an inventive thermolysis process. If such a removal is not undertaken, in accordance with the invention, active compounds useable as a splitting catalyst should enable disposal of splitting residues by, for example, energy-supplying full combustion thereof, without any risk of the formation of particularly critical combustion gases originating from any active compound used.

In addition, it would be advantageous if the melting point of the at least one active substance (at least one active compound) used as the splitting catalyst at standard pressure is additionally ≤70° C., preferably ≤60° C., more preferably ≤50° C., even more preferably ≤40° C. and at best ≤25° C. ("third requirement").

A splitting catalyst which fulfills not only the first and second requirements but also the third requirement is advantageous in that it normally melts at a lower temperature than the poly-3-hydroxypropionate to be split itself and as a result can possibly function as a solvent or as a dispersant to the poly-3-hydroxypropionate to be split. In the extreme case, the thermolysis of the poly-3-hydroxypropionate can be effected from the solution thereof, or from the suspension thereof, or from the emulsion thereof in the splitting catalyst.

It is additionally advantageous when an active substance to be used as a splitting catalyst additionally fulfills the following requirements:
  a comparatively low dynamic viscosity of the melt of the splitting catalyst under the conditions of the thermolysis ("fourth requirement");
  the melt of the splitting catalyst is capable of good wetting of solid poly-3-hydroxypropionate ("fifth requirement"); and
  the flashpoint of the active substance is at a maximum temperature ("sixth requirement").

In addition, an active substance for use as a splitting catalyst in accordance with the invention should fulfill the basic requirement of maximum mass-specific catalytic action. In other words, a minimum use mass of the active substance (of the active compound) should be sufficient to display the desired catalytic action.

In-house studies by the applicant have led to the result that the basic requirement and with it generally also the first requirement are met by organic active molecules or molecular organic active compounds (molecular organic (active) substances; "molecular" means here explicitly that the organic active compound is not a salt, not an ionic compound, and thus does not include, for example, quaternary ammonium compounds) which have, as well as carbon and hydrogen, in covalently bonded form, as heteroatoms other than these, at least one nitrogen atom and optionally at least one or more than one oxygen atom, with the proviso that
  the active molecule (the (active) substance) does not have any heteroatom other than carbon and hydrogen over and above nitrogen and oxygen, and
  at least one nitrogen atom is a tertiary nitrogen atom.

These active compounds preferably do not have any nitrogen atom to which one or more than one hydrogen atom is covalently bonded. In addition, these active compounds advantageously do not have any oxygen atom to which a hydrogen atom is covalently bonded.

A tertiary nitrogen atom shall be understood in this document to mean a nitrogen atom which has covalent chemical bonds only to carbon atoms, where the total number of these carbon atoms is not more than three and is at least two, and none of these carbon atoms at the same time has a covalent chemical double bond to an oxygen atom. The amount of such tertiary nitrogen atoms includes especially, for example, "iminic" nitrogen atoms, as possessed, for example, by pyridine and 3-hydroxypyridine.

The aforementioned is especially true when the molar mass M of the molecular organic active substance is ≥59.1 g/mol and ≤600 g/mol, preferably ≥75 g/mol and ≤500 g/mol, more preferably ≥100 g/mol and ≤400 g/mol, better ≥125 g/mol and ≤300 g/mol, and most preferably ≥150 g/mol and ≤250 g/mol, or ≤200 g/mol.

An elevated mass-specific catalytic splitting action of the molecular organic active substance is generally present when it has more than one tertiary nitrogen atom (for example at least two or at least three tertiary nitrogen atoms).

It is also favorable in accordance with the invention for an elevated mass-specific catalytic splitting action when at least one tertiary nitrogen atom of the organic active substance has covalent chemical bonds to three different carbon atoms (to not more and not less than these three and also to no other atom).

Preferably in accordance with the invention, the relevant molecular organic active substance comprises at least two and most preferably at least three tertiary nitrogen atoms, each of which has covalent chemical bonds to three different carbon atoms.

Most preferably, the relevant active substance comprises only nitrogen atoms which are tertiary nitrogen atoms and preferably such tertiary nitrogen atoms that each of these nitrogen atoms has covalent chemical bonds to three different carbon atoms in each case.

Among the above-detailed molecular organic active compounds suitable as inventive splitting catalysts, emphasis should therefore be given, inter alia, to those which can be derived formally from ammonia by replacing the three hydrogen atoms thereof with three alkyl groups.

Among these tertiary aliphatic amines, preference is given to those of the general formula I

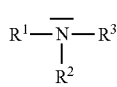

(I)

where $R^1$, $R^2$ and $R^3$=independently alkyl groups having 1 to 8 carbon atoms, preferably 1 to 6 carbon atoms and more preferably 1 to 4 carbon atoms (these groups are formed only from hydrogen and carbon atoms and do not include the cycloalkyl groups) or cycloalkyl groups (are likewise formed only from hydrogen and carbon).

Among the tertiary aliphatic amines of the general formula I, preference is given to those in which $R^1=R^2=R^3$ (and preferably=an alkyl group). Preferred $R^1$, $R^2$, $R^3$ radicals are the methyl group, the ethyl group, the isopropyl group, the n-propyl group, the n-butyl group, the tert-butyl group and the n-hexyl group, and also the cyclohexyl group.

Examples of active compounds of the general formula I include trimethylamine, triethylamine, tri-n-hexylamine, tri-n-butylamine and N-ethyl-N,N-diisopropylamine.

In addition, useful molecular organic active compounds of this kind as splitting catalysts advantageous in accordance with the invention (referred to later in this document as active compounds of the general formula II) are those which derive in a formal sense from the active compounds of the general formula (I) by virtue of at least one of the $R^1$, $R^2$, $R^3$ radicals being an alkyl or cycloalkyl group in which one or more than one hydrogen atom has been replaced by at least one of the groups —OH, —$NH_2$, —$NHCH_3$ and —$N(CH_3)_2$ and/or the (optionally cyclic) carbon chain has been interrupted at least once by an oxygen atom and/or a nitrogen atom. Two of these radicals, together with the tertiary nitrogen atom bearing them, may also form a cycle (a ring). Active compounds (II) preferably do not comprise any nitrogen atom to which one or more than one hydrogen atom is covalently bonded and/or any oxygen atom to which a hydrogen atom is covalently bonded.

Among the active compounds of the general formula (II), as splitting catalysts particularly suitable in accordance with the invention (for all thermolyses detailed in this (in the present) document, including those of all poly-3-hydroxypropionates splittable to give acrylic acid which are detailed in the present document), examples to which emphasis is given are pentamethyldiethylenetriamine (M=173.30 g/mol; b.p.=199° C.; m.p. <−20° C.; purchasable as Lupragen® N301 from BASF SE), N,N,N',N'-tetramethyl-1,6-hexanediamine (M=172.31 g/mol; b.p.=212° C.; m.p.=−46° C.; purchasable as Lupragen® N500 from BASF SE), bis(2-dimethyl-aminoethyl)ether (M=160.3 g/mol; b.p.=189° C.; m.p.=60° C.; purchasable as Lupragen® N205 from BASF SE), 2,2'-dimorpholinodiethyl ether (M=244.33 g/mol; b.p.=309° C.; m.p.=−28° C.; purchasable as Lupragen® N106 from BASF SE), N,N-diethylethanolamine (M=117.19 g/mol; b.p.=161° C.; m.p.=−70° C.), N,N,N',N'-tetramethyl-1,3-propanediamine (M=130.23 g/mol; b.p.=146° C.; m.p.=−78° C.), N,N-dimethylcyclohexylamine (M=127.23 g/mol; b.p.=159° C.; m.p.=−60° C.; purchasable as Lupragen® N100 from BASF SE) and N,N-dimethyl-1,3-diaminopropane (M=102.18 g/mol; b.p.=133° C.; m.p.=−60° C.).

Further relevant active compounds suitable as inventive splitting catalysts (active compounds III) are, for example, derivatives of 1,3-diazole (imidazole) in which the hydrogen on the nitrogen of the 1,3-diazole in the 1 position has been replaced by an alkyl group $R^4$ having 1 to 8 carbon atoms, preferably 1 to 6 carbon atoms and more preferably 1 to 4 carbon atoms. Optionally, the hydrogen on one of the carbon atoms in the diazole ring may additionally be replaced by an alkyl group $R^5$ having 1 to 8 carbon atoms, preferably 1 to 6 carbon atoms and more preferably 1 to 4 carbon atoms.

Examples of active compounds III include N-methylimidazole (M=82.12 g/mol; b.p.=198° C.; m.p.=−2° C.; purchasable as Lupragen® NMI from BASF SE) and 1,2-dimethylimidazole (M=96.13 g/mol; b.p.=204° C.; m.p.=38° C.).

Among the molecular organic active compounds listed above by way of example as splitting catalysts particularly suitable in accordance with the invention, pentamethyldiethylenetriamine is preferred once again (especially for all thermolyses detailed in this (in the present) document, including those of all poly-3-hydroxypropionates splittable to give acrylic acid which are detailed in the present document), since it particularly advantageously combines the desired properties of a splitting catalyst favorable in accordance with the invention.

Further active compounds according to the definition which are of particular interest as splitting catalysts suitable in accordance with the invention are the hydroxypyridines (2-hydroxypyridine, 3-hydroxypyridine and 4-hydroxypyridine).

This is especially also because they, as already mentioned, also constitute cocatalysts suitable for the inventive carbonylating conversion of ethylene oxide to poly-3-hydroxypropionate. In general, in the inventive removal of the poly-3-hydroxypropionate from product mixture A, such cocatalyst C (for example 3-hydroxypyridine), and/or possibly also cocatalyst B, remains (at least) partly in the poly-3-hydroxypropionate removed (for example absorbed therein), such that, in the course of thermolysis thereof, a separate addition of additional splitting catalyst(s) can be dispensed with, since, for example, the cocatalyst C compound (for example the 3-hydroxypyridine) remaining in the poly-3-hydroxypropionate in the removal thereof has splitting catalytic action to a sufficient extent.

It is of particular significance in this context that, for example in the case of use of 3-hydroxypyridine as such a cocatalyst C, at least a portion of the 3-hydroxypyridine is covalently bonded as the head group to the polyester chain of the poly-3-hydroxypropionate, which leads, for example, to polyester chains of the following structures:

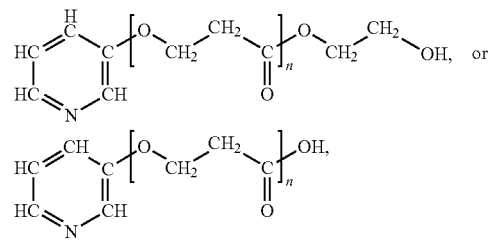

where n in each case is an integer of ≥1, and up to 150, or up to 200, or up to 250 or more.

In other words, poly-3-hydroxypropionate etherified with the hydroxyl group of 2-hydroxypyridine or of 3-hydroxypyridine or of 4-hydroxypyridine is formed.

This fact is remarkable in accordance with the invention because a 2-hydroxypyridine or 3-hydroxypyridine or 4-hydroxypyridine bonded covalently to the poly-3-hydroxypropionate in this way remains in the poly-3-hydroxypropionate (and is not also washed out) both in the case of an inventive aqueous precipitation thereof from, for example, a product mixture A and in the case of an inventive aqueous wash thereof after the removal thereof from a product mixture A. This is of essential significance in accordance with the invention because hydroxypyridine (e.g. 2-hydroxypyridine or 3-hydroxypyridine or 4-hydroxypyridine) chemically bound to poly-3-hydroxypropionate as the head group has not lost its ability to act as a splitting catalyst for the thermolysis of the poly-3-hydroxypropionate. This is also true with effect for poly-3-hydroxypropionate chains which do not have a corresponding hydroxypyridine chemically bonded as a head group.

Incidentally, catalytically active amounts of the described molecular organic active compounds suitable in accordance with the invention as splitting catalysts, based on the weight of the mass of poly-3-hydroxypropionate to be split, are generally 0.01 to 15% by weight or 0.05 to 10% by weight, often from 0.1 to 5% by weight, preferably 0.5 to 4% by weight, or 1.5 to 3.5% by weight.

Naturally, the use amount of splitting catalyst in the process according to the invention may also be above the aforementioned values. This is the case especially when the splitting catalyst functions simultaneously as a solvent or as a dispersant for the poly-3-hydroxypropionate to be split. Particularly in these cases, the use amounts of splitting catalyst on a corresponding basis may easily run to up to 50% by weight, or up to 100% by weight, or up to 150% by weight, or up to 200% by weight, or up to 250% by weight, or up to 300% by weight or more.

It will be appreciated that it is also possible for other, for example high-boiling organic, solvents or dispersants, for example ionic liquids, oligomeric (particularly di- to hexameric) Michael adducts (addition products) of acrylic acid to itself and to the adducts which form, as typically arise in the course of conventional preparation of acrylic acid (especially, for example, as bottom products in rectifications of acrylic acids), dimethyl sulfoxide, N-methyl-2-pyrrolidone, dialkylformamide, relatively long-chain paraffinic hydrocarbons, relatively long-chain alkanols, γ-butyrolactone, ethylene carbonate, diphenyl ether, diglyme, triglyme, tetraglyme, biphenyl, tricresyl phosphate, dimethyl phthalate and/or diethyl phthalate to be part of the splitting mixture comprising the poly-3-hydroxypropionate to be split and the generally at least one splitting catalyst. However, presence of solvent or dispersant under otherwise identical conditions generally reduces the splitting rate.

The proportion by weight of the poly-3-hydroxypropionate in such a splitting mixture also comprising solvent or dispersant may, based on the total weight of the splitting mixture, be less than 95% by weight, or less than 90% by weight, or less than 80% by weight, or less than 70% by weight, or less than 60% by weight, or less than 50% by weight, or less than 40% by weight, or less than 30% by weight, or less than 20% by weight, or less than 10% by weight. In general, this proportion by weight, however, is ≥5% by weight.

Irrespective of whether the poly-3-hydroxypropionate is present in the splitting mixture in the form of a melt thereof, or dissolved in a solvent, or dispersed in a dispersant as a suspension or emulsion, the at least one molecular organic active compound added as a splitting catalyst is preferably present dissolved in the splitting mixture (i.e. in the melt, in the solvent, or in the dispersant).

For reasons of melting point depression, it may also be appropriate to use more than one splitting catalyst, for example two or three different splitting catalysts.

In order to optionally counteract any unwanted free-radical polymerization of acrylic acid formed in the splitting mixture, appropriate polymerization inhibitors can additionally be added to the splitting mixture.

Useful polymerization inhibitors of this kind in principle include all of those which are recommended in the prior art for the purpose of inhibiting free-radical polymerization of acrylic acid in the liquid phase. Useful polymerization inhibitors of this kind include alkylphenols, such as o-, m- or p-cresol (methylphenol), 2-tert-butyl-4-methylphenol, 6-tert-butyl-2,4-dimethylphenol, 2,6-di-tert-butyl-4-methylphenol, 2-tert-butylphenol, 4-tert-butylphenol, 2,4-di-tert-butylphenol and 2-methyl-4-tert-butylphenol, hydroxyphenols such as hydroquinone, catechol, resorcinol, 2-methylhydroquinone and 2,5-di-tert-butylhydroquinone, aminophenols, for example para-aminophenol, nitrosophenols, for example para-nitrosophenol, alkoxyphenols such as 2-methoxyphenol, 2-ethoxyphenol, 4-methoxyphenol (hydroquinone monomethyl ether) and mono- or di-tert-butyl-4-methoxyphenol, tocopherols, for example α-tocopherol, N-oxyls such as 4-hydroxy-2,2,6,6-tetramethylpiperidine N-oxyl, 2,2,6,6-tetramethylpiperidine N-oxyl, 4,4',4''-tris(2,2,6,6-tetramethylpiperidine N-oxyl) phosphite or 3-oxo-2,2,5,5-tetramethyl-pyrrolidine N-oxyl, aromatic amines or phenylenediamines, for example N,N-diphenylamine, N-nitrosodiphenylamine and N,N'-dialkyl-para-phenylenediamine, where the alkyl radicals may be the same or different and each independently consist of 1 to 4 carbon atoms and may be traight-chain or branched, hydroxylamines, for example N,N-diethylhydroxylamine, phosphorus compounds, for example triphenylphosphine, triphenyl phosphite, hypophosphorous acid or triethyl phosphite, sulfur compounds, for example diphenyl sulfide or phenothiazine, and all aforementioned inhibitors optionally in combination with metal salts, for example the chlorides, dithiocarbonates, sulfates, salicylates or acetates of copper, manganese, cerium, nickel and/or chromium.

It is also possible to use different mixtures of the polymerization inhibitors mentioned. The polymerization inhibitors used are preferably phenothiazine and/or hydroquinone monomethyl ether. In addition, the aforementioned polymerization inhibitors can be supported by a molecular oxygen-comprising gas (for example air or nitrogen-diluted air (advantageously lean air)).

Appropriately in application terms, the explosion limits of gaseous mixtures comprising acrylic acid and oxygen are noted (cf., for example, WO 2004/007405 A1). For example, the above support can be effected by stripping the acrylic acid formed in the splitting continuously out of the splitting mixture with the aid of a molecular oxygen-comprising stripping gas (such a stripping operation can be effected at reduced pressure, standard pressure, or else at working pressures above standard pressure).

According to the polymerization inhibitor (or mixture of polymerization inhibitors) used, the use amount thereof, based on the content of poly-3-hydroxypropionate in the splitting mixture, will be 10 to 1000 ppm by weight, frequently 50 to 500 ppm by weight and in many cases 150 to 350 ppm by weight.

Otherwise, the splitting of the poly-3-hydroxypropionate obtainable in accordance with the invention can be effected as already explained in the acknowledgement of the known prior art splitting processes.

In other words, splitting temperatures to be typically employed (temperatures at which the thermolysis is performed) may be within the range from 50 to 350° C., or within the range from 100 to 300° C. Advantageously in accordance with the invention, the splitting temperatures employed will be 150 to 220° C. and more preferably 160 to 200° C.

Equally, the working pressure during the inventive thermolysis of the poly-3-hydroxypropionate (in the gas atmosphere) may be either standard pressure ($=1.0133 \cdot 10^5$ Pa) or above or below standard pressure. In other words, the working pressure may be $10^2$ to $10^7$ Pa, or $10^3$ to $10^6$ Pa, or $2 \cdot 10^3$ to $5 \cdot 10^5$ Pa, or $5 \cdot 10^3$ to $3 \cdot 10^5$ Pa.

The acrylic acid can be converted from the acrylic acid-comprising gas phase obtained in the thermolysis of the poly-3-hydroxypropionate removed in accordance with the invention to the liquid phase in a manner known per se, by absorptive and/or condensative measures. In general, this liquid phase may already be the acrylic acid which is obtainable in accordance with the invention and is suitable for further uses, for example free-radical polymerizations (especially when the acrylic acid thus obtained is not stored intermediately prior to the further use thereof in a free-radically initiated polymerization, the aforementioned conversion to the liquid phase will advantageously be undertaken without additional use of polymerization inhibitors which impair any (later) free-radically initiated polymerization).

With application of one or more thermal separation processes (such thermal separation processes are especially rectification, extraction, desorption, distillation, stripping, absorption, azeotropic rectification and/or crystallization) to the acrylic acid-comprising liquid phase, the acrylic acid from the liquid phase can be purified to any purity as required (for example analogously as described in documents DE 10243625 A1, DE 10332758 A1, DE 102007004960 A1 and DE 102012204436 A1, and the prior art cited in these documents).

A suitable preferred thermal separation process is the process of crystallization. Within the crystallizative separation processes, the process of suspension crystallization is preferentially employable for the aforementioned purpose (for example analogously as described in DE 102007043759 A1, DE 102008042008 A1 and DE 102008042010 A1, and the prior art cited in these documents).

The removal of the suspension crystals from the crystal suspension is, appropriately in application terms, undertaken in a wash melt wash column (cf. WO 01/77056 A1; the wash liquid used is the melt of acrylic acid crystals already purified correspondingly), preferably in a hydraulic wash melt wash column (analogously as described, for example, in WO 01/77056 A1, WO 02/09839 A1, WO 03/041832 A1, WO 2006/111565 A2, WO 2010/094637 A1 and WO 2011/045356 A1, and the prior art cited in these documents).

Incidentally, the inventive splitting of the poly-3-hydroxypropionate can be performed on the industrial scale either batchwise or continuously.

Appropriately in application terms, a continuous process regime (and with it a corresponding inventive thermolysis zone A) may be configured as follows. The splitting reactor used is the bottom space of a separating column comprising separating internals (useful separating internals include, for example, mass transfer trays such as dual-flow trays; in principle, the separating column may also be empty, i.e. not have any separating internals). The liquid splitting mixture (which may be a melt, a solution, a suspension or an emulsion) is supplied in the lower third of the separating column (in principle, the supply may also be effected directly into the bottom space; such a supply may in principle also be effected "in solid form").

Below the feed point (advantageously from the bottom space), by means of a pump, a liquid stream (which may optionally also be a suspension) is withdrawn continuously and recycled by means of an indirect heat exchanger back into the separating column below the feed point of the splitting mixture. In the course of flow through the indirect heat exchanger, the thermal energy required for the thermolysis is supplied. Advantageously in application terms, the indirect heat exchanger is a forced circulation flash heat transferer.

At the top or via a side draw, the acrylic acid can be conducted out of the separating column. If the separating column has separating internals, condensate formation is brought about in the top region of the separating column and a portion of the condensate formed is conducted descending as reflux liquid in countercurrent to the acrylic acid ascending in the separating column (for example conducted by a stripping gas and/or following the pressure gradient in the case of reduced top pressure). As an outlet for the highest-boiling secondary components, a portion of the bottoms liquid is discharged continuously and sent to the disposal (for example incineration) thereof.

What is advantageous about acrylic acid which has been prepared by the inventive procedure (or originates from an inventive preparation) and has been converted, for example by absorptive and/or condensative measures, from the gas phase obtained in the thermolysis of the poly-3-hydroxypropionate to the condensed (preferably liquid) phase is that it does not have the fingerprint of low molecular weight aldehydes present therein as impurities which is typical of acrylic acid produced by heterogeneously catalyzed partial oxidations of $C_3$ precursor compounds (e.g. propylene, propane, acrolein, glycerol, propionic acid, propanol, etc.) (cf., for example, DE 102011076931 A1).

These impurities are found to be extremely disruptive in the case of use of the acrylic acid and/or of the conjugate (Brønsted) base thereof for preparation of polymers by free-radically initiated polymerization, optionally in a mixture with other mono- and/or polyunsaturated (for example ethylenically) compounds, even in very small amounts (1 to 10 ppm by weight based on the weight of the mass of acrylic acid) (for example, they can undesirably retard the free-radically initiated polymerization or hinder or impair the preparation of polymer with particularly high molecular weight as a result of their "regulating action").

Accordingly, particularly advantageous processes for inventive preparation of acrylic acid are those followed by a process for free-radical polymerization in which the acrylic acid prepared, as such and/or in the form of its conjugate base (what is meant here is the conjugate Brønsted base, the acrylate anion), optionally in a mixture with other mono- and/or polyunsaturated compounds, is polymerized to polymer with free-radical initiation.

This is especially true when the process for free-radical polymerization is a process for producing water-"superabsorbent" polymer, as used, for example, in hygiene articles such as diapers (cf. DE 102011076931 A1 and the prior art cited in the same document).

Accordingly, the present invention comprises especially the following inventive embodiments:

1. A process for preparing acrylic acid from ethylene oxide and carbon monoxide, which comprises at least the following process steps:

a carbonylating conversion of ethylene oxide dissolved in an aprotic solvent with carbon monoxide at elevated pressure and elevated temperature in the presence of a catalyst system comprising at least one cobalt source in a reaction zone A to obtain a product mixture A comprising poly-3-hydroxypropionate, a removal of poly-3-hydroxypropionate from the product mixture A in a separation zone A, and a thermolysis of poly-3-hydroxypropionate removed in separation zone A in a thermolysis zone A to form acrylic acid, wherein the removal of poly-3-hydroxypropionate from product mixture A in separation zone A comprises at least one of the following process measures:

an addition of water and/or an aqueous solution as an aqueous precipitation liquid to one or more portions of product mixture A and/or to the total amount of product mixture A in order to precipitate poly-3-hydroxypropionate present dissolved in a portion of product mixture A or in the total amount of product mixture A;

a wash of poly-3-hydroxypropionate removed from product mixture A in separation zone A with water and/or with an aqueous solution as an aqueous wash liquid.

2. The process according to embodiment 1, wherein the aprotic solvent comprises or is at least one solvent from the group consisting of saturated hydrocarbons, aromatic hydrocarbons, halogenated saturated hydrocarbons, halogenated aromatic hydrocarbons, esters of organic acids, ketones, nitriles, dialkylamides, carbonic esters, sulfoxides, sulfones, N-alkylpyrrolidones, cyclic ethers and acyclic ethers.

3. The process according to embodiment 1 or 2, wherein the aprotic solvent comprises or is at least one solvent from the group consisting of n-hexane, n-heptane, petroleum ether, cyclohexane, benzene, toluene, dichloromethane, n-butyl propionate, phenyl acetate, glyceryl acetate, ethyl acetate, acetone, ethyl methyl ketone, methyl isobutyl ketone, benzophenone, acetonitrile, propionitrile, n-butyronitrile, benzonitrile, dimethylformamide, dimethylacetamide, dimethyl carbonate, diethyl carbonate, ethyl methyl carbonate, ethylene carbonate, propylene carbonate, dimethyl sulfoxide, sulfolane, N-methylpyrrolidone, ethylene oxide, diethyl ether, anisole, tetrahydrofuran, 1,4-dioxane, diphenyl ether, alkylene glycol dialkyl ethers and polyalkylene glycol dialkyl ethers.

4. The process according to embodiment 3, wherein the alkylene glycol dialkyl ether is an ethylene glycol dialkyl ether.

5. The process according to embodiment 3, wherein the ethylene glycol dialkyl ether is ethylene glycol dimethyl ether.

6. The process according to embodiment 3, wherein the polyalkylene glycol ether is diethylene glycol diethyl ether, diethylene glycol dimethyl ether, triethylene glycol dimethyl ether and/or tetraethylene glycol dimethyl ether.

7. The process according to any of embodiments 1 to 3, wherein the aprotic solvent has at least one covalently bonded oxygen atom.

8. The process according to embodiment 7, wherein the oxygen atom is an ether oxygen atom.

9. The process according to any of embodiments 1 to 3, wherein the aprotic solvent comprises or is one or more than one substance which comprises at most oxygen and/or sulfur as an atom type other than carbon and hydrogen.

10. The process according to any of embodiments 1 to 9, wherein the aprotic solvent is liquid at a pressure of $1.0133 \cdot 10^5$ Pa and at least one temperature within the range from 0° C. to 50° C.

11. The process according to any of embodiments 1 to 10, wherein the aprotic solvent is liquid at a pressure of $1.0133 \cdot 10^5$ Pa and at least one temperature within the range from 5° C. to 40° C.

12. The process according to any of embodiments 1 to 10, wherein the aprotic solvent is liquid at a pressure of $1.0133 \cdot 10^5$ Pa and at least one temperature within the range from 10° C. to 30° C.

13. The process according to any of embodiments 1 to 12, wherein the aprotic solvent comprises or is at least one solvent whose relative static permittivity number as a liquid pure substance at the temperature of 293.15 K and the pressure of $1.0133 \cdot 10^5$ Pa is in the range from 2 to 35.

14. The process according to any of embodiments 1 to 13, wherein the aprotic solvent comprises or is at least one solvent whose relative static permittivity number as a liquid pure substance at the temperature of 293.15 K and the pressure of $1.0133 \cdot 10^5$ Pa is in the range from 3 to 20.

15. The process according to any of embodiments 1 to 14, wherein the aprotic solvent comprises or is at least one solvent whose relative static permittivity number as a liquid pure substance at the temperature of 293.15 K and the pressure of $1.0133 \cdot 10^5$ Pa is in the range from 4 to 15.

16. The process according to any of embodiments 1 to 15, wherein the aprotic solvent comprises or is at least one solvent whose relative static permittivity number as a liquid pure substance at the temperature of 293.15 K and the pressure of $1.0133 \cdot 10^5$ Pa is in the range from 5 to 10.

17. The process according to embodiment 1, wherein the aprotic solvent comprises or is at least one solvent from the group consisting of tetrahydrofuran, ethylene oxide, 1,4-dioxane, ethylene glycol dimethyl ether, diethylene glycol dimethyl ether and triethylene glycol dimethyl ether.

18. The process according to embodiment 1, wherein the aprotic solvent comprises or is at least one solvent from the group consisting of ethylene glycol dimethyl ether, diethylene glycol dimethyl ether and triethylene glycol dimethyl ether.

19. The process according to any of embodiments 1 to 18, wherein the aprotic solvent is an aprotic solvent only to an extent of at least 90% of its weight.

20. The process according to any of embodiments 1 to 18, wherein the aprotic solvent is an aprotic solvent only to an extent of at least 95% of its weight.

21. The process according to any of embodiments 1 to 18, wherein the aprotic solvent is an aprotic solvent only to an extent of at least 98% of its weight.

22. The process according to any of embodiments 1 to 18, wherein the aprotic solvent is an aprotic solvent only to an extent of at least 99% of its weight.

23. The process according to any of embodiments 1 to 22, wherein the poly-3-hydroxypropionate removed from product mixture A has a relative weight-average molecular weight of 1000 to 20 000, or of 2000 to 15 000.

24. The process according to any of embodiments 1 to 23, wherein the polydispersity Q of the poly-3-hydroxypropionate removed from product mixture A is less than or equal to 2.5.

25. The process according to any of embodiments 1 to 24, wherein the catalyst system comprises the at least one cobalt source in such an amount that it comprises, based on the molar amount of ethylene oxide for carbonylating conversion, 0.005 to 20 mol % of Co.

26. The process according to any of embodiments 1 to 25, wherein the catalyst system comprises the at least one cobalt source in such an amount that it comprises, based on the molar amount of ethylene oxide for carbonylating conversion, 0.05 to 10 mol % of Co.

27. The process according to any of embodiments 1 to 26, wherein the catalyst system comprises the at least one cobalt source in such an amount that it comprises, based on the molar amount of ethylene oxide for carbonylating conversion, 0.1 to 8 mol % of Co.

28. The process according to any of embodiments 1 to 27, wherein the catalyst system comprises the at least one cobalt source in such an amount that it comprises, based on the molar amount of ethylene oxide for carbonylating conversion, 0.5 to 5 mol % of Co.

29. The process according to any of embodiments 1 to 28, wherein at least one cobalt source is a salt of cobalt.

30. The process according to embodiment 29, wherein the salt of cobalt is cobalt formate, cobalt acetate, cobalt acetylacetonate and/or cobalt sulfate.

31. The process according to any of embodiments 1 to 28, wherein at least one cobalt source is finely divided cobalt metal.

32. The process according to any of embodiments 1 to 28, wherein at least one cobalt source is a cobalt carbonyl compound.
33. The process according to any of embodiments 1 to 28, wherein at least one cobalt source is dicobalt octacarbonyl.
34. The process according to any of embodiments 1 to 33, wherein the catalyst system comprises at least one Brønsted acid as cocatalyst A.
35. The process according to embodiment 34, wherein the at least one Brønsted acid is at least one acid from the group consisting of inorganic acids, organic carboxylic acids, organic sulfonic acids, water and hydroxyaromatic compounds.
36. The process according to embodiment 35, wherein the at least one Brønsted acid is at least one acid from the group consisting of water, hydrochloric acid, sulfuric acid, phosphoric acid, formic acid, acetic acid, adipic acid, glutaric acid, trichloroacetic acid, trifluoroacetic acid, benzoic acid, 2,4,6-trimethylbenzoic acid, p-toluenesulfonic acid, phenol, 1-naphthol and 2-naphthol.
37. The process according to embodiment 36, wherein the at least one Brønsted acid is phenol and/or acetic acid.
38. The process according to any of embodiments 34 to 37, wherein the catalyst system comprises the at least one cobalt source and the at least one cocatalyst A in such amounts that the $M_A:M_{Co}$ ratio, formed from the total molar amount $M_A$ of cocatalysts A present in the catalyst system and the total molar amount $M_{Co}$ of cobalt present in the catalyst system, is 5:1 to 1:5.
39. The process according to any of embodiments 34 to 38, wherein the catalyst system comprises the at least one cobalt source and the at least one cocatalyst A in such amounts that the $M_A:M_{Co}$ ratio, formed from the total molar amount $M_A$ of cocatalysts A present in the catalyst system and the total molar amount $M_{Co}$ of cobalt present in the catalyst system, is 4:1 to 1:4.
40. The process according to any of embodiments 34 to 39, wherein the catalyst system comprises the at least one cobalt source and the at least one cocatalyst A in such amounts that the $M_A:M_{Co}$ ratio, formed from the total molar amount $M_A$ of cocatalysts A present in the catalyst system and the total molar amount $M_{Co}$ of cobalt present in the catalyst system, is 3:1 to 1:3.
41. The process according to any of embodiments 34 to 40, wherein the catalyst system comprises the at least one cobalt source and the at least one cocatalyst A in such amounts that the $M_A:M_{Co}$ ratio, formed from the total molar amount $M_A$ of cocatalysts A present in the catalyst system and the total molar amount $M_{Co}$ of cobalt present in the catalyst system, is 2:1 to 1:2.
42. The process according to any of embodiments 1 to 41, wherein the catalyst system comprises at least one Brønsted base as cocatalyst B.
43. The process according to embodiment 42, wherein the $pK_B$ of the at least one Brønsted base is ≥7.
44. The process according to embodiment 42, wherein the $pK_B$ of the at least one Brønsted base is ≥8.
45. The process according to embodiment 42, wherein the $pK_B$ of the at least one Brønsted base is ≥9.
46. The process according to embodiment 42, wherein the $pK_B$ of the at least one Brønsted base is ≥10.
47. The process according to any of embodiments 42 to 46, wherein the at least one Brønsted base is an aromatic or nonaromatic cyclic compound having at least one nitrogen atom as well as carbon atoms in the ring.
48. The process according to embodiment 42, wherein the at least one Brønsted base is at least one Brønsted base from the group consisting of the halide anions I⁻, Cl⁻ and F⁻, the acetate anion, pyrrole, N-methyl-2-pyrrolidone, 3-pyrrolidone, piperidine, N-methylpiperidine, indole, indoline, imidazole, pyrazole, N,N-dimethylformamide, acetaniline, N-methylimidazole, N-methyl-2-pyrrolidone, 3-pyrrolidone, piperidine, N-methylpiperidine, indole, indoline, imidazole, pyrazole, N,N-dimethylformamide, acetanilide, N-methylimidazole, 2-picoline, 3-picoline, 4-picoline, pyrimidine, the amide of nicotinic acid, pyrazine, quinoline, isoquinoline, quinoxaline, 1,10-phenanthroline, the bipyridines and pyridine.
49. The process according to any of embodiments 42 to 48, wherein the catalyst system comprises the at least one cobalt source and the at least one cocatalyst B in such amounts that the $M_B:M_{Co}$ ratio, formed from the total molar amount $M_B$ of cocatalysts B present in the catalyst system and the total molar amount $M_{Co}$ of cobalt present in the catalyst system, is 5:1 to 1:5.
50. The process according to any of embodiments 42 to 49, wherein the catalyst system comprises the at least one cobalt source and the at least one cocatalyst B in such amounts that the $M_B:M_{Co}$ ratio, formed from the total molar amount $M_B$ of cocatalysts B present in the catalyst system and the total molar amount $M_{Co}$ of cobalt present in the catalyst system, is 4:1 to 1:4.
51. The process according to any of embodiments 42 to 50, wherein the catalyst system comprises the at least one cobalt source and the at least one cocatalyst B in such amounts that the $M_B:M_{Co}$ ratio, formed from the total molar amount $M_B$ of cocatalysts B present in the catalyst system and the total molar amount $M_{Co}$ of cobalt present in the catalyst system, is 3:1 to 1:3.
52. The process according to any of embodiments 42 to 51, wherein the catalyst system comprises the at least one cobalt source and the at least one cocatalyst B in such amounts that the $M_B:M_{Co}$ ratio, formed from the total molar amount $M_B$ of cocatalysts B present in the catalyst system and the total molar amount $M_{Co}$ of cobalt present in the catalyst system, is 2:1 to 1:2.
53. The process according to any of embodiments 1 to 52, wherein the catalyst system comprises at least one Brønsted acid as cocatalyst A and at least one Brønsted base as cocatalyst B.
54. The process according to embodiment 53, wherein cocatalyst A is phenol and cocatalyst B is pyridine.
55. The process according to embodiment 53 or 54, wherein the catalyst system comprises the at least one cocatalyst A and the at least one cocatalyst B in such amounts that the $M_A:M_B$ ratio, formed from the total molar amount $M_A$ of cocatalysts A present in the catalyst system and the total molar amount $M_B$ of cocatalysts B present in the catalyst system, is 1:4 to 4:1.
56. The process according to any of embodiments 53 to 55, wherein the catalyst system comprises the at least one cocatalyst A and the at least one cocatalyst B in such amounts that the $M_A:M_B$ ratio, formed from the total molar amount $M_A$ of cocatalysts A present in the catalyst system and the total molar amount $M_B$ of cocatalysts B present in the catalyst system, is 1:2 to 2:1.
57. The process according to any of embodiments 53 to 56, wherein the catalyst system comprises the at least one cocatalyst A and the at least one cocatalyst B in such amounts that the $M_A:M_B$ ratio, formed from the total molar amount $M_A$ of cocatalysts A present in the catalyst system and the total molar amount $M_B$ of cocatalysts B present in the catalyst system, is 1:1.

58. The process according to any of embodiments 1 to 57, wherein the catalyst system comprises at least one compound as at least one cocatalyst C which has both at least one nucleophilic Brønsted-basic functionality like a cocatalyst B and at least one Brønsted-acidic functionality like a cocatalyst A.
59. The process according to embodiment 58, wherein the at least one cocatalyst C is an aromatic nitrogen heterocycle which additionally has at least one hydroxyl group and/or at least one carboxyl group in covalently bonded form.
60. The process according to embodiment 59, wherein the aromatic nitrogen heterocycle is fused to one or more than one other aromatic and/or aliphatic ring system.
61. The process according to embodiment 60, wherein the at least one hydroxyl group and/or carboxyl group is covalently bonded to the fused ring system.
62. The process according to either of embodiments 58 and 59, wherein the at least one cocatalyst C is at least one compound from the group consisting of 2-hydroxypyridine, 3-hydroxypyridine, 4-hydroxypyridine, 3,4-dihydroxypyridine, 3-hydroxyquinoline, 4-hydroxy-2-methylpyridine, 3-hydroxy-4-methylpyridine, 2,6-dihydroxypyridine, 2-hydroxyquinoline, 1-hydroxyisoquinoline, 3-hydroxyquinoline, 2,3-dihydroxyquinoxaline, 8-hydroxyquinoline, 2-pyridylmethanol, 3-pyridylmethanol, 2-(2-pyridyl)ethanol and nicotinic acid.
63. The process according to any of embodiments 58 to 62, wherein the aprotic solvent comprises diglyme, the at least one cobalt source comprises dicobalt octacarbonyl, and the catalyst system additionally comprises 3-hydroxypyridine as at least one cocatalysts C.
64. The process according to any of embodiments 58 to 63, wherein the catalyst system comprises the at least one cobalt source and the at least one cocatalyst C in such amounts that the $M_C:M_{Co}$ ratio, formed from the total molar amount $M_C$ of cocatalysts C present in the catalyst system and the total molar amount $M_{Co}$ of cobalt present in the catalyst system, is 5:1 to 1:5.
65. The process according to any of embodiments 58 to 64, wherein the catalyst system comprises the at least one cobalt source and the at least one cocatalyst C in such amounts that the $M_C:M_{Co}$ ratio, formed from the total molar amount $M_C$ of cocatalysts C present in the catalyst system and the total molar amount $M_{Co}$ of cobalt present in the catalyst system, is 4:1 to 1:4.
66. The process according to any of embodiments 58 to 65, wherein the catalyst system comprises the at least one cobalt source and the at least one cocatalyst C in such amounts that the $M_C:M_{Co}$ ratio, formed from the total molar amount $M_C$ of cocatalysts C present in the catalyst system and the total molar amount $M_{Co}$ of cobalt present in the catalyst system, is 3:1 to 1:3.
67. The process according to any of embodiments 58 to 66, wherein the catalyst system comprises the at least one cobalt source and the at least one cocatalyst C in such amounts that the $M_C:M_{Co}$ ratio, formed from the total molar amount $M_C$ of cocatalysts C present in the catalyst system and the total molar amount $M_{Co}$ of cobalt present in the catalyst system, is 2:1 to 1:2.
68. The process according to any of embodiments 1 to 67, wherein the catalyst system comprises, as the cobalt source, at least one salt of the anion $Co(CO)_4^-$ and/or the Brønsted acid thereof $HCo(CO)_4$.
69. The process according to any of embodiments 1 to 68, wherein the catalyst system comprises at least one of the catalyst systems listed in table 1 of the present document.
70. The process according to any of embodiments 1 to 69, wherein the carbonylating conversion is performed at a reaction temperature in the range from 25 to 150° C.
71. The process according to any of embodiments 1 to 70, wherein the carbonylating conversion is performed at a reaction temperature in the range from 35 to 120° C.
72. The process according to any of embodiments 1 to 71, wherein the carbonylating conversion is performed at a reaction temperature in the range from 50 to 120° C.
73. The process according to any of embodiments 1 to 72, wherein the carbonylating conversion is performed at a reaction temperature in the range from 60 to 100° C.
74. The process according to any of embodiments 1 to 73, wherein the carbonylating conversion is performed at a reaction temperature in the range from 70 to 90° C.
75. The process according to any of embodiments 1 to 74, wherein the carbonylating conversion is performed at a working pressure of $1.0133 \cdot 10^7$ Pa to $2.5 \cdot 10^7$ Pa.
76. The process according to any of embodiments 1 to 75, wherein the carbonylating conversion is performed at a working pressure of $2 \cdot 10^5$ Pa to $2 \cdot 10^7$ Pa.
77. The process according to any of embodiments 1 to 76, wherein the carbonylating conversion is performed at a working pressure of $5 \cdot 10^5$ Pa to $1.5 \cdot 10^7$ Pa.
78. The process according to any of embodiments 1 to 77, wherein the carbonylating conversion is performed at a working pressure of $1 \cdot 10^6$ Pa to $1 \cdot 10^7$ Pa.
79. The process according to any of embodiments 1 to 78, wherein the carbonylating conversion is performed at a working pressure of $2 \cdot 10^6$ Pa to $9 \cdot 10^6$ Pa.
80. The process according to any of embodiments 1 to 79, wherein the carbonylating conversion is performed at a working pressure of $4 \cdot 10^6$ Pa to $8 \cdot 10^6$ Pa.
81. The process according to any of embodiments 1 to 80, wherein the carbon monoxide used for the carbonylating conversion, based on the total volume thereof, comprises ≤1% by volume of constituents other than CO.
82. The process according to any of embodiments 1 to 80, wherein the carbon monoxide used for the carbonylating conversion, based on the total volume thereof, comprises ≤0.1% by volume of constituents other than CO.
83. The process according to any of embodiments 1 to 80, wherein the carbon monoxide used for the carbonylating conversion, based on the total volume thereof, comprises ≤0.01% by volume of constituents other than CO.
84. The process according to any of embodiments 1 to 80, wherein the carbon monoxide used for the carbonylating conversion, based on the total volume thereof, comprises ≤0.001% by volume of constituents other than CO.
85. The process according to any of embodiments 1 to 80, wherein the carbon monoxide used for the carbonylating conversion is present in a mixture of carbon monoxide and at least one inert gas.
86. The process according to embodiment 85, wherein the inert gas is molecular nitrogen and/or a noble gas.
87. The process according to any of embodiments 1 to 86, wherein the carbonylating conversion is performed at a partial pressure of CO of $1.0133 \cdot 10^5$ Pa to $2.5 \cdot 10^7$ Pa.
88. The process according to any of embodiments 1 to 87, wherein the carbonylating conversion is performed at a partial pressure of CO of $2 \cdot 10^5$ Pa to $2 \cdot 10^7$ Pa.
89. The process according to any of embodiments 1 to 88, wherein the carbonylating conversion is performed at a partial pressure of CO of $5 \cdot 10^5$ Pa to $1.5 \cdot 10^7$ Pa.
90. The process according to any of embodiments 1 to 89, wherein the carbonylating conversion is performed at a partial pressure of CO of $1 \cdot 10^6$ Pa to $1 \cdot 10^7$ Pa.

91. The process according to any of embodiments 1 to 90, wherein the carbonylating conversion is performed at a partial pressure of CO of $2 \cdot 10^6$ Pa to $9 \cdot 10^6$ Pa.
92. The process according to any of embodiments 1 to 91, wherein the carbonylating conversion is performed at a partial pressure of CO of $4 \cdot 10^6$ Pa to $8 \cdot 10^6$ Pa.
93. The process according to any of the embodiments 1 to 92, wherein the conversion of ethylene oxide in the carbonylating conversion is ≥90 mol %.
94. The process according to any of the embodiments 1 to 92, wherein the conversion of ethylene oxide in the carbonylating conversion is ≥95 mol %.
95. The process according to any of the embodiments 1 to 92, wherein the conversion of ethylene oxide in the carbonylating conversion is ≥98 mol %.
96. The process according to any of the embodiments 1 to 92, wherein the conversion of ethylene oxide in the carbonylating conversion is ≥99 mol %.
97. The process according to any of the embodiments 1 to 92, wherein the conversion of ethylene oxide in the carbonylating conversion is 99.9 mol %.
98. The process according to any of embodiments 1 to 97, wherein the carbonylating conversion is performed with exclusion of molecular oxygen.
99. The process according to any of embodiments 1 to 98, wherein the pH of the aqueous precipitation liquid, based on a temperature of 25° C. and a pressure of $1.0133 \cdot 10^5$ Pa, is ≤7.5.
100. The process according to any of embodiments 1 to 98, wherein the pH of the aqueous precipitation liquid, based on a temperature of 25° C. and a pressure of $1.0133 \cdot 10^5$ Pa, is ≤7.0.
101. The process according to any of embodiments 1 to 98, wherein the pH of the aqueous precipitation liquid, based on a temperature of 25° C. and a pressure of $1.0133 \cdot 10^5$ Pa, is ≤6.
102. The process according to any of embodiments 1 to 98, wherein the pH of the aqueous precipitation liquid, based on a temperature of 25° C. and a pressure of $1.0133 \cdot 10^5$ Pa, is ≤5.
103. The process according to any of embodiments 1 to 98, wherein the pH of the aqueous precipitation liquid, based on a temperature of 25° C. and a pressure of $1.0133 \cdot 10^5$ Pa, is ≤4.
104. The process according to any of embodiments 1 to 103, wherein the pH of the aqueous precipitation liquid, based on a temperature of 25° C. and a pressure of $1.0133 \cdot 10^5$ Pa, is ≥0.
105. The process according to any of embodiments 1 to 104, wherein the pH of the aqueous precipitation liquid, based on a temperature of 25° C. and a pressure of $1.0133 \cdot 10^5$ Pa, is ≥1.
106. The process according to any of embodiments 1 to 105, wherein the pH of the aqueous precipitation liquid, based on a temperature of 25° C. and a pressure of $1.0133 \cdot 10^5$ Pa, is ≥2.
107. The process according to any of embodiments 1 to 106, wherein the pH of product mixture A or of a portion of product mixture A on completion of addition of an aqueous precipitation liquid, based on a temperature of 25° C. and a pressure of $1.0133 \cdot 10^5$ Pa, is ≤7.5.
108. The process according to any of embodiments 1 to 106, wherein the pH of product mixture A or of a portion of product mixture A on completion of addition of an aqueous precipitation liquid, based on a temperature of 25° C. and a pressure of $1.0133 \cdot 10^5$ Pa, is ≤7.0.
109. The process according to any of embodiments 1 to 106, wherein the pH of product mixture A or of a portion of product mixture A on completion of addition of an aqueous precipitation liquid, based on a temperature of 25° C. and a pressure of $1.0133 \cdot 10^5$ Pa, is ≤6.
110. The process according to any of embodiments 1 to 106, wherein the pH of product mixture A or of a portion of product mixture A on completion of addition of an aqueous precipitation liquid, based on a temperature of 25° C. and a pressure of $1.0133 \cdot 10^5$ Pa, is ≤5.
111. The process according to any of embodiments 1 to 106, wherein the pH of product mixture A or of a portion of product mixture A on completion of addition of an aqueous precipitation liquid, based on a temperature of 25° C. and a pressure of $1.0133 \cdot 10^5$ Pa, is ≤4.
112. The process according to any of embodiments 1 to 111, wherein the pH of product mixture A or of a portion of product mixture A on completion of addition of an aqueous precipitation liquid, based on a temperature of 25° C. and a pressure of $1.0133 \cdot 10^5$ Pa, is ≥0.
113. The process according to any of embodiments 1 to 112, wherein the pH of product mixture A or of a portion of product mixture A on completion of addition of an aqueous precipitation liquid, based on a temperature of 25° C. and a pressure of $1.0133 \cdot 10^5$ Pa, is ≥1.
114. The process according to any of embodiments 1 to 113, wherein the pH of product mixture A or of a portion of product mixture A on completion of addition of an aqueous precipitation liquid, based on a temperature of 25° C. and a pressure of $1.0133 \cdot 10^5$ Pa, is ≥2.
115. The process according to any of embodiments 1 to 114, wherein the aqueous precipitation liquid is the aqueous solution of an inorganic acid and/or of an organic acid.
116. The process according to embodiment 115, wherein the aqueous precipitation liquid is at least one aqueous solution from the group consisting of aqueous sulfuric acid solution, aqueous carbonic acid solution, aqueous hydrochloric acid solution, aqueous phosphoric acid solution, aqueous acrylic acid solution, aqueous oxalic acid solution, aqueous formic acid solution, aqueous acetic acid solution, aqueous propionic acid solution, aqueous fumaric acid solution, aqueous maleic acid solution and aqueous methanesulfonic acid solution.
117. The process according to any of embodiments 1 to 114, wherein the aqueous precipitation liquid is an aqueous acetic acid solution.
118. The process according to any of embodiments 1 to 117, wherein the water content of the aqueous precipitation liquid, based on the weight thereof, is at least 10% by weight or at least 20% by weight.
119. The process according to any of embodiments 1 to 117, wherein the water content of the aqueous precipitation liquid, based on the weight thereof, is at least 30% by weight.
120. The process according to any of embodiments 1 to 117, wherein the water content of the aqueous precipitation liquid, based on the weight thereof, is at least 40% by weight.
121. The process according to any of embodiments 1 to 117, wherein the water content of the aqueous precipitation liquid, based on the weight thereof, is at least 50% by weight.
122. The process according to any of embodiments 1 to 117, wherein the water content of the aqueous precipitation liquid, based on the weight thereof, is at least 60% by weight.

123. The process according to any of embodiments 1 to 117, wherein the water content of the aqueous precipitation liquid, based on the weight thereof, is at least 70% by weight.
124. The process according to any of embodiments 1 to 117, wherein the water content of the aqueous precipitation liquid, based on the weight thereof, is at least 80% by weight.
125. The process according to any of embodiments 1 to 117, wherein the water content of the aqueous precipitation liquid, based on the weight thereof, is at least 90% by weight.
126. The process according to any of embodiments 1 to 117, wherein the water content of the aqueous precipitation liquid, based on the weight thereof, is at least 95% by weight.
127. The process according to any of embodiments 1 to 117, wherein the water content of the aqueous precipitation liquid, based on the weight thereof, is at least 97% by weight.
128. The process according to any of embodiments 1 to 117, wherein the water content of the aqueous precipitation liquid, based on the weight thereof, is at least 99% by weight.
129. The process according to any of embodiments 1 to 128, wherein the addition of the aqueous precipitation liquid is undertaken in the presence of at least one oxidizing agent (for Co in oxidation states <+2).
130. The process according to embodiment 129, wherein the addition of the aqueous precipitation liquid is undertaken in the presence of air or in the presence of a molecular oxygen-comprising gas other than air.
131. The process according to any of embodiments 1 to 130, wherein, before, during and/or after the addition of the aqueous precipitation liquid, one or more than one oxidizing agent is added to a portion of product mixture A, to the aqueous precipitation liquid itself, to the entirety of product mixture A and/or to the resulting mixture of a portion or of the entirety of product mixture A and the aqueous precipitation liquid.
132. The process according to embodiment 131, wherein one or more than one oxidizing agent from the group consisting of ozone, hydrogen peroxide, molecular oxygen, perchlorate, perchloric acid and nitric acid is added.
133. The process according to any of embodiments 1 to 132, wherein the aqueous precipitation liquid comprises molecular oxygen in dissolved form.
134. The process according to any of embodiments 1 to 133, wherein the aqueous precipitation liquid is saturated with molecular oxygen.
135. The process according to any of embodiments 1 to 134, wherein a molecular oxygen-comprising gas is supplied to product mixture A and/or to a portion of product mixture A in addition to the aqueous precipitation liquid.
136. The process according to embodiment 135, wherein the molecular oxygen-comprising gas is air or comprises air.
137. The process according to embodiment 135 or 136, wherein the molecular oxygen-comprising gas is supplied to the aqueous mixture formed from product mixture A or from a portion of product mixture A by addition of the aqueous precipitation liquid.
138. The process according to embodiment 137, wherein the molecular oxygen-comprising gas is supplied at a temperature of the aqueous mixture of 10 to 95° C., or of 20 to 95° C., or of 30° C. to 95° C.
139. The process according to embodiment 137 or 138, wherein the molecular oxygen-comprising gas is supplied at a temperature of the aqueous mixture of 40° C. to 90° C.
140. The process according to either of embodiments 137 and 139, wherein the molecular oxygen-comprising gas is supplied at a temperature of the aqueous mixture of 50° C. to 80° C. or of 50° C. to 60° C.
141. The process according to any of embodiments 137 to 140, wherein the temperature of the aqueous mixture is reduced during and/or after the supply of the molecular oxygen-comprising gas.
142. The process according to any of embodiments 1 to 141, wherein the pH of the aqueous wash liquid, based on a temperature of 25° C. and a pressure of $1.0133 \cdot 10^5$ Pa, is ≤7.5.
143. The process according to any of embodiments 1 to 141, wherein the pH of the aqueous wash liquid, based on a temperature of 25° C. and a pressure of $1.0133 \cdot 10^5$ Pa, is ≤7.0.
144. The process according to any of embodiments 1 to 141, wherein the pH of the aqueous wash liquid, based on a temperature of 25° C. and a pressure of $1.0133 \cdot 10^5$ Pa, is ≤6.
145. The process according to any of embodiments 1 to 141, wherein the pH of the aqueous wash liquid, based on a temperature of 25° C. and a pressure of $1.0133 \cdot 10^5$ Pa, is ≤5.
146. The process according to any of embodiments 1 to 141, wherein the pH of the aqueous wash liquid, based on a temperature of 25° C. and a pressure of $1.0133 \cdot 10^5$ Pa, is ≤4.
147. The process according to any of embodiments 1 to 146, wherein the pH of the aqueous wash liquid, based on a temperature of 25° C. and a pressure of $1.0133 \cdot 10^5$ Pa, is ≥0.
148. The process according to any of embodiments 1 to 147, wherein the pH of the aqueous wash liquid, based on a temperature of 25° C. and a pressure of $1.0133 \cdot 10^5$ Pa, is ≥1.
149. The process according to any of embodiments 1 to 148, wherein the pH of the aqueous wash liquid, based on a temperature of 25° C. and a pressure of $1.0133 \cdot 10^5$ Pa, is 2.
150. The process according to any of embodiments 1 to 149, wherein the aqueous wash liquid is the aqueous solution of an inorganic acid and/or of an organic acid.
151. The process according to embodiment 150, wherein the aqueous wash liquid is at least one aqueous solution from the group consisting of aqueous sulfuric acid solution, aqueous carbonic acid solution, aqueous hydrochloric acid solution, aqueous phosphoric acid solution, aqueous acrylic acid solution, aqueous oxalic acid solution, aqueous formic acid solution, aqueous acetic acid solution, aqueous propionic acid solution, aqueous fumaric acid solution, aqueous maleic acid solution and aqueous methanesulfonic acid solution.
152. The process according to any of embodiments 1 to 151, wherein the aqueous wash liquid is an aqueous acetic acid solution.
153. The process according to any of embodiments 1 to 152, wherein the water content of the aqueous wash liquid, based on the weight thereof, is at least 10% by weight or at least 20% by weight.
154. The process according to any of embodiments 1 to 152, wherein the water content of the aqueous wash liquid, based on the weight thereof, is at least 30% by weight.

155. The process according to any of embodiments 1 to 152, wherein the water content of the aqueous wash liquid, based on the weight thereof, is at least 40% by weight.
156. The process according to any of embodiments 1 to 152, wherein the water content of the aqueous wash liquid, based on the weight thereof, is at least 50% by weight.
157. The process according to any of embodiments 1 to 152, wherein the water content of the aqueous wash liquid, based on the weight thereof, is at least 60% by weight.
158. The process according to any of embodiments 1 to 152, wherein the water content of the aqueous wash liquid, based on the weight thereof, is at least 70% by weight.
159. The process according to any of embodiments 1 to 152, wherein the water content of the aqueous wash liquid, based on the weight thereof, is at least 80% by weight.
160. The process according to any of embodiments 1 to 152, wherein the water content of the aqueous wash liquid, based on the weight thereof, is at least 90% by weight.
161. The process according to any of embodiments 1 to 152, wherein the water content of the aqueous wash liquid, based on the weight thereof, is at least 95% by weight.
162. The process according to any of embodiments 1 to 152, wherein the water content of the aqueous wash liquid, based on the weight thereof, is at least 97% by weight.
163. The process according to any of embodiments 1 to 152, wherein the water content of the aqueous wash liquid, based on the weight thereof, is at least 99% by weight.
164. The process according to any of embodiments 1 to 163, wherein the washing of poly-3-hydroxypropionate removed from product mixture A is effected in the presence of at least one oxidizing agent (for Co in oxidation states <+2).
165. The process according to any of embodiments 1 to 164, wherein the washing of the poly-3-hydroxypropionate removed from product mixture A is undertaken in the presence of air and/or a molecular oxygen-comprising gas other than air.
166. The process according to embodiment 164, wherein the at least one oxidizing agent is an oxidizing agent from the group consisting of ozone, hydrogen peroxide, molecular oxygen, perchlorate, perchloric acid and nitric acid.
167. The process according to any of embodiments 1 to 166, wherein the aqueous wash liquid comprises molecular oxygen or air in dissolved form.
168. The process according to any of embodiments 1 to 167, wherein the aqueous wash liquid is saturated with molecular oxygen or with air.
169. The process according to any of embodiments 1 to 168, wherein the washing of poly-3-hydroxypropionate removed from product mixture A is effected by sucking and/or forcing aqueous wash liquid through the poly-3-hydroxypropionate removed from product gas mixture A.
170. The process according to embodiment 169, wherein the temperature of the aqueous wash liquid is 10° C. to 95° C.
171. The process according to embodiment 169 or 170, wherein the temperature of the aqueous wash liquid is 20° C. to 90° C.
172. The process according to any of embodiments 169 to 171, wherein the temperature of the aqueous wash liquid is 30° C. to 80° C.
173. The process according to any of embodiments 169 to 172, wherein the temperature of the aqueous wash liquid is 40° C. to 70° C.
174. The process according to either of embodiments 169 and 173, wherein the temperature of the aqueous wash liquid is 50° C. to 60° C.
175. The process according to any of embodiments 1 to 168, wherein the washing of poly-3-hydroxypropionate removed from product mixture A with the aqueous wash liquid is effected by suspending the poly-3-hydroxypropionate removed from product mixture A in the aqueous wash liquid and subsequently removing it again from the resulting aqueous suspension by the use of at least one mechanical separating operation.
176. The process according to embodiment 175, wherein a molecular oxygen-comprising gas flows through the aqueous suspension of the poly-3-hydroxypropionate.
177. The process according to embodiment 176, wherein the molecular oxygen-comprising gas is air, molecular oxygen and/or a mixture of molecular oxygen and at least one inert gas.
178. The process according to any of embodiments 175 to 177, wherein the aqueous suspension of the poly-3-hydroxypropionate is mixed at a temperature of 10° C. to 95° C.
179. The process according to embodiment 178, wherein the aqueous suspension of the poly-3-hydroxypropionate is mixed at a temperature of 20° C. to 90° C.
180. The process according to embodiment 178 or 179, wherein the aqueous suspension of the poly-3-hydroxypropionate is mixed at a temperature of 30° C. to 80° C.
181. The process according to any of embodiments 178 to 180, wherein the aqueous suspension of the poly-3-hydroxypropionate is mixed at a temperature of 40° C. to 70° C.
182. The process according to any of embodiments 178 to 181, wherein the aqueous suspension of the poly-3-hydroxypropionate is mixed at a temperature of 50° C. to 60° C.
183. The process according to any of embodiments 175 to 182, wherein the at least one mechanical separating operation is a filtration and/or a centrifugation.
184. The process according to any of embodiments 1 to 183, wherein the poly-3-hydroxypropionate removed (in a separation zone A) is dried prior to the thermolysis thereof.
185. The process according to embodiment 184, wherein the poly-3-hydroxypropionate removed (in a separation zone A) is washed with methanol prior to the drying thereof.
186. The process according to any of embodiments 1 to 185, wherein the thermolysis of the poly-3-hydroxypropionate (removed in a separation zone A) is effected from the solid substance thereof, or from the melt thereof, or from the solution thereof in a solvent, or from the suspension thereof in a dispersant, or from the emulsion thereof in a dispersant.
187. The process according to any of embodiments 1 to 185, wherein at least one splitting catalyst which catalyzes the thermolysis is added to the poly-3-hydroxypropionate (removed in a separation zone A) (optionally, for example, in an amount of, based on the weight of the mass of the poly-3-hydroxypropionate, from 0.01 to 15% by weight, or from 0.05 to 10% by weight, or from 0.1 to 5% by weight, or from 0.4 to 4% by weight, or from 1.5 to 3.5% by weight).
188. The process according to embodiment 186, wherein at least one splitting catalyst which catalyzes the thermolysis is added to the solid substance, or to the melt, or to the solution, or to the suspension, or to the emulsion.
189. The process according to embodiment 187 or 188, wherein the at least one splitting catalyst is a molecular organic active compound which, as well as carbon and hydrogen, as heteroatoms other than these, has at least one nitrogen atom and optionally at least one or more than one oxygen atom in covalently bonded form, with the proviso that
the organic active compound does not have any heteroatom other than carbon and hydrogen over and above nitrogen and oxygen, and
at least one nitrogen atom is a tertiary nitrogen atom.

190. The process according to embodiment 189, wherein the at least one molecular organic active compound has more than one tertiary nitrogen atom.

191. The process according to embodiment 190, wherein the at least one molecular organic active compound has at least two or at least three tertiary nitrogen atoms.

192. The process according to any of embodiments 189 to 191, wherein the at least one molecular organic active compound has at least one tertiary nitrogen atom which has a covalent bond to three different carbon atoms.

193. The process according to any of embodiments 189 to 192, wherein the at least one molecular organic active compound has at least two tertiary nitrogen atoms or at least three tertiary nitrogen atoms which each have a covalent bond to three different carbon atoms.

194. The process according to any of embodiments 189 to 192, wherein at least one tertiary nitrogen atom is an iminic nitrogen atom.

195. The process according to any of embodiments 189 to 194, wherein the at least one molecular organic active compound does not have any nitrogen atom to which one or more than one hydrogen atom is covalently bonded and/or any oxygen atom to which a hydrogen atom is covalently bonded.

196. The process according to any of embodiments 189 to 195, wherein the molar mass of the at least one molecular organic active compound is ≥59.1 g/mol and ≤600 g/mol.

197. The process according to any of embodiments 189 to 196, wherein the molar mass of the at least one molecular organic active compound is ≥75 g/mol and ≤500 g/mol.

198. The process according to any of embodiments 189 to 197, wherein the molar mass of the at least one molecular organic active compound is ≥100 g/mol and ≤400 g/mol.

199. The process according to any of embodiments 189 to 198, wherein the molar mass of the at least one molecular organic active compound is ≥125 g/mol and ≤300 g/mol.

200. The process according to any of embodiments 189 to 199, wherein the molar mass of the at least one molecular organic active compound is ≥150 g/mol and ≤250 g/mol.

201. The process according to any of embodiments 189 to 200, wherein the boiling point of the at least one molecular organic active compound based on a pressure of $1.0133 \cdot 10^5$ Pa is ≥180° C.

202. The process according to any of embodiments 189 to 200, wherein the boiling point of the at least one molecular organic active compound based on a pressure of $1.0133 \cdot 10^5$ Pa is ≥185° C.

203. The process according to any of embodiments 189 to 200, wherein the boiling point of the at least one molecular organic active compound based on a pressure of $1.0133 \cdot 10^5$ Pa is ≥190° C.

204. The process according to any of embodiments 189 to 203, wherein the boiling point of the at least one molecular organic active compound based on a pressure of $1.0133 \cdot 10^5$ Pa is ≤350° C.

205. The process according to any of embodiments 189 to 204, wherein the boiling point of the at least one molecular organic active compound based on a pressure of $1.0133 \cdot 10^5$ Pa is ≤330° C.

206. The process according to any of embodiments 189 to 205, wherein the boiling point of the at least one molecular organic active compound based on a pressure of $1.0133 \cdot 10^5$ Pa is ≤310° C.

207. The process according to any of embodiments 189 to 206, wherein the boiling point of the at least one molecular organic active compound based on a pressure of $1.0133 \cdot 10^5$ Pa is ≤290° C.

208. The process according to any of embodiments 189 to 207, wherein the boiling point of the at least one molecular organic active compound based on a pressure of $1.0133 \cdot 10^5$ Pa is ≤270° C.

209. The process according to any of embodiments 189 to 208, wherein the boiling point of the at least one molecular organic active compound based on a pressure of $1.0133 \cdot 10^5$ Pa is ≤250° C.

210. The process according to any of embodiments 189 to 209, wherein the boiling point of the at least one molecular organic active compound based on a pressure of $1.0133 \cdot 10^5$ Pa is ≤230° C.

211. The process according to any of embodiments 189 to 210, wherein the boiling point of the at least one molecular organic active compound based on a pressure of $1.0133 \cdot 10^5$ Pa is ≤200° C.

212. The process according to embodiment 189, wherein the at least one molecular organic active compound is selected from the group consisting of trimethylamine, triethylamine, tri-n-hexylamine, tri-n-butylamine, N-ethyl-N,N-diisopropylamine, pentamethyldiethylenetriamine, N,N,N',N'-tetramethyl-1,6-hexanediamine, bis(2-dimethylaminoethyl)ether, 2,2'-dimorpholinodiethyl ether, N,N-diethylethanolamine, N,N,N',N'-tetramethyl-1,3-propanediamine, N,N-dimethylcyclohexylamine, N,N-dimethyl-1,3-diaminopropane, N-methylimidazole, 1,2-dimethylimidazole, 2-hydroxypyridine, 3-hydroxypyridine and 4-hydroxypyridine.

213. The process according to embodiment 189, wherein the at least one molecular organic active compound is at least one poly-3-hydroxypropionate which has been etherified with the hydroxyl group of 2-hydroxypyridine, or of 3-hydroxypyridine, or of 4-hydroxypyridine.

214. The process according to embodiment 213, wherein the at least one molecular organic active compound is at least one poly-3-hydroxypropionate of the general structures

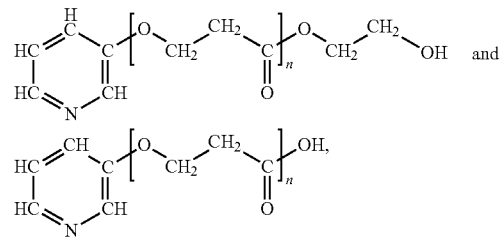

where n = an integer ≥ 1.

215. The process according to embodiment 214, wherein n≤250, or ≤200, or ≤150.

216. The process according to any of embodiments 189 to 215, wherein the thermolysis of the poly-3-hydroxypropionate (removed in a separation zone A) is effected from the solid substance thereof, or from the melt thereof, or from a solution thereof in a solvent, or from a suspension thereof in a dispersant, or from an emulsion thereof in a dispersant, which comprises, based on the weight of the poly-3-hydroxypropionate present, 0.01 to 15% by weight of the at least one molecular organic active compound.
217. The process according to any of embodiments 189 to 216, wherein the thermolysis of the poly-3-hydroxypropionate is effected from the solid substance thereof, or from the melt thereof, or from a solution thereof in a solvent, or from a suspension thereof in a dispersant, or from an emulsion thereof in a dispersant, which comprises, based on the weight of the poly-3-hydroxypropionate present, 0.05 to 10% by weight of the at least one molecular organic active compound.
218. The process according to any of embodiments 189 to 217, wherein the thermolysis of the poly-3-hydroxypropionate is effected from the solid substance thereof, or from the melt thereof, or from a solution thereof in a solvent, or from a suspension thereof in a dispersant, or from an emulsion thereof in a dispersant, which comprises, based on the weight of the poly-3-hydroxypropionate present, 0.1 to 5% by weight of the at least one molecular organic active compound.
219. The process according to any of embodiments 189 to 218, wherein the thermolysis of the poly-3-hydroxypropionate is effected from the solid substance thereof, or from the melt thereof, or from a solution thereof in a solvent, or from a suspension thereof in a dispersant, or from an emulsion thereof in a dispersant, which comprises, based on the weight of the poly-3-hydroxypropionate present, 0.5 to 4% by weight of the at least one molecular organic active compound.
220. The process according to any of embodiments 189 to 219, wherein the thermolysis of the poly-3-hydroxypropionate is effected from the solid substance thereof, or from the melt thereof, or from a solution thereof in a solvent, or from a suspension thereof in a dispersant, or from an emulsion thereof in a dispersant, which comprises, based on the weight of the poly-3-hydroxypropionate present, 1.5 to 3.5% by weight of the at least one molecular organic active compound.
221. The process according to any of embodiments 1 to 220, wherein the thermolysis is performed at a temperature of the poly-3-hydroxypropionate of 50° C. to 350° C., or of 100° C. to 300° C., or of 150° C. to 220° C., or of 160° C. to 200° C.
222. The process according to embodiment 186 or according to any of embodiments 188 to 221, wherein the thermolysis is performed at a temperature of the solid substance, or of the melt, or of the solution, or of the suspension, or of the emulsion, of 50° C. to 350° C.
223. The process according to embodiment 186 or according to any of embodiments 188 to 222, wherein the thermolysis is performed at a temperature of the solid substance, or of the melt, or of the solution, or of the suspension, or of the emulsion, of 100° C. to 300° C.
224. The process according to embodiment 186 or according to any of embodiments 188 to 223, wherein the thermolysis is performed at a temperature of the solid substance, or of the melt, or of the solution, or of the suspension, or of the emulsion, of 150° C. to 220° C.
225. The process according to embodiment 186 or according to any of embodiments 188 to 224, wherein the thermolysis is performed at a temperature of the solid substance, or of the melt, or of the solution, or of the suspension, or of the emulsion, of 160° C. to 200° C.
226. The process according to any of embodiments 1 to 225, wherein the thermolysis is performed at atmospheric pressure, above atmospheric pressure or below atmospheric pressure.
227. The process according to any of embodiments 1 to 226, wherein the thermolysis is performed at a working pressure in the range from $10^2$ to $10^7$ Pa.
228. The process according to any of embodiments 1 to 227, wherein the thermolysis is performed at a working pressure in the range from $10^3$ to $10^6$ Pa.
229. The process according to any of embodiments 1 to 228, wherein the thermolysis is performed at a working pressure in the range from $2 \cdot 10^3$ to $5 \cdot 10^5$ Pa.
230. The process according to any of embodiments 1 to 229, wherein $5 \cdot 10^3$ to $3 \cdot 10^5$ Pa.
231. The process according to embodiment 186 or according to any of embodiments 188 to 230, wherein, during the thermolysis, a stripping gas is conducted over the solid substance, or through the melt, or through the solution, or through the suspension, or through the emulsion, of the poly-3-hydroxypropionate.
232. The process according to embodiment 231, wherein the stripping gas comprises molecular oxygen or is free of molecular oxygen.
233. The process according to any of embodiments 1 to 232, wherein the thermolysis of the poly-3-hydroxypropionate is effected in the presence of at least one polymerization inhibitor (based on the weight of the mass of the poly-3-hydroxypropionate, for example, in the presence of 10 to 1000 ppm by weight, or 50 to 500 ppm by weight, or 150 to 350 ppm by weight, of at least one polymerization inhibitor).
234. The process according to embodiment 186 or according to any of embodiments 188 to 232, wherein the thermolysis of the poly-3-hydroxypropionate is effected from the solid substance thereof, or from the melt thereof, or from the solution thereof, or from the suspension thereof, or from the emulsion thereof, and this comprises at least one added polymerization inhibitor.
235. The process according to embodiment 233 or 234, wherein the at least one polymerization inhibitor is at least one polymerization inhibitor from the group consisting of o-, m- or p-cresol, 2-tert-butyl-4-methylphenol, 6-tert-butyl-2,4-dimethylphenol, 2,6-di-tert-butyl-4-methylphenol, 2-tert-butylphenol, 4-tert-butylphenol, 2,4-di-tert-butylphenol, 2-methyl-4-tert-butylphenol, hydroquinone, catechol, resorcinol, 2-methylhydroquinone and 2,5-di-tert-butylhydroquinone, para-aminophenol, para-nitrosophenol, 2-methoxyphenol, 2-ethoxyphenol, 4-methoxyphenol, mono- or di-tert-butyl-4-methoxyphenol, α-tocopherol, 4-hydroxy-2,2,6,6-tetramethylpiperidine N-oxyl, 2,2,6,6-tetramethylpiperidine N-oxyl, 4,4',4'''-tris (2,2,6,6-tetramethylpiperidine N-oxyl) phosphite, 3-oxo-2,2,5,5-tetra-methylpyrrolidine N-oxyl, N,N-diphenylamine, N-nitrosodiphenylamine, N,N'-dialkyl-para-phenylenediamine, where the alkyl radicals may be the same or different and each independently consist of 1 to 4 carbon atoms and may be straight-chain or branched, N,N-diethylhydroxylamine, triphenylphosphine, triphenyl phosphite, hypophosphorous acid, triethyl phosphite, diphenyl sulfide, phenothiazine, and all aforementioned inhibitors optionally in combination with metal salts, for example the chlorides, dithiocarbonates, sulfates, salicylates or acetates of copper, manganese, cerium, nickel and/or chromium.
236. The process according to embodiment 234 or 235, wherein the total amount of added polymerization inhibitor, based on the total amount of poly-3-hydroxypropionate present in the solid substance, or in the melt, or in the solution, or in the suspension, or in the emulsion, is 10 to 1000 ppm by weight.

237. The process according to any of embodiments 1 to 236, wherein the acrylic acid is converted from the acrylic acid-comprising gas phase formed in the thermolysis of the poly-3-hydroxypropionate to the liquid phase by absorptive and/or condensative measures.

238. The process according to embodiment 237, wherein the acrylic acid is separated from the liquid phase in an elevated purity compared to the liquid phase using at least one thermal separation process, and the at least one thermal separation process comprises at least one rectification and/or crystallization of the acrylic acid present in the liquid phase.

239. The process according to embodiment 238, wherein the crystallization is a suspension crystallization to obtain a crystal suspension comprising acrylic acid crystals.

240. The process according to embodiment 239, which is followed by a separation process in which the acrylic acid crystals are separated from the crystal suspension in a wash melt wash column.

241. The process according to embodiment 240, wherein the wash melt wash column is a hydraulic wash melt wash column.

242. The process according to any of embodiments 1 to 241, wherein the process for preparing acrylic acid is followed by a process for free-radical polymerization in which the acrylic acid prepared is polymerized to polymer with free-radical initiation as such and/or in the form of the conjugate Brønsted base thereof, and optionally in a mixture with other mono- and/or polyunsaturated compounds.

243. The process according to any of the embodiments 1 to 242, wherein the cobalt content of the poly-3-hydroxypropionate (removed in a separation zone A) in the thermolysis is 0 to 1% by weight.

244. The process according to any of the embodiments 1 to 243, wherein the cobalt content of the poly-3-hydroxypropionate in the thermolysis is $10^{-6}$ to 1% by weight.

245. The process according to any of the embodiments 1 to 244, wherein the cobalt content of the poly-3-hydroxypropionate in the thermolysis is $10^{-5}$ to 1% by weight.

246. The process according to any of the embodiments 1 to 245, wherein the cobalt content of the poly-3-hydroxypropionate in the thermolysis is $10^{-4}$ to 1% by weight.

247. The process according to any of the embodiments 1 to 246, wherein the cobalt content of the poly-3-hydroxypropionate in the thermolysis is 0.001 to 0.75% by weight.

248. The process according to any of the embodiments 1 to 247, wherein the cobalt content of the poly-3-hydroxypropionate in the thermolysis is 0.01 to 0.75% by weight.

249. The process according to any of the embodiments 1 to 248, wherein the cobalt content of the poly-3-hydroxypropionate in the thermolysis is 0.05 to 0.75% by weight.

250. The process according to any of the embodiments 1 to 249, wherein the cobalt content of the poly-3-hydroxypropionate in the thermolysis is 0.1 to 0.5% by weight.

251. The process according to any of the embodiments 1 to 242, wherein the cobalt content of the poly-3-hydroxypropionate in the thermolysis is ≤1% by weight.

252. The process according to any of the embodiments 1 to 242, wherein the cobalt content of the poly-3-hydroxypropionate in the thermolysis is ≤0.5% by weight.

253. The process according to any of the embodiments 1 to 242, wherein the cobalt content of the poly-3-hydroxypropionate in the thermolysis is ≤0.1% by weight.

254. The process according to any of the embodiments 1 to 242, wherein the cobalt content of the poly-3-hydroxypropionate in the thermolysis is ≤0.01% by weight.

255. The process according to any of the embodiments 1 to 242, wherein the cobalt content of the poly-3-hydroxypropionate in the thermolysis is ≤0.001% by weight.

256. The process according to any of the embodiments 1 to 242, wherein the cobalt content of the poly-3-hydroxypropionate in the thermolysis is ≤$10^{-5}$% by weight.

257. The process according to any of the embodiments 187 to 256, wherein the at least one organic active compound catalyzing the thermolysis as a splitting catalyst is pentamethyldiethylenetriamine.

258. The process according to any of the embodiments 187 to 256, wherein the at least one organic active compound catalyzing the thermolysis as a splitting catalyst is N,N,N',N'-tetramethyl-1,6-hexanediamine.

259. The process according to any of the embodiments 187 to 256, wherein the at least one organic active compound catalyzing the thermolysis as a splitting catalyst is bis(2-dimethylaminoethyl)ether.

260. The process according to any of the embodiments 187 to 256, wherein the at least one organic active compound catalyzing the thermolysis as a splitting catalyst is 2,2'-dimorpholinodiethyl ether.

261. The process according to any of the embodiments 187 to 256, wherein the at least one organic active compound catalyzing the thermolysis as a splitting catalyst is N,N-diethylethanolamine.

262. The process according to any of the embodiments 187 to 256, wherein the at least one organic active compound catalyzing the thermolysis as a splitting catalyst is N,N,N',N'-tetramethyl-1,3-propanediamine.

263. The process according to any of the embodiments 187 to 256, wherein the at least one organic active compound catalyzing the thermolysis as a splitting catalyst is N,N-dimethylcyclohexylamine.

264. The process according to any of the embodiments 187 to 256, wherein the at least one organic active compound catalyzing the thermolysis as a splitting catalyst is N,N-dimethyl-1,3-diaminopropane.

265. The process according to any of the embodiments 187 to 256, wherein the at least one organic active compound catalyzing the thermolysis as a splitting catalyst is N-methylimidazole.

266. The process according to any of the embodiments 187 to 256, wherein the at least one organic active compound catalyzing the thermolysis as a splitting catalyst is dimethylimidazole.

267. The process according to any of the embodiments 187 to 256, wherein the at least one organic active compound catalyzing the thermolysis as a splitting catalyst is 3-hydroxypyridine.

268. The process according to any of the embodiments 187 to 256, wherein the at least one organic active compound catalyzing the thermolysis as a splitting catalyst is 2-hydroxypyridine.

269. The process according to any of the embodiments 187 to 256, wherein the at least one organic active compound catalyzing the thermolysis as a splitting catalyst is 4-hydroxypyridine.

270. The process according to any of the embodiments 1 to 269, wherein the polydispersity Q of the poly-3-hydroxypropionate removed from the product mixture A (in the thermolysis zone A) is less than or equal to 2.0.

271. The process according to any of the embodiments 1 to 269, wherein the polydispersity of the poly-3-hydroxypropionate removed from the product mixture A (in the thermolysis zone A) is less than or equal to 1.5.

272. The process according to any of the embodiments 1 to 271, wherein the polydispersity of the poly-3-hydroxypropionate removed from the product mixture A (in the thermolysis zone A) is 1.2 to 2.
273. The process according to any of the embodiments 1 to 272, wherein the polydispersity Q of the poly-3-hydroxypropionate removed from the product mixture A (in the thermolysis zone A) is 1.5 to 1.8.
274. The process according to any of the embodiments 1 to 273, wherein the poly-3-hydroxypropionate removed from product mixture A (in thermolysis zone A) has a relative weight-average molecular weight of 3000 to 12 000.
275. The process according to any of the embodiments 1 to 274, wherein the poly-3-hydroxypropionate removed from product mixture A (in thermolysis zone A) has a relative weight-average molecular weight of 4000 to 10 000.
276. The process according to any of the embodiments 234 to 275, wherein the total amount of polymerization inhibitor added, based on the total amount of poly-3-hydroxypropionate present in the solid substance, or in the melt, or in the solution, or in the suspension, or in the emulsion, is 50 to 500 ppm by weight.
277. The process according to any of the embodiments 234 to 275, wherein the total amount of polymerization inhibitor added, based on the total amount of poly-3-hydroxypropionate present in the solid substance, or in the melt, or in the solution, or in the suspension, or in the emulsion, is 150 to 350 ppm by weight.
278. The process according to any of the embodiments 1 to 277, wherein the cobalt contents in the processes according to any of embodiments 243 to 256 are the total contents in the poly-3-hydroxypropionate of $Co^{+2}$.
279. The process according to any of the embodiments 1 to 278, wherein the cobalt contents in the processes according to any of embodiments 243 to 256 are the total contents in the poly-3-hydroxypropionate of $Co^{+1}$.
280. The process according to any of the embodiments 1 to 279, wherein the cobalt contents in the processes according to any of embodiments 243 to 256 are the total contents in the poly-3-hydroxypropionate of $Co^{0}$.
281. The process according to any of the embodiments 1 to 280, wherein the cobalt contents in the processes according to any of embodiments 243 to 256 are the total contents in the poly-3-hydroxypropionate of $Co^{-1}$.
282. The process according to any of the embodiments 1 to 281, wherein the aqueous precipitation liquid comprises at least one organic solvent other than an inorganic and/or organic acid.
283. The process according to any of the embodiments 1 to 282, wherein the aqueous wash liquid comprises at least one organic solvent other than an inorganic and/or organic acid.
284. The process according to embodiment 282 or 283, wherein the organic solvent is at least one organic solvent from the group consisting of methanol, ethanol, acetone, methyl ethyl ketone, dimethyl sulfoxide, N-methyl-2-pyrrolidone, formamide, N,N-dimethylformamide, tetrahydrofuran and 1,4-dioxane.

Examples and comparative examples (experiments "1" to "23")
(starting materials and analysis methods detailed and specified for the first time in each case for description of examples and comparative examples in experiments "1" to "23" were used in a corresponding manner at the corresponding point in subsequent experiments, unless explicitly stated otherwise; all precipitations and washes of poly-3-hydroxypropionate were conducted under air)

1. Noninventive preparation of poly-3-hydroxypropionate by carbonylating conversion of ethylene oxide dissolved in diglyme in the presence of a cobalt-comprising catalyst system (comparative example 1)

The carbonylating conversion was effected in an autoclave A stirrable with a paddle stirrer (the paddle stirrer was moved by means of magnetic coupling), the reaction space of which was optionally heatable or coolable from the outside. All surfaces in contact with the reaction space were manufactured from Hastelloy HC4. The reaction space of the autoclave had a circular cylindrical geometry. The height of the circular cylinder was 335 mm. The internal diameter of the circular cylinder was 107 mm. The shell of the reaction space had a wall thickness of 19 mm (Hastelloy HC4). The top of the autoclave was equipped with a gas inlet/gas outlet valve V which opened into the reaction space. The temperature in the reaction space was determined with the aid of a thermocouple. The reaction temperature was regulated under electronic control. The internal pressure in the reaction space was monitored continuously with an appropriate sensor.

The reaction space of the autoclave was at first inertized with argon (contents in the Ar: ≥99.999% by vol. of Ar, ≤2 ppm by vol. of $O_2$, ≤3 ppm by vol. of $H_2O$ and ≤0.5 ppm by vol. of total amount of hydrocarbons).

Subsequently, the autoclave A at a controlled temperature of 10° C. was charged under argon with 8.2 g of dicobalt octacarbonyl ($Co_2(CO)_8$; supplier: Sigma-Aldrich; specification: 1-10% hexane, ≥90% Co, catalog number: 60811), 4.4 g of 3-hydroxypyridine (supplier: Sigma-Aldrich; specification: 99% content, catalog number: H57009) and 802.4 g of diglyme (supplier: Sigma-Aldrich; specification: 99% content, catalog number: M1402), and the autoclave was subsequently closed. The temperature of the two solids was 25° C. and the temperature of the diglyme was 10° C. Then, while maintaining the internal temperature of 10° C., carbon monoxide was injected into the autoclave through the valve V until the pressure in the reaction space was $1.5 \cdot 10^6$ Pa (carbon monoxide from BASF SE, specification: 99.2% CO). Subsequently, the temperature in the reaction space was increased to 35° C. in order to verify the integrity of the autoclave A (over a period of 90 min). Then the atmosphere in the reaction space was decompressed to an internal pressure of $10^6$ Pa by opening the valve V. The temperature in the interior thereafter was 30° C.

Subsequently, 51.0 g of ethylene oxide (1.5 g/min) were pumped through the valve V into the reaction space (supplier: BASF SE; specification: 99.9% purity). This reduced the temperature in the reaction space to 25° C. Thereafter, carbon monoxide was again injected into the autoclave until the pressure in the reaction space reached $6 \cdot 10^6$ Pa (while maintaining the internal temperature of 25° C.).

Then, while stirring (700 rpm), the temperature in the reaction space of autoclave A was increased in an essentially linear manner to 75° C. within 45 min. This temperature was maintained while stirring for 8 h. The pressure in the reaction space fell to $5 \cdot 10^6$ Pa within this period. Then the heating of autoclave A was switched off. Within 5 h and 50 min, the temperature in the stirred reaction space cooled down in an essentially exponential manner to 25° C. (after 50 min the internal temperature had fallen to 60° C., after 150 min to 40° C. and after 235 min to 30° C.). The corresponding pressure in the reaction space was $4.3 \cdot 10^6$ Pa. Then autoclave A was decompressed to standard pressure and the reaction space was purged with argon ($10^6$ Pa) three times in succession.

In the reaction space were 860.2 g of a dark red/brown solution as product mixture A. It was withdrawn from the autoclave and then left to stand in a closed glass flask in a cooling space at a temperature of 7° C. for 12 h. The poly-3-hydroxypropionate which precipitated out was filtered off and the filtercake was washed with 252 g of methanol (supplier: BASF SE; specification: 99.8% purity). The methanol was at a temperature of 25° C. and was sucked through the filtercake. The filtercake thus washed was then dried under reduced pressure for 10 h (10 hPa, drying temperature: 25° C.).

The 8.1 g of poly-3-hydroxypropionate which had thus been removed from product mixture A as the first fraction still comprised, based on the weight of the mass thereof, 2.8% by weight of Co (the starting weight content of Co in product mixture A, based on the weight of the theoretically maximum possible amount of poly-3-hydroxypropionate formed, was 3.39% by weight).

The weight-average relative molecular weight $M_W$ thereof was 7270 ($\triangleq$ a weight-average molar mass of 7270 g/mol).

The filtrate obtained in the course of removal of the poly-3-hydroxypropionate by filtration was analyzed by gas chromatography (for which a Hewlett Packard gas chromatograph (HP model 5890 series II) with a flame ionization detector was used). It comprised (reported as area percent of the total area of the GC peaks) 0.7% ethylene oxide, 97.1% diglyme, 0.2% of the β-propiolactone by-product and 0.3% of the succinic anhydride by-product.

The material was combined with the methanol which had been sucked through in the course of washing of the poly-3-hydroxypropionate which had been filtered off. The mixture thus produced was left to stand in a cooling space at a temperature of 7° C. for 12 h. The poly-3-hydroxypropionate which precipitated out was filtered off again and the resulting filtercake was washed with 250 g of methanol. The methanol was at a temperature of 25° C. and was sucked through the filtercake. The washed filtercake was dried again at 10 hPa and 25° C. for 10 h.

The amount of the poly-3-hydroxypropionate thus removed from product mixture A as the second fraction was 18.7 g. Based on the weight of the mass thereof, it still comprised 1.1% by weight of Co. The weight-average relative molecular weight $M_W$ thereof was 5190 ($\triangleq$ a weight-average molar mass of 5190 g/mol).

A total of 26.8 g of poly-3-hydroxypropionate was removed from product mixture A. This is 32.1% of the theoretically possible maximum yield.

The cobalt contents were determined by inductively coupled plasma atomic emission spectroscopy (ICP-OES).

The instrument used was a Varian 720-ES ICP-OES spectrometer. The wavelength of the spectral line of Co used for analysis was 237.86 nm.

For sample preparation, 0.1 g of the sample to be analyzed in each case was converted to ash with a mixture of concentrated sulfuric acid, concentrated nitric acid and concentrated perchloric acid (as strongly oxidizing acids) (using temperatures of up to 320° C., the acids were quantitatively fumed off). The remaining residue was taken up in concentrated hydrochloric acid and dissolved with heating and addition of water. The resulting solution was subsequently analyzed.

The molecular weights were determined by size exclusion chromatography (SEC/GPC). The elution curve was converted to the actual distribution curve with the aid of polymethyl methacrylate (PMMA) calibration curves. The calibration was effected with narrow-distribution PMMA standards, the relative molecular weights of which were within the range from M=800 to M=1 820 000. The values outside this elution range were extrapolated.

2. Noninventive preparation of poly-3-hydroxypropionate by carbonylating conversion of ethylene oxide dissolved in diglyme in the presence of a cobalt-comprising catalyst system (comparative example 2).

The procedure was as in comparative example 1, but with the following differences:
the use amount of dicobalt octacarbonyl was 16.0 g;
the use amount of 3-hydroxypyridine was 8.7 g;
the use amount of diglyme was 1001.2 g;
the use amount of ethylene oxide was 97.8 g;
the integrity test of the autoclave extended only over 50 min and was effected at a temperature increased to 28° C. in the reaction space;
the ethylene oxide was supplied while maintaining the 28° C. in the reaction space, as was the final carbon monoxide ($6 \cdot 10^6$ Pa);
at the end of the reaction time of 8 h, the pressure in the reaction space of the autoclave was $3 \cdot 10^6$ Pa;
the cooling to 25° C. extended over a period of 6 h;
the internal temperature of 60° C. had been attained after 66 min;
the internal temperature of 40° C. had been attained after 165 min;
the internal temperature of 30° C. had been attained after 255 min;
the pressure in the reaction space on attainment of 25° C. was $2.8 \cdot 10^6$ Pa;
in the reaction space were 1106.3 g of a dark red/brown solution as product mixture A.

Product mixture A was left to stand in a closed glass flask in a cooling space at a temperature of 7° C. for 12 h. The poly-3-hydroxypropionate which precipitated out was filtered off and the filtercake was washed with 300 g of methanol at a temperature of 25° C. The washed filtercake was dried for 10 h (10 hPa, 25° C.). 41.1 g of poly-3-hydroxypropionate thus removed from product mixture A (first fraction) still comprised, based on the weight of the mass thereof, 1.6% by weight of cobalt (the starting weight content of Co in product mixture A, based on the weight of the maximum possible amount of poly-3-hydroxypropionate formed, was 2.97% by weight). The weight-average relative molecular weight was $M_W$=7220.

The filtrate obtained in the removal of the poly-3-hydroxypropionate by filtration was analyzed by gas chromatography. It comprised (reported as area percent of the total area of the GC peaks) 0.9% ethylene oxide, 92.7% diglyme, 1.0% of the β-propiolactone by-product and 0.6% of the succinic anhydride by-product.

The material was combined with the methanol which had been sucked through in the course of washing of the poly-3-hydroxypropionate which had been filtered off (first fraction). The mixture thus obtained was left to stand in a cooling space at a temperature of 7° C. for 12 h. The poly-3-hydroxypropionate which precipitated out was filtered off again and the resulting filtercake was washed with 300 g of methanol at a temperature of 25° C. (as always, the methanol was sucked through the filtercake). The washed filtercake was dried again at 10 hPa and 25° C. for 10 h.

The mass of the poly-3-hydroxypropionate separated in this way from product mixture A as the second fraction was 88.0 g. Based on the weight of the mass thereof, it still comprised 1.6% by weight of cobalt. The weight-average relative molecular weight $M_W$ thereof was 5640.

The filtrate obtained in the removal of the second fraction of poly-3-hydroxypropionate by filtration was combined with the methanol sucked through in the course of washing of the second fraction of poly-3-hydroxypropionate. The mixture thus obtained was left to stand in a cooling space at a temperature of 7° C. for 12 h. The poly-3-hydroxypropionate obtained was filtered off again (third fraction) and the resulting filtercake was washed with 300 g of methanol at a temperature of 25° C. The washed filtercake was dried again at 10 hPa and 25° C. for 10 h.

The mass of the poly-3-hydroxypropionate removed in this way as the third fraction from product mixture A was 5.8 g. Based on the weight of the mass thereof, it still comprised 1.8% by weight of cobalt. The weight-average relative molecular weight $M_W$ thereof was 5240.

The filtrate obtained in the removal of the third fraction of poly-3-hydroxypropionate by filtration was combined with the methanol sucked through in the course of washing of the third fraction of poly-3-hydroxypropionate. The resulting mixture was left to stand in a cooling space at a temperature of 7° C. for 12 h. The poly-3-hydroxypropionate which precipitated out was filtered off again (fourth fraction) and the resulting filtercake was washed with 300 g of methanol at a temperature of 25° C. The washed filtercake was dried again at 10 hPa and 25° C. for 10 h.

The mass of the poly-3-hydroxypropionate thus removed from product mixture A as the third fraction was 5.3 g. Based on the weight of the mass thereof, it comprised 2.7% by weight of cobalt. The weight-average relative molecular weight $M_W$ thereof was 4230.

The elevated cobalt content of the third fraction is attributed to the fact that cobalt which was previously still dissolved now apparently also precipitates as a separate cobalt salt in the resulting solvent mixture.

A total of 140.2 g of poly-3-hydroxypropionate were removed from product mixture A. This is 87.6% of the theoretically possible maximum yield.

3. Noninventive preparation of poly-3-hydroxypropionate by carbonylating conversion of ethylene oxide dissolved in diglyme in the presence of a cobalt-comprising catalyst system (comparative example 3)

The carbonylating conversion was effected in an autoclave B stirrable with a stirrer bar (the stirrer bar was moved by means of magnetic coupling), the reaction space of which was optionally heatable or coolable from the outside. All surfaces in contact with the reaction space were manufactured from Hastelloy HC4. The reaction space of the autoclave had a circular cylindrical geometry. The height of the circular cylinder was 90 mm. The internal diameter of the circular cylinder was 59.1 mm. The shell of the reaction space had a wall thickness of 15.5 mm (Hastelloy HC4).

The top of the autoclave was equipped with a gas inlet/gas outlet valve V which opened into the reaction space. The temperature in the reaction space was determined with the aid of a thermocouple. The reaction temperature was regulated under electronic control. The internal pressure in the reaction space was monitored continuously with an appropriate sensor. The specifications of corresponding feedstocks corresponded to those from comparative example 1.

First of all, the reaction space of the autoclave was inertized with molecular nitrogen (contents of the $N_2$: ≥99.99% by vol. of $N_2$, ≤20 ppm by vol. of $O_2$ and ≤5 ppm by vol. of $H_2O$).

Subsequently, the autoclave B at a controlled temperature of 10° C. was charged under $N_2$ with 1.58 g of dicobalt octacarbonyl, 0.87 g of 3-hydroxypyridine and 88.10 g of diglyme, and autoclave B was subsequently closed. The temperature of the two solids was 25° C. and the temperature of the diglyme was 10° C. Then, while maintaining the internal temperature of 10° C., carbon monoxide was injected into the autoclave through the valve V until the pressure in the reaction space was $1.5 \cdot 10^6$ Pa. Subsequently, the temperature in the reaction space was increased to 25° C. in order to verify the integrity of autoclave B (over a period of 30 min). Then the atmosphere in the reaction space of autoclave B was decompressed to $2 \cdot 10^5$ Pa by opening valve V. Subsequently, 11.66 g of ethylene oxide (0.3 g/min) were pumped into the reaction space through valve V. Thereafter, the temperature in the reaction space was 19° C. Finally, carbon monoxide was injected again into the autoclave until the pressure in the reaction space reached $6 \cdot 10^6$ Pa (at an internal temperature of 19° C.). Then the temperature in the reaction space of autoclave B was increased in an essentially linear manner to 75° C. while stirring (700 rpm) within 45 min. This temperature was maintained while stirring for 4 h. Then the heating of autoclave B was switched off and the autoclave (without stirring in the reaction space) was cooled to 0° C. in ice-water. Then autoclave B was decompressed to standard pressure and product mixture A was outgassed by leaving it to stand without stirring for 30 minutes. Thereafter, the reaction space of autoclave B was purged with molecular nitrogen ($10^6$ Pa) three times in succession. The temperature of 0° C. in the reaction space of autoclave B was maintained at a constant level over the entire period.

Product mixture A present in the reaction space was a red-brown suspension (106.8 g). The poly-3-hydroxypropionate which had precipitated out at the comparatively low temperature of 0° C. was filtered off and washed with 60 g of methanol (the methanol was at a temperature of 0° C. and was sucked through the filtercake). The methanolic wash solution was discarded. The washed filtercake was dried under reduced pressure for 10 h (10 hPa, drying temperature: 25° C.). The 5.7 g of poly-3-hydroxypropionate which had thus been removed from product mixture A still comprised, based on the weight of the mass thereof, 1.95% by weight of cobalt (the starting weight content of Co in product mixture A, based on the weight of the theoretically maximum possible amount of poly-3-hydroxypropionate formed, was 2.83% by weight).

The filtrate obtained when the poly-3-hydroxypropionate was removed from product mixture A by filtration was analyzed by gas chromatography. It comprised (reported as area percentages of the total area of the GC peaks) 0.5% ethylene oxide, 92.7% diglyme, 0% β-propiolactone and 0.8% of the succinic acid by-product.

4. Noninventive preparation of poly-3-hydroxypropionate by carbonylating conversion of ethylene oxide dissolved in diglyme in the presence of a cobalt-comprising catalyst system (comparative examples 4a, 4b and 4c)

Comparative example 3 was repeated twice and the two filtrates obtained in the filtration of the precipitated poly-3-hydroxypropionate from the respective product mixture A were combined to give an overall filtrate.

Four identical portions each of 30 g were taken from the overall filtrate. The fourth portion formed the basis for example 1 of this document. The other three portions of the overall filtrate were each admixed with 16 g of one of the following precipitation liquids PL each at a temperature of 25° C.: methanol (=comparative example 4a), cyclohexane (supplier: Sigma-Aldrich; specification: ≤0.01% water (Karl Fischer), ≤0.001% nonvolatile substances; catalog number: 34496) (=comparative example 4b) and tert-butyl methyl ether=methyl tert-butyl ether (MTBE) (supplier: Sigma-Aldrich; specification: <0.003% water, 99.8% content; catalog number: 306975) (=comparative example 4c). The resulting mixture was left to stand in a cooling space at a temperature of 7° C. for 12 h.

The poly-3-hydroxypropionate which precipitated out in each case was filtered off and the filtercake resulting in each case was washed in each case with 20 g of the appropriate precipitation liquid as wash liquid (the wash liquid was sucked through the filtercake at a temperature of 25° C. in each case). The washed filtercake was dried at 10 hPa and 25° C. for 10 h.

Table 2 below shows, as a function of the precipitation liquid PL used, the mass of the poly-3-hydroxypropionate (P3HP) removed in each case, the amount of cobalt still present (in % by weight) based on the weight of this mass, and the respective corresponding relative weight-average molecular weight $M_W$. In addition, table 2 also shows the color of the poly-3-hydroxypropionate removed in each case.

TABLE 2

| CEx. | PL | Co (% by wt.) | P3HP (g) | Color P3HP | $M_W$ |
|---|---|---|---|---|---|
| 4a | methanol | 1.7 | 1.9 | light brown | 4085 |
| 4b | cyclohexane | 3.5 | 2.9 | pink-brown | 4221 |
| 4c | MTBE | 4.6 | 2.2 | red-brown | 4719 |

To determine the end groups present and the structure of the solids removed, these in the case of use of methanol as the precipitation liquid were analyzed both by mass spectrometry with matrix-assisted laser desorption/ionization (MALDI-MS) and by gel permeation chromatography-mass spectrometry (GPC-MS).

For the MALDI-MS analysis, the sample to be analyzed was first dissolved completely in aqueous acetonitrile (50% by volume of water, 50% by volume of acetonitrile) and then applied to a MALDI steel target with 2,5-dihydroxybenzoic acid and sodium trifluoroacetate as matrix substances (both likewise dissolved in aqueous acetonitrile), and the solvent was removed. A nitrogen laser (pulse time 3 ns, wavelength=337 nm) was used to vaporize and ionize the analyte from the steel target in a mixture with the matrix.

The GPC-MS analysis proceeded from an extract of the sample to be analyzed in tetrahydrofuran (THF) (the sample did not dissolve fully in THF), the dissolved constituents of which were separated by means of GPC prior to the MS analysis thereof. The ionization was effected by means of electrospray ionization (ESI).

The following structures/end groups were assigned:

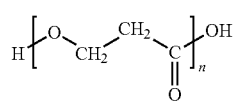

(Structure 1)

where n = 8 to 40;

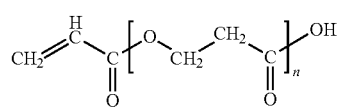

(Structure 2)

where n = 9 to 27;

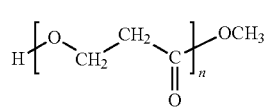

and (Structure 3)

where n = 10 to 38;

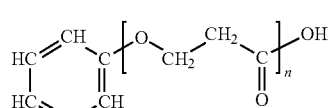

(Structure 4)

where n = 9 to 29.

Quantitative determinations of the above structures were effected by means of $^1$H NMR spectroscopy on a Bruker DPX 400/1 FT-NMR spectrometer at a $^1$H carrier frequency of 400 MHZ.

The sample concentration was 5 mg of poly-3-hydroxypropionate dissolved in 1 ml of $CDCl_3$. The width of the excitation pulse was 8012.82 Hz. The sample temperature in the course of recording of the spectra was always 26.8° C. For excitation, a sequence of 30° pulses was used. 32 individual recordings in each case were accumulated to give the resulting spectrum.

The result was that the sample analyzed consisted to an extent of ≥99% by weight of structure 1. The protons of the vinyl group in structure 2 were visible by their $^1$H NMR signal.

$^1$H NMR signals of aromatic protons of structure 4 were undetectable.

This result is attributed particularly to traces of water still present in the reaction mixture.

5. Inventive preparation of poly-3-hydroxypropionate by carbonylating conversion of ethylene oxide dissolved in diglyme in the presence of a cobalt-comprising catalyst and washing of poly-3-hydroxypropionate removed with water (example 1).

The fourth portion (30 g) of the overall filtrate from comparative example 4 was admixed with 16 g of water (at a temperature of 25° C.) and the resulting aqueous mixture was left to stand in a cooling space at a temperature of 7° C. for 12 h.

The poly-3-hydroxypropionate obtained was filtered off and the resulting filtercake was washed with 20 g of water (the water was sucked through the filtercake at a temperature of 25° C.). The washed filtercake was dried at 10 hPa and 60° C. for 72 h.

Table 3 below shows the properties of the poly-3-hydroxypropionate removed in this way from the product mixture A thereof, determined by the analysis methods already described.

TABLE 3

| Ex. | PL | Co (% by wt.) | P3HP (g) | Color P3HP | $M_W$ |
|---|---|---|---|---|---|
| 1 | water | 0.7 | 2.2 | pale orange/cream | 5598 |

The results show that water is a wash liquid of particular suitability for the purpose of decobaltizing the poly-3-hydroxypropionate removed from a product mixture A.

6. Inventive preparation of poly-3-hydroxypropionate by carbonylating conversion of ethylene oxide dissolved in diglyme in the presence of a cobalt-comprising catalyst and washing of poly-3-hydroxypropionate removed with an aqueous acetic acid solution (example 2)

Comparative example 2 was repeated several times and various fractions removed were mixed to obtain a poly-3-hydroxypropionate which still comprised 2% by weight of Co based on the weight of the mass thereof.

An 80 g sample of this poly-3-hydroxypropionate was washed with 658 g of a 12.5% by weight solution of acetic acid in water (the temperature of the acetic acid solution was 25° C.; it was sucked through the P3HP).

It was subsequently washed with 200 g of water (temperature=25° C.) and then with 200 g of methanol (temperature=25° C.), and the remaining solids were dried at 10 hPa and 25° C. for 10 h.

The cobalt content of the poly-3-hydroxypropionate thus obtained was 0.2% by weight.

The weight-average molecular weight prior to the wash was $M_W$=5930, and after the wash $M_W$=5810.

Analysis of the melting characteristics (this was effected by the method of dynamic differential calorimetry (DSC) on a Q2000 differential calorimeter from TA (Thermal Analysis) Instruments; the amount of sample was 8.2 mg each time and the heating/cooling rate was 20 K/min) gave a melting range of 65.7° C. to 79° C. for the P3HP prior to the wash, and of 65.4° C. to 71.6° C. after the wash.

The elemental analysis of the P3HP (which was effected on the basis of the full combustion of the respective sample with subsequent gas chromatography analysis of the combustion products using a CHN analyzer from Elementar Analysensysteme GmbH of the vario EL cube type, and on an O analyzer from EuroVektor of the EA type) gave (figures in % by weight):

C: 47.8%;
O: 42.6%;
H: 5.6%; and
N: 0.5%.

After the wash, the corresponding elemental analysis gave:

C: 49.3%;
O: 43.5%;
H: 5.7%; and
N: <0.5%.

Structure and end group analysis by means of MALDI-MS and GPC-MS gave the following assignments for the washed P3HP:

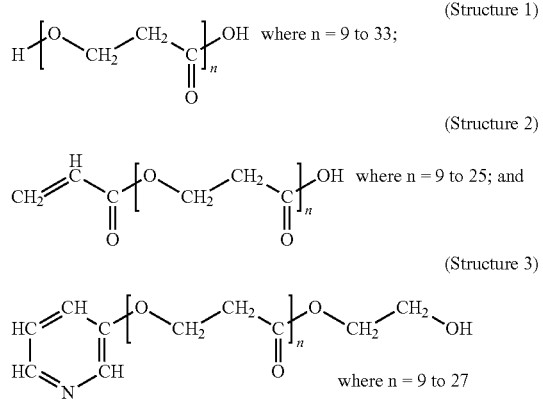

(Structure 1) where n = 9 to 33;
(Structure 2) where n = 9 to 25; and
(Structure 3) where n = 9 to 27

Quantitative determinations of the above structures were effected by the $^1$H NMR method already described.

The result was that the analyzed sample consisted to an extent of ≥99% of structure 1. Protons of the vinyl group in structure 2 were visible by their $^1$H NMR signal. As were the protons of the ethylene glycol end groups. $^1$H NMR signals of aromatic protons of structure 3 were undetectable.

7. Inventive preparation of poly-3-hydroxypropionate by carbonylating conversion of ethylene oxide dissolved in diglyme in the presence of a cobalt-comprising catalyst system and precipitation thereof using an aqueous acetic acid solution as the precipitation liquid (example 3)

Comparative example 3 was repeated. The 106.8 g of the red-brown aqueous suspension obtained as product mixture A were, however, admixed with 534 g of a 12.5% by weight solution of acetic acid in water, the temperature of which was 50° C. The resulting aqueous mixture, while sparging with air (25° C., 5 l/h), was stirred (700 rpm) at a temperature of 45° C. for 1 h. In the course of this, the color changed. The hue of the liquid phase changed to pale pink, and the color of the solid suspended therein to cream.

The poly-3-hydroxypropionate suspended in the suspension was filtered off and dried under reduced pressure for 72 h (10 hPa, drying temperature: 60° C.).

The 18 g of poly-3-hydroxypropionate removed in this way from product mixture A comprised, based on the weight of the mass thereof, only 0.05% by weight of cobalt. The corresponding relative weight-average molecular weight $M_W$ was 5120. The 18 g of poly-3-hydroxypropionate removed are 94% of the theoretically possible maximum yield.

8. Inventive preparation of poly-3-hydroxypropionate by carbonylating conversion of ethylene oxide dissolved in diglyme in the presence of a cobalt-comprising catalyst system and precipitation thereof using an aqueous acetic acid solution as the precipitation liquid (example 4)

Comparative example 3 was repeated. Instead of 0.87 g of 3-hydroxypyridine, however, 0.78 g of pyridine was used as the sole cocatalyst B. In addition, the amount of ethylene oxide used was only 10.07 g.

The 103.6 g of the aqueous suspension obtained as product mixture A (red-brown liquid phase with orange-red solid) were admixed with 518 g of a 12.5% by weight solution of acetic acid in water, the temperature of which was 50° C. The resulting aqueous mixture, while sparging with air (25° C., 5 l/h), was stirred (700 rpm) at a temperature of 45° C. for 1 h. In the course of this, the color changed. The hue of the liquid phase turned pale pink, and the color of the solid suspended therein turned cream.

The poly-3-hydroxypropionate suspended in the suspension was filtered off and dried under reduced pressure for 72 h (10 hPa, drying temperature: 60° C.).

The 8.0 g of poly-3-hydroxypropionate removed in this way from product mixture A comprised, based on the weight of the mass thereof, only 0.12% by weight of cobalt. The corresponding relative weight-average molecular weight $M_W$ was 4022. The 8.0 g of poly-3-hydroxypropionate removed are 48.7% of the theoretically possible maximum yield.

9. Noninventive preparation of poly-3-hydroxypropionate by carbonylating conversion of ethylene oxide dissolved in diglyme in the presence of a cobalt-comprising catalyst system (comparative examples 5a, 5b, 5c and 5d)

Comparative example 2 was repeated, except with the following slight differences:

the use amount of dicobalt octacarbonyl was 16.1 g;
the use amount of diglyme was 944.1 g;
the use amount of ethylene oxide was 99.8 g.

In the reaction space in each case were approx. 1112.1 g of a dark red/brown solution as product mixture A.

Four identical portions each of 250 g were taken from this product mixture A.

The first portion was left to stand in a cooling space at a temperature of 7° C. for 12 h. The poly-3-hydroxypropionate which precipitated out was filtered off and the resulting filtercake was dried at 10 hPa and 60° C. for 10 h (=comparative example 5a).

The second portion was admixed with 75 g of methanol (25° C.) as a precipitation liquid and the resulting mixture was left to stand in a cooling space at a temperature of 7° C. for 12 h.

The poly-3-hydroxypropionate which precipitated out was filtered off and the resulting filtercake was dried at 10 hPa and 60° C. for 10 h (=comparative example 5b).

In comparative example 5c, the procedure was as in comparative example 5b, except that the filtercake, prior to the drying thereof, was washed with 50 g of methanol, the temperature of which was 60° C. (the methanol was sucked through the filtercake).

In comparative example 5d, the procedure was as in comparative example 5c, except that the amount of the methanol wash liquid used was 75 g.

Table 4 below shows, for the respective comparative example, the mass of poly-3-hydroxypropionate (P3HP) removed in each case, the amount of Co still present based on the weight of this mass (in % by weight) and the corresponding relative weight-average molecular weight $M_W$ in each case, and also the corresponding polydispersity Q. In addition, table 4 also shows the color of the poly-3-hydroxypropionate removed in each case.

TABLE 4

| Comp. Ex. | Co (% by wt.) | P3HP (g) | Color P3HP | $M_W$ (Q) |
|---|---|---|---|---|
| 5a | 3.0 | 3.4 | red-brown | 6221 (1.9) |
| 5b | 2.5 | 22.4 | dusky pink-brown | 6610 (1.8) |
| 5c | 2.2 | 21.5 | dusky pink | 6742 (1.8) |
| 5d | 1.8 | 18.6 | sand | 7584 (1.9) |

10. Inventive preparation of poly-3-hydroxypropionate by carbonylating conversion of ethylene oxide dissolved in diglyme in the presence of a cobalt-comprising catalyst system and using an aqueous acetic acid solution as precipitation liquid (example 5)

Comparative example 5a was repeated, except that 50 g of a 12.5% by weight solution of acetic acid in water were also added to the 250 g of product mixture A before the resulting mixture was left to stand for 12 h in a cooling space at a temperature of 7° C. The precipitated poly-3-hydroxypropionate was filtered off and the resulting filtercake was washed with 50 g of methanol (this was at a temperature of 25° C. and was sucked through the filtercake).

Table 5 below shows the mass of the poly-3-hydroxypropionate (P3HP) removed, the amount of cobalt still present based on the weight of this mass (in % by weight), the corresponding relative weight-average molecular weight $M_W$ and the corresponding polydispersity Q. In addition, table 5 also shows the color of the poly-3-hydroxypropionate removed.

TABLE 5

| Ex. | Co (% by wt.) | P3HP (g) | Color P3HP | $M_W$ (Q) |
|---|---|---|---|---|
| 5 | 0.76 | 19.9 | pale pink | 6651 (1.6) |

11. Inventive preparation of poly-3-hydroxypropionate by carbonylating conversion of ethylene oxide dissolved in diglyme in the presence of a cobalt-comprising catalyst system and using various aqueous solutions as precipitation and wash liquids (examples 6a, 6b, 6c and 6d)

Comparative example 5 was repeated identically and four identical portions each of 250 g were taken from the resulting product mixture A.

Each portion was admixed with 75 g of an aqueous precipitation liquid and the mixture resulting in each case was left to stand in a cooling space at a temperature of 7° C. for 12 h.

The poly-3-hydroxypropionate which precipitated out in each case was filtered off and the resulting filtercake was washed with 75 g of the liquid type used as the precipitation liquid (the temperature of the wash liquid was 25° C. in each case; the wash liquid was sucked through the filtercake in each case).

Finally, the washed filtercake was dried in each case at 10 hPa and 60° C. for 72 h. Table 6 below shows the aqueous precipitation/wash liquid PL used for the respective example, the mass of the poly-3-hydroxypropionate (P3HP) removed in each case, the amount of cobalt still present based on the weight of this mass (in % by weight) and the respective corresponding relative weight-average molecular weight $M_W$, and also the respective polydispersity Q. In addition, table 6 also shows the color of the poly-3-hydroxypropionate removed in each case.

TABLE 6

| Ex. | PL | Co (% by wt.) | P3HP (g) | Color P3HP | $M_W$ (Q) |
|---|---|---|---|---|---|
| 6a | water | 1.1 | 23.4 | cream-beige | 5684 (1.8) |
| 6b | 15% by weight aqueous acetic acid solution | 0.3 | 22.3 | pink | 6141 (1.7) |
| 6c | 15% by weight aqueous ammonia solution | 1.0 | 16.2 | raspberry red | 4052 (1.7) |
| 6d | 2% by weight aqueous solution of tetrasodium ethylenediamine-tetraacetate | 1.0 | 10.2 | green-brown | 6653 (1.7) |

12. Noninventive preparation of poly-3-hydroxypropionate by ring-opening polymerization of β-propiolactone in the absence of cobalt (comparative example 6; the synthesis was based on U.S. Pat. No. 4,357,462 A and on "Die Polymerisation von Lactonen, Teil 1: Homopolymerisation 4-, 6- and 7-gliedriger Lactone mit kationischen Initiatoren" in "Die Makromolekulare Chemie—New York—Hüthig & Wepf Verlag, Vol. 56, 1962, pages 179 ff")

1 ml of boron trifluoride etherate (=catalyst; $BF_3 \times (CH_3$—$CH_2$—O—$CH_2$—$CH_3)_2$; supplier: Fluka; specification: purum, catalog number: 15719) was dissolved in 300 ml of methylene chloride (=solvent; supplier: BASF SE; specification: purity 98-100%) which had been stored over molecular sieve (3 Å) as a desiccant (in a glass 3-neck flask with capacity 750 ml, magnetic stirring was effected, the internal temperature was 20° C.).

A silicone oil bath was used to bring the solution to boiling (at standard pressure). Subsequently, 24.9 g of β-propiolactone (supplier: Alfa Aesar; specification: 97%, catalog number: B23197, LOT 10140573) were continuously added dropwise to the solution boiling under reflux within 20 min while stirring.

After addition had ended, the reaction mixture was kept under reflux for another 8 h while stirring. During the progressing reaction, the solution changed color from colorless through yellow to orange.

Thereafter, the solvent was removed by distillation while stirring under reduced pressure and at an oil bath temperature of 65° C. within 30 min.

There remained 27.2 g of an orange oil which was cooled to 25° C. and solidified in the manner of a wax at this temperature. To remove the catalyst system, 400 ml of methanol (25° C.) were added, the temperature of the mixture was warmed to 50° C. and the mixture was stirred at this temperature for 1 h and 50 min until the solids had dissolved completely. Then the solution was cooled again to 25° C., and a colorless solid precipitated out.

This was filtered off and the filtercake was washed twice in succession with 10 ml of methanol each time (the temperature of the methanol was 25° C.; the methanol was sucked through the filtercake) and then dried at 25° C. and 10 hPa for 8 h. There remained 12.4 g of a colorless powder. The weight-average relative molecular weight $M_W$ thereof was 3000, with a polydispersity Q of 1.4.

The corresponding $^1$H and $^{13}$C NMR spectra and the ATR-FT-IR spectrum corresponded to poly-3-hydroxypropionate having a purity of >95% by weight.

The $^1$H and $^{13}$C NMR spectra were recorded on a Bruker DRX 500 FT-NMR spectrometer on solutions of poly-3-hydroxypropionate in $CDCl_3$. The magnetic field strength corresponded to a $^1$H carrier frequency of 500 MHz.

The ATR infrared spectra were recorded with a Bruker Vertex 70 spectrometer with ATR ("attenuated total reflection") and the method of FT-IR spectroscopy. The solid poly-3-hydroxypropionate was analyzed. For this purpose, the samples were additionally dried at 60° C. and 10 hPa for 12 h and then finely pulverized to enable optimal contact with the ATR crystal (in which total reflection proceeded).

13. Noninventive preparation of poly-3-hydroxypropionate by ring-opening polymerization of β-propiolactone in the absence of cobalt (comparative example 7; the synthesis was based on U.S. Pat. No. 4,357,462 A and on "Die Polymerisation von Lactonen, Teil 1: Homopolymerisation 4-, 6- and 7-gliedriger Lactone mit kationischen Initiatoren" in "Die Makromolekulare Chemie—New York—Hüthig & Wepf Verlag, Vol. 56, 1962, pages 179 ff")

0.5 mg of titanium tetrachloride (=catalyst; supplier: Acros, specification: 99.9%, catalog number: 197231000) was dissolved in 150 ml of toluene (=solvent; supplier: BASF SE; specification: 99.9%) which had been stored over molecular sieve (3 Å) as a desiccant (in a glass 3-neck flask with capacity 250 ml, magnetic stirring was effected, the internal temperature was 20° C.).

5 g of β-propiolactone were added dropwise while stirring to the orange solution obtained at a sufficiently slow rate that the temperature of the reaction solution did not rise above 25° C. After the addition had ended, the reaction mixture was heated to 80° C. with a silicone oil bath while stirring and kept at this temperature for 1 h, in the course of which a second orange liquid oily phase formed. The temperature of the reaction mixture was increased to 100° C. and the mixture was stirred at this temperature for a further 4 h. Then the mixture was cooled to 25° C., in the course of which the separated orange oily phase solidified in the manner of a wax.

The liquid toluene phase was removed from the wax by decanting, and discarded. Then 100 ml of methanol (25° C.) were added to the orange wax as a separating agent, and the mixture was heated to 50° C. and stirred at this temperature for 1 h until the solid had dissolved completely. Finally, the solution was cooled again to 25° C., in the course of which a beige solid precipitated out.

This was filtered off and washed twice in succession with 10 ml of methanol (25° C.) each time (the methanol was sucked through the filtercake).

The remaining filtercake was dried at 60° C. and 300 Pa for 60 h. There remained 3.4 g of a pale yellowish powder. The weight-average relative molecular weight $M_W$ thereof was 7200, with a polydispersity Q of 1.8.

The corresponding $^1$H and $^{13}$C NMR spectra and the ATR-FT-IR spectrum corresponded to poly-3-hydroxypropionate having a purity of >95% by weight.

14. Thermolysis of the poly-3-hydroxypropionate (P3HP) not prepared in accordance with the invention from comparative example 6 (comparative example 8)

a) The splitting apparatus manufactured from glass (thermolysis zone A) consisted of a round-bottomed splitting flask (capacity 25 ml, three necks), atop which was a distillation system with thermometer, Liebig condenser, a product flask (capacity 10 ml, one neck) and a hose connection for offgas, which was open to the atmosphere.

3.0 g of the poly-3-hydroxypropionate from comparative example 7 were weighed into the round-bottomed splitting flask. Through the second neck of the splitting flask, a stream of molecular nitrogen (≥99.9% by vol. of $N_2$; flow rate: 1.4 l/h; temperature: 25° C.) was supplied thereto as stripping gas over the full course of the thermolysis. This flowed through the splitting apparatus and left it again as part of the offgas which was conducted out of it through a cold trap, the temperature of which was kept at −78° C., via the offgas hose. The splitting flask filled with the P3HP was lowered down to the middle neck into a silicone oil bath preheated to 180° C. and heated by the oil bath at a working pressure of $1.0133 \cdot 10^5$ Pa (standard pressure). A magnetic stirrer was used to stir the contents of the splitting flask.

As the temperature in the splitting flask reached 60° C., the P3HP began to melt.

As the internal temperature reached 80° C., the poly-3-hydroxypropionate had completely melted.

On attainment of the internal temperature of 175° C., this was maintained while stirring for 300 min.

The Liebig condenser was cooled in countercurrent with water which had an inflow temperature of 20° C.

Condensable splitting products transported by the nitrogen stream were condensed in the Liebig condenser and the condensate was collected in the product flask which was likewise kept at a temperature of 20° C.

Within the aforementioned 300 min, no condensate was obtained in the product flask.

b) A sample of 34.86 mg of the poly-3-hydroxypropionate from comparative example 6 was weighed into an $Al_2O_3$ crucible and the behavior thereof on increasing temperature was analyzed simultaneously by the method of thermogravimetry and by the method of dynamic differential calorimetry ("simultaneous TG-DSC analysis").

The analysis was effected with a "NETZSCH STA 449 F3 Jupiter®" thermal analysis apparatus from Netzsch Gerätebau GmbH.

By means of FT-IR spectroscopy, the splitting gas formed in the thermolysis accompanying the thermal analysis was analyzed with respect to its main components.

In the course of the analysis, the sample was first heated to 35° C. for 10 min and then the sample temperature was increased to 610° C. at a constant rate of 5 K/min under an argon stream (40 ml/min).

As a function of temperature, the sample mass and the heat flow through the sample were detected (i.e. the dynamic differential calorimetry was executed in the form of dynamic heat flow differential calorimetry).

The thermogram obtained, with reference to FT-IR spectroscopy, showed the following three endothermic processes:
1. The melting of the P3HP without loss of mass;
   onset temperature ($oT_S$): 70.1° C.;
   peak temperature ($pT_S$): 93.6° C.
   $oT_S$=the temperature at which the melting of the sample verifiably sets in;
   $pT_S$=the temperature at which the melting operation has its highest rate;
2. Thermolysis of the sample to acrylic acid;
   onset temperature ($oT_T$): 286.5° C.;
   peak temperature ($pT_T$): 340.0° C.;
   $oT_T$=the temperature at which the thermolysis verifiably sets in;
   $pT_T$=the temperature at which the thermolysis has its maximum splitting rate;

Loss of mass: 98.8% of the starting mass;
the splitting gas comprised, as main components, acrylic acid and traces of $CO_2$.
3. Decomposition of the residual mass above 400° C.;
no onset or peak temperature determinable since the end of the measurement range was attained at 610° C.;
loss of mass by the end of the measurement range: 0.5% of the starting mass.

15. Thermolysis of the poly-3-hydroxypropionate (P3HP) not prepared in accordance with the invention from comparative example 6, in the presence of 3-hydroxypyridine as a splitting catalyst (comparative example 9)

The procedure was as in experiment "14.a)", except that the melting of the P3HP was followed by addition of 97 mg of 3-hydroxypyridine to the melt. As early as 15 min after attainment of the internal temperature of 175° C. in the splitting flask, the first condensate was obtained in the product flask (the product flask in this experiment "15" and in all subsequent thermolysis experiments did not comprise any added polymerization inhibitor). After a total of 90 min at internal temperature 175° C., the residual melt still present in the splitting flask solidified. Thereafter, the splitting experiment was stopped. Condensate droplets adhering in the distillation system were vaporized by heating them with a hot air gun, liquefied them in the Liebig condenser and collected in the product flask.

The amount of condensate present in the product flask was 2.48 g.

According to gas chromatography analysis, the condensate (based on the weight thereof) comprised 95.5%% by weight of acrylic acid, 3.6%% by weight of diacrylic acid (Michael adduct) and 0.8% by weight of higher Michael adducts of acrylic acid onto itself.

Aldehydes were undetectable in the condensate. The condensate did not comprise any 3-hydroxypyridine.

The mass of the remaining light brown, tacky residue in the splitting flask was 330 mg (11% by weight of the use amount of P3HP).

The Michael adducts also stripped by the stripping gas can be retained in a simple manner here (and in all subsequent cases) if required by conducting the stream through a rectification column (for example a Vigreux column) operated under reflux to the product flask. The splitting yield of acrylic acid can be increased correspondingly.

16. Thermolysis of the poly-3-hydroxypropionate (P3HP) not prepared in accordance with the invention from comparative example 6, in the presence of pentamethylethylenetriamine (Lupragen® N301) as a splitting catalyst (comparative example 10)

a) The procedure was as in experiment "14.a)", except that the melting of the P3HP was followed by addition of 87 mg of pentamethylethylenetriamine (supplier: BASF SE; specification: >98%, trade name: Lupragen® N301) to the melt. As early as 15 min after attainment of the internal temperature of 175° C. in the splitting flask, the first condensate was obtained in the product flask. After a total of 120 min at internal temperature 175° C., the residual melt still present in the splitting flask solidified (in tacky solid form). Thereafter, the splitting experiment was stopped. Condensate droplets adhering in the distillation system were vaporized by heating them with a hot air gun, liquified them in the Liebig condenser and collected in the product flask.

The amount of condensate present in the product flask was 2.71 g.

The condensate comprised 95.7% by weight of acrylic acid, 3.3% by weight of diacrylic acid (Michael adduct) and 0.5% by weight of higher Michael adducts of acrylic acid onto itself. Aldehydes were undetectable in the condensate. The condensate did not comprise any pentamethylethylenetriamine. The mass of the pale brown tacky residue remaining in the splitting flask was 150 mg (5% by weight of the use amount of P3HP).

b) The procedure was as in experiment "14.b)", except that the amount of P3HP sample was 36.65 mg and 0.68% by weight of pentamethylenetriamine had been added to this sample prior to the thermal analysis, based on the weight thereof.

The resulting thermogram showed, with reference to FT-IR spectroscopy, the following three endothermic processes:
1. The melting of the P3HP without loss of mass;
onset temperature: 69.6° C.;
peak temperature: 93.3° C.
2. Thermolysis of the sample to acrylic acid;
onset temperature: 208.7° C.;
peak temperature: 259.7° C.;
loss of mass: 98.9% of the starting mass;
the splitting gas comprises acrylic acid as the main component and traces of $CO_2$.
3. Decomposition of the residual mass above 300° C.;
no onset and peak temperatures determinable;
loss of mass up to the end of the measurement range: 0.3% of the starting mass.

In the case of repetition of experiments "14 a) and b)", of experiment "15" and of experiments "16. a) and b)", except using the poly-3-hydroxypropionate (P3HP) not prepared in accordance with the invention from comparative example 7 (rather than from comparative example 6) as the material to be split, this showed splitting characteristics corresponding to those of the poly-3-hydroxypropionate (P3HP) not prepared in accordance with the invention from comparative example 6.

17. Thermolysis of the poly-3-hydroxypropionate (P3HP) not prepared in accordance with the invention from experiment "6" (comparative example 11)

In experiment "6", comparative example 2 was repeated several times and mixing of various fractions removed produced a poly-3-hydroxypropionate which, based on the weight of the mass thereof, still comprised 2% by weight of cobalt.

This poly-3-hydroxypropionate was the subject of this experiment 17.

a) The procedure was as in experiment "14.a)", except that 3.0 g of the poly-3-hydroxypropionate comprising 2% by weight of Co were weighed into the splitting flask. 30 minutes after attainment of the internal temperature of 175° C. in the splitting flask, the first condensate was obtained in the product flask. After a total of 90 minutes at internal temperature 175° C., the residual melt still present in the splitting flask became extremely viscous, and so the splitting test was stopped. Condensate droplets adhering in the distillation system were vaporized by heating them with a hot air gun, liquefied in the Liebig condenser and collected in the product flask.

The amount of condensate present in the product flask was 2.14 g.

The condensate comprised 95.3% by weight of acrylic acid, 3.7% by weight of diacrylic acid (Michael adduct) and 0.5% by weight of higher Michael adducts of acrylic acid onto itself. Aldehydes were undetectable in the condensate.

The mass of the dark brown residue which was glassy and brittle at 25° C. and remained in the splitting flask was 710 mg (24% by weight of the use amount of P3HP).

An elemental analysis of the splitting residue gave the following contents based on the weight of the mass thereof:

12% by weight of Co, 46.6% by weight of C, 4.5% by weight of H, 2.9% by weight of N and 34% by weight of O.

This result correlates with a substance mixture composed of 12% by weight of Co, 19.7% by weight of 3-hydroxypyridine and 68.3% by weight of a substance having the elemental composition 50.1% by weight of C, 5.1% by weight of H and 44.9% by weight of O. The latter corresponds satisfactorily to the theoretical elemental composition of P3HP: 50.0% by weight of C, 5.59% by weight of H and 44.4% by weight of O.

A repetition of experiment "17.a)" with addition of different amounts of phenothiazine or 4-hydroxy-2,2,6,6-tetramethylpiperidine 1-N-oxyl as polymerization inhibitors led neither to an improvement in the yield of acrylic acid nor to a decrease in the splitting residue remaining.

b) The procedure was as in experiment "14.b)", except that the sample analyzed was 37.70 mg of the poly-3-hydroxypropionate comprising 2% by weight of Co.

The resulting thermogram showed, with reference to FT-IR spectroscopy, the following three endothermic processes:
1. The melting of the P3HP (with a loss of mass of 0.4% of the starting mass);
   onset temperature: 62.9° C.;
   peak temperature: 76.0° C.
2. Thermolysis of the sample to acrylic acid;
   onset temperature: 204.3° C.;
   peak temperature: 235.1° C.;
   loss of mass: 86.0% of the starting mass;
   the splitting gas comprised acrylic acid as the main component and traces of $CO_2$ and methane.
3. Decomposition of the residual mass above 300° C.;
   no onset or peak temperature determinable;
   loss of mass up to the end of the measurement range: 4.7% of the starting mass.

18. Thermolysis of the poly-3-hydroxypropionate (P3HP) not prepared in accordance with the invention from experiment "6" in the presence of pentamethylethylenetriamine (comparative example 12)

a) The procedure was as in experiment "17.a)", except that, in addition to the 3.0 g of the poly-3-hydroxypropionate comprising 2% by weight of Co, after the melting thereof, 87 mg of pentamethylethylenetriamine were also added to the splitting flask. As early as 15 min after attainment of the internal temperature of 175° C. in the splitting flask, the first condensate was obtained in the product flask. After a total of 90 min at internal temperature 175° C., the residual melt still present in the splitting flask became distinctly viscous, and so the splitting experiment was stopped. Condensate droplets adhering in the distillation system were vaporized by heating thereof with a hot air gun, liquefied in the Liebig condenser and collected in the product flask.

The amount of condensate present in the product flask was 2.21 g. The condensate comprised 96.1% by weight of acrylic acid, 3.2% by weight of diacrylic acid (Michael adduct) and 0.6% by weight of higher Michael adducts of acrylic acid onto itself. Aldehydes were undetectable in the condensate. The condensate did not comprise any pentamethylethylenetriamine.

The mass of the dark brown residue which was glassy and brittle at 25° C. and remained in the splitting flask was 690 mg (23% by weight of the use amount of P3HP). In other words, the pentamethylethylenetriamine added as a splitting catalyst is unable to significantly reduce the splitting residue in the presence of Co compared to experiment "17.a)".

b) The procedure was as in experiment "17.b)", except that the sample of P3HP was 35.43 mg of the poly-3-hydroxypropionate comprising 2% by weight of Co, and 0.58% by weight of pentamethylethylenetriamine had been added to this sample prior to the thermal analysis, based on the weight thereof.

The resulting thermogram showed, with reference to FT-IR spectroscopy, the following three endothermic processes:
1. The melting of the P3HP (with a loss of mass of 0.4% of the starting mass);
   onset temperature: 62.6° C.;
   peak temperature: 75.5° C.
2. Thermolysis of the sample to acrylic acid;
   onset temperature: 191.5° C.;
   peak temperature: 222.6° C.;
   loss of mass: 88.4% of the starting mass;
   the splitting gas comprised acrylic acid as the main component and traces of $CO_2$ and methane.
3. Decomposition of the residual mass above 290° C.;
   no onset and peak temperature was determinable;
   loss of mass up to the end of the measurement range: 4.6% of the starting mass.

In other words, the added pentamethylethylenetriamine considerably lowers the activation energy required for the thermolysis compared to experiment "17.b)" in spite of the cobalt content.

19. Thermolysis of the poly-3-hydroxypropionate (P3HP) prepared in accordance with the invention from example 2 (example 7)

a) The procedure was as in experiment "14.a)", except that 3.0 g of the poly-3-hydroxypropionate comprising 0.2% by weight of Co from example 2 were weighed into the splitting flask. 30 minutes after attainment of the internal temperature of 175° C. in the splitting flask, the first condensate was obtained in the product flask. After a total of 135 min at internal temperature 175° C., the residual melt still present in the splitting flask became distinctly viscous, and so the splitting experiment was stopped. Condensate droplets adhering in the distillation system were vaporized by heating them with a hot air gun, liquefied in the Liebig condenser and collected in the product flask.

The amount of condensate present in the product flask was 2.51 g. The condensate comprised 95.6% by weight of acrylic acid, 3.2% by weight of diacrylic acid (Michael adduct) and 0.6% by weight of higher Michael adducts of acrylic acid onto itself. Aldehydes were undetectable in the condensate.

The mass of the dark brown residue which was glassy and brittle at 25° C. and remained in the splitting flask was 360 mg (12% by weight of the use amount of P3HP).

b) The procedure was as in experiment "14.b)", except that the sample analyzed was 36.65 mg of the poly-3-hydroxypropionate comprising 0.2% by weight of cobalt from example 2.

The resulting thermogram showed, with reference to FT-IR spectroscopy, the following three endothermic processes:
1. The melting of the P3HP without loss of mass;
   onset temperature: 60.9° C.;
   peak temperature: 86.9° C.
2. Thermolysis of the sample to acrylic acid;
   onset temperature: 197.2° C.;
   peak temperature: 236.4° C.;
   loss of mass: 97.3% of the starting mass;
   the splitting gas comprised acrylic acid as the main component and traces of $CO_2$.
3. Decomposition of the residual mass above 290° C.;
   no onset and peak temperatures determinable;
   loss of mass up to the end of the measurement range: 1.0% of the starting mass.

20. Thermolysis of the poly-3-hydroxypropionate (P3HP) prepared in accordance with the invention from example 2, in the presence of pentamethylethylenetriamine (example 8)

a) The procedure was as in experiment "19.a)", except that, in addition to the 3.0 g of the poly-3-hydroxypropionate comprising 0.2% by weight of Co, after the melting thereof, 87 mg of pentamethylethylenetriamine were also added to the splitting flask. As early as 15 min after attainment of the internal temperature of 175° C. in the splitting flask, the first condensate was obtained in the product flask. After a total of 90 min at internal temperature 175° C., the residual melt still present in the splitting flask became distinctly viscous, and so the splitting experiment was stopped. Condensate droplets adhering in the distillation system were vaporized by heating thereof with a hot air gun, liquefied in the Liebig condenser and collected in the product flask.

The amount of condensate present in the product flask was 2.56 g. The condensate comprised 96.2% by weight of acrylic acid, 2.9% by weight of diacrylic acid (Michael adduct) and 0.5% by weight of higher Michael adducts of acrylic acid onto itself.

Aldehydes were undetectable in the condensate. The condensate did not comprise any pentamethylethylenetriamine.

The mass of the dark brown residue which was glassy and brittle at 25° C. and remained in the splitting flask was 240 mg (8% by weight of the use amount of P3HP).

b) The procedure was as in experiment "19.b)", except that the sample of P3HP was 35.02 mg of the poly-3-hydroxypropionate comprising 0.2% by weight of cobalt from example 2, and 0.56% by weight of pentamethylethylenetriamine had been added to this sample prior to the thermal analysis, based on the weight thereof. The resulting thermogram showed, with reference to FT-IR spectroscopy, the following three endothermic processes:
1. The melting of the P3HP without loss of mass;
   onset temperature: 60.6° C.;
   peak temperature: 84.8° C.
2. Thermolysis of the sample to acrylic acid;
   onset temperature: 192.9° C.;
   peak temperature: 228.3° C.;
   loss of mass: 97.4% of the starting mass;
   the splitting gas comprised acrylic acid as the main component and traces of $CO_2$.
3. Decomposition of the residual mass above 290° C.;
   no onset and peak temperatures determinable;
   loss of mass up to the end of the measurement range: 1.2% of the starting mass.

21. Thermolysis of a mixture of two poly-3-hydroxypropionates (P3HP) not prepared in accordance with the invention: the P3HP from comparative example 6 and the P3HP comprising 2% by weight of cobalt based on the weight of the mass thereof from experiment "6" (comparative example 13)

The procedure was as in experiment "14.a)", except that a mixture of 2.5 g of the P3HP from comparative example 6 and 2.5 g of the P3HP comprising 2% by weight of Co based on the weight of the mass thereof from experiment "6" was weighed into the splitting flask. 30 minutes after attainment of the internal temperature of 175° C. in the splitting flask, the first condensate was obtained in the product flask. After a total of 120 min at an internal temperature of 175° C., the residual melt still present in the splitting flask became distinctly viscous, and so the splitting experiment was stopped. Condensate droplets adhering in the distillation system were vaporized by heating them with a hot air gun, liquefied in the Liebig condenser and collected in the product flask.

The amount of condensate present in the product flask was 4.15 g. The condensate comprised 96.8% by weight of acrylic acid, 2.7% by weight of diacrylic acid (Michael adduct) and 0.3% by weight of higher Michael adducts of acrylic acid onto itself. Aldehydes were undetectable in the condensate.

The mass of the dark brown residue which was glassy and brittle at 25° C. and remained in the splitting flask was 580 mg (12% by weight of the use amount of P3HP).

22. Thermolysis of the poly-3-hydroxypropionate (P3HP) not prepared in accordance with the invention from comparative example 6, in the presence of N-benzylamine as a splitting catalyst (comparative example 14)

The procedure was as in experiment "14.a)", except that, after the melting of the P3HP, 90 mg of N-benzylamine (supplier: Sigma-Aldrich; specification: >99%, catalog number: 185701) were added to the melt. On attainment of the internal temperature of 175° C., this was maintained with stirring for another 300 min. Then the thermolysis experiment was stopped.

Within the aforementioned 300 min, no condensate was obtained in the product flask.

The contents remaining in the splitting flask solidified at an internal temperature of 55° C. to give a pale beige wax. The amount of the wax was 3.06 g (99.0% by weight of the use amount of P3HP and benzylamine). The weight-average relative molecular weight $M_W$ of the P3HP content was 1900 after the experiment, at a polydispersity Q of 2.7.

23. Evidence of the removability of pentamethylethylenetriamine used as a splitting catalyst from the splitting residue of experiment "16.a)" by gas chromatography separation of constituents which escape in gaseous form in the course of thermal treatment of this splitting residue and subsequent elucidation of the structure of these constituents by mass spectrometry (method of programmed pyrolysis GC/MS coupling) and FT-IR The thermal treatment of the splitting residue was effected in a circular cylindrical crucible made of V2A steel (height: 6.2 mm; wall thickness: 0.2 mm; external diameter: 2.5 mm). The sample of splitting residue from experiment "16.a)" weighed into the crucible was 0.23 mg. The crucible was introduced into the center of a circular cylindrical tube made of quartz glass (height 25 mm; internal diameter 5 mm; wall thickness 0.5 mm). The quartz glass tube was electrically heatable from the outside.

A gas stream of He was conducted through the quartz glass tube (20 ml/min, inlet temperature into the quartz glass tube=25° C.), and this flowed in the direction of the crucible present in the tube (the opening of the crucible faced in the direction of the He stream), took up any gaseous constituents escaping therefrom and conveyed them in flow direction into a gas chromatography separating column. The length of the separating column was 30 m; the internal diameter thereof was 0.25 mm. As a stationary phase, it had a film of polydimethylsiloxane of layer thickness 1 µm (this column had been purchased commercially from Agilent Technologies as the "HP-1 ms" model).

The start temperature of the electrical heating of the quartz tube was 100° C. This was increased to 400° C. with a ramp of 10° C./min and then held at this temperature.

Until the attainment of 400° C., the constituents which exited in gaseous form from the sample thermally treated in the crucible and were conveyed with the He stream in the separating column were cryofocused on entry into it. For this purpose, the entire separating column was within a Dewar vessel filled with liquid nitrogen.

Subsequently, the temperature of the entire separating column was increased to 40° C. and held at this temperature for 2 min. Then the temperature of the entire column was increased at a heating rate of 6° C./min up to a final temperature of 320° C. Finally, this final temperature was maintained for another 13 min. Over the entire period, the He stream flowed through the heated quartz glass tube comprising the crucible into the separating column and from the separating column into a mass spectrometer.

In addition, in a further experiment, the gas stream flowing out of the separating column was analyzed by means of FT-IR.

Pentamethylethylenetriamine was identified unambiguously as the main constituent in the He stream.

U.S. Provisional Patent Application No. 61/671,852, filed Jul. 16, 2012, is incorporated into the present patent application by literature reference. With regard to the above-mentioned teachings, numerous changes and deviations from the present invention are possible. It can therefore be assumed that the invention, within the scope of the appended claims, can be performed differently than the way described specifically herein.

The invention claimed is:

1. A process for preparing acrylic acid from ethylene oxide and carbon monoxide, the process comprising:
converting by carbonylating ethylene oxide dissolved in an aprotic solvent with carbon monoxide at elevated pressure and elevated temperature in the presence of a catalyst system comprising a cobalt source in a reaction zone A to obtain a product mixture A comprising poly-3-hydroxypropionate,
removing poly-3-hydroxypropionate from the product mixture A in a separation zone A, and
thermolyzing poly-3-hydroxypropionate removed in separation zone A in a thermolysis zone A to form acrylic acid,
wherein the removing comprises at least one of:
adding water, an aqueous solution, or both, as an aqueous precipitation liquid to a portion of product mixture A, to a total amount of product mixture A, or both, in order to precipitate poly-3-hydroxypropionate presently dissolved in the portion of product mixture A or in the total amount of product mixture A; or
washing poly-3-hydroxypropionate removed from product mixture A in separation zone A with water, with an aqueous solution, or both, as an aqueous wash liquid.

2. The process according to claim 1, wherein the aprotic solvent comprises or is at least one solvent selected from the group consisting of saturated hydrocarbon, aromatic hydrocarbon, halogenated saturated hydrocarbon, halogenated aromatic hydrocarbon, an ester of organic acids, a ketone, a nitrile, a diakylamide, a carbonic ester, a sulfoxide, a sulfone, an N-alkylpyrrolidone, a cyclic ether and an acyclic ether.

3. The process according to claim 1, wherein the aprotic solvent comprises or is at least one solvent selected from the group consisting of n-hexane, n-heptane, petroleum ether, cyclohexane, benzene, toluene, dichloromethane, n-butyl propionate, phenyl acetate, glyceryl acetate, acetic acid ethyl acetate, acetone, ethyl methyl ketone, methyl isobutyl ketone, benzophenone, acetonitrile, propionitrile, n-butyronitrile, benzonitrile, dimethylformamide, dimethylacdetamide, dimethyl carbonate, diethyl carbonate, ethyl methyl carbonate, ethylene carbonate, propylene carbonate, dimethyl sulfoxide, sulfolane, N-methylpyrrolidone, ethylene oxide, diethyl ether, anisole, tetahydrofuran, 1,4-dioxane, diphenyl ether, alkylene glycol diakyl ether, and polyalkylene glycol dialkyl ether.

4. The process according to claim 1, wherein the aprotic solvent is an aprotic solvent only to an extent of at least 90% of its weight.

5. The process according to claim 1, wherein the poly-3-hydroxypropionate removed from product mixture A has a relative weight-average molecular weight of from 1000 to 20,000.

6. The process according to claim 1, wherein the catalyst system comprises the cobalt source in such an amount that it comprises, based on a molar amount of ethylene oxide for carbonylating conversion, of from 0.005 to 20 mol % of Co.

7. The process according to claim 1, wherein the cobalt source is a salt of cobalt.

8. The process according to claim 1, wherein the cobalt source is dicobalt octacarbonyl.

9. The process according to claim 1, wherein the catalyst system comprises a Brønsted acid as cocatalyst A, a Brønsted base as cocatalyst B, or a Brønsted acid as cocatalyst A and a Brønsted base as cocatalyst B.

10. The process according to claim 1, wherein the catalyst system comprises a compound as a cocatalyst C which has both a nucleophilic Brønsted-basic functionality like a cocatalyst B and a Brønsted-acidic functionality like a cocatalyst A.

11. The process according to claim 10, wherein the cocatalyst C is at least one compound selected from the group consisting of 2-hydroxypyridine, 3-hydroxypyridine, 4-hydroxypyridine, 3,4-dihydroxypyridine, 3-hydroxyquinoline, 4-hydroxy-2-methylpyridine, 3-hydroxy-4-methylpyridine, 2,6-dihydroxypyridine, 2-hydroxyquinoline, 1-hydroxyisoquinoline, 3-hydroxyquinoline, 2,3-dihydroxyquinoxaline, 8-hydroxyquinoline, 2-pyridylmethanol, 3-pyridylmethanol, 2-(2-pyridyl)ethanol and nicotinic acid.

12. The process according to claim 10, wherein the aprotic solvent comprises diglyme, the cobalt source comprises dicobalt octacarbonyl, and the catalyst system additionally comprises 3-hydroxypyridine as cocatalyst C.

13. The process according to claim 1, wherein the converting of ethylene oxide is ≥90 mol %.

14. The process according to claim 1, wherein a pH of the aqueous precipitation liquid, based on a temperature of 25° C. and a pressure of $1.0133 \cdot 10^5$ Pa, is ≤7.5.

15. The process according to claim 1, wherein a pH of the aqueous precipitation liquid, based on a temperature of 25° C. and a pressure of $1.0133 \cdot 10^5$ Pa, is ≥0.

16. The process according to claim 1, wherein a pH of product mixture A or of a portion of product mixture A on completion of the adding of an aqueous precipitation liquid, based on a temperature of 25° C. and a pressure of $1.0133 \cdot 10^5$ Pa, is ≤7.5.

17. The process according to claim 1, wherein a pH of product mixture A or of a portion of product mixture A on completion of the adding of an aqueous precipitation liquid, based on a temperature of 25° C. and a pressure of $1.0133 \cdot 10^5$ Pa, is ≥0.

18. The process according to claim 1, wherein the aqueous precipitation liquid is the aqueous solution of an inorganic acid, of an organic acid, or both.

19. The process according to claim 1, wherein the aqueous precipitation liquid is an aqueous acetic acid solution.

20. The process according to claim 1, wherein the adding of the aqueous precipitation liquid is undertaken in the presence of an oxidizing agent for Co in oxidation states <+2.

21. The process according to claim 20, wherein the adding of the aqueous precipitation liquid is undertaken in the presence of air or in the presence of a molecular oxygen-comprising gas other than air.

22. The process according to claim 1, wherein a pH of the aqueous wash liquid, based on a temperature of 25° C. and a pressure of $1.0133 \cdot 10^5$ Pa, is ≤7.5.

23. The process according to claim 1, wherein a pH of the aqueous wash liquid, based on a temperature of 25° C. and a pressure of $1.0133 \cdot 10^5$ Pa, is ≥0.

24. The process according to claim 1, wherein the aqueous wash liquid is the aqueous solution of an inorganic acid, of an organic acid, or both.

25. The process according to claim 1, wherein the aqueous wash liquid is an aqueous acetic acid solution.

26. The process according to claim 1, wherein the washing of poly-3-hydroxypropionate removed from product mixture A is effected in the presence of an oxidizing agent for Co in oxidation states <+2.

27. The process according to claim 1, wherein the washing of the poly-3-hydroxypropionate removed from product mixture A is undertaken in the presence of air, a molecular oxygen-comprising gas other than air, or both.

28. The process according to claim 1, wherein the thermolyzing of the poly-3-hydroxypropionate removed in a separation zone A is effected from a solid substance thereof, from a melt thereof, from a solution thereof in a solvent, from a suspension thereof in a dispersant, or from an emulsion thereof in a dispersant.

29. The process according to claim 1, wherein 7 a splitting catalyst which catalyzes the thermolyzing is added to the poly-3-hydroxypropionate removed in a separation zone A.

30. The process according to claim 28, wherein a splitting catalyst which catalyzes the thermolyzing is added to the solid substance, to the melt, to the solution, to the suspension, or to the emulsion.

31. The process according to claim 29, wherein the splitting catalyst is a molecular organic active compound consisting of carbon atoms, hydrogen atoms, at least one nitrogen atom and optionally at least one oxygen atom in covalently bonded form, and the nitrogen atom is a tertiary nitrogen atom.

32. The process according to claim 31, wherein the molecular organic active compound has a tertiary nitrogen atom which has a covalent bond to three different carbon atoms.

33. The process according to claim 31, wherein the molecular organic active compound has at least two tertiary nitrogen atoms or at least three tertiary nitrogen atoms which each have a covalent bond to three different carbon atoms.

34. The process according to claim 31, wherein a molar mass of the molecular organic active compound is ≥59.1 g/mol and ≤600 g/mol.

35. The process according to claim 1, wherein the process for preparing acrylic acid is followed by a process comprising free-radical polymerizing the acrylic acid to form a polymer, optionally with other one or more monounsaturated compounds, polyunsaturated compounds, or both.

36. The process according to claim 1, wherein a cobalt content of the poly-3-hydroxypropionate removed in a separation zone A in the thermolyzing is from 0 to 1% by weight.

37. The process according to claim 1, wherein a cobalt content of the poly-3-hydroxypropionate in the thermolyzing is from $10^{-6}$ to 1% by weight.

38. The process according to claim 36, wherein the cobalt contents are the total contents in the poly-3-hydroxypropionate of $Co^{+2}$.

39. The process according to claim 36, wherein the cobalt contents are the total contents in the poly-3-hydroxypropionate of $Co^{+1}$.

40. The process according to claim 36, wherein the cobalt contents are the total contents in the poly-3-hydroxypropionate of $Co^0$.

41. The process according to claim 36, wherein the cobalt contents are the total contents in the poly-3-hydroxypropionate of $Co^{-1}$.

42. The process according to claim 1, wherein the aqueous precipitation liquid comprises an organic solvent other than an inorganic acid, an organic acid, or both.

43. The process according to claim 1, wherein the aqueous wash liquid comprises an organic solvent other than an inorganic acid, an organic acid, or both.

* * * * *